514-157 SP
6/25/85 OF RE 31,926

United States Patent [19]
Wetzel et al.
[11] E Patent Number: Re. 31,926
[45] Reissued Date of Patent: Jun. 25, 1985

[54] PENICILLINS AND SALTS THEREOF

[75] Inventors: Bernd Wetzel, Biberach an der Riss; Wolfgang Reuter, Laupertshausen; Eberhard Woitun; Roland Maier, both of Biberach an der Riss; Uwe Lechner, Ummendorf; Hanns Goeth; Rolf Werner, both of Biberach an der Riss, all of Fed. Rep. of Germany

[73] Assignee: Boehringer Ingelheim GmbH, Ingelheim am Rhein, Fed. Rep. of Germany

[21] Appl. No.: 420,804

[22] Filed: Sep. 21, 1982

Related U.S. Patent Documents

Reissue of:
[64] Patent No.: 4,241,056
Issued: Dec. 23, 1980
Appl. No.: 13,006
Filed: Feb. 21, 1979

[30] Foreign Application Priority Data

Feb. 25, 1978 [DE] Fed. Rep. of Germany ..... 2808153
Nov. 27, 1978 [DE] Fed. Rep. of Germany ..... 2851226
Nov. 27, 1978 [DE] Fed. Rep. of Germany ..... 2851270

[51] Int. Cl.[3] ..... A61K 31/655; A61K 31/43; C07D 499/68; C07D 499/70

[52] U.S. Cl. ..... 514/157; 260/239.1; 514/195

[58] Field of Search ..... 424/226, 229, 246, 248.51, 424/251, 271; 260/239.1

[56] References Cited

U.S. PATENT DOCUMENTS 3,634,405 1/1972 Holdredge ..... 260/239.1
4,031,230 6/1977 Gottschlich et al. ..... 424/271
4,038,271 7/1977 Breuer et al. ..... 260/239.1
4,103,011 7/1978 Minami et al. ..... 424/251

*Primary Examiner*—Natalie Trousof
*Assistant Examiner*—Vera C. Clarke
*Attorney, Agent, or Firm*—Hammond & Littell, Weissenberger & Dippert

[57] ABSTRACT

Compounds of the formula

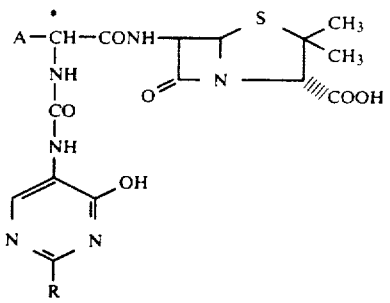

wherein

A is phenyl; 4-hydroxy-phenyl; 2- or 3-thienyl; cyclohexyl; cyclohexen-1-yl; cyclohexa-1, 4-dien-1-yl; or 3,4-disubstituted phenyl, where the substituents may be identical to or different from each other and are selected from the group consisting of chlorine, hydroxyl or methoxy; and R is an aliphatic, cycloaliphatic; aromatic or heterocyclic group of diverse types;

and non-toxic, pharmacologically acceptable salts thereof formed with inorganic or organic bases. The compounds as well as their salts are useful as antibiotics.

8 Claims, No Drawings

PENICILLINS AND SALTS THEREOF

Matter enclosed in heavy brackets [ ] appears in the original patent but forms no part of this reissue specification; matter printed in italics indicates the additions made by reissue.

This invention relates to novel penicillins and salts thereof, as well as to methods of preparing these compounds, pharmaceutical compositions containing them as active ingredients, and methods of using them as antibiotics.

BACKGROUND OF THE INVENTION AND PRIOR ART

It is known that penicillin antibiotics inhibit the growth of various grampositive and gramnegative bacteria. It is further known that only few penicillins have a good activity against important gramnegative problematic germs, such as Pseudomonas and Klebsiella, which occur primarily in hospitals. During the last years the frequency of occurrence of infections which are caused by these germs, particularly by Pseudomonas, has increased steadily. While penicillin derivatives such as Carbenicillin (U.S. Pat. No. 3,142,673), Sulbenicillin (U.S. Pat. No. 3,660,379) as well as Ticarcillin (U.S. Pat. No. 3,282,926) are described as antipseudomonal antibiotics, they show in vivo as well as in vitro only a poor activity. An important further development are acylated derivatives of α-aminobenzylpenicillins, e.g. Ampicillin and Amoxycillin. These kinds of compounds have been intensively studied during the last years, and as a result Azlocillin, i.e. 6-{D-α-[(2-oxoimidazolidine-1-yl)carbonylamino]-4-phenylacetamino}-pencillanic acid sodium salt (e.g. Belgian Pat. No. 767,647), has recently been introduced on the market as a further antipseudomonas penicillin. For a successful treatment, however, this penicillin must be administered at high dosages. Moreover, it has only a moderate activity against Klebsiella and various kinds of E. coli. Therefore, it is still a need to search for new penicillins having an increased effectiveness against bacteria such as Pseudomonas resp. Klebsiella and E. coli.

While, as mentioned above, much research work has been and is still being done concerning acyl derivatives of α-aminobenzylpenicillins, there is little knowledge about derivatives in which a heterocycle is attached over a ureido bridge.

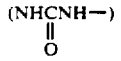

to the α-benzyl carbon atoms of α-amino-benzylpenicillins. Only in German Offenlegungsschriften Nos. 2,450,668 and 25 35 655 and in U.S. Pat. No. 4,031,230 hydroxypyridylureido-benzyl-penicillins of the formula

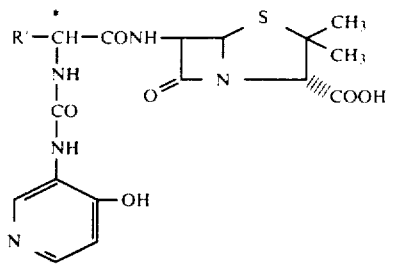

(II)

are disclosed. These compounds are nearest in their structure to the novel penicillins of the present invention. As shown in table I below, a number of the novel penicillins according to the present invention distinguish themselves by a significantly stronger antibacterial activity, particularly against bacteria such as E. coli, Pseudomonas and Klebsiella.

DESCRIPTION OF THE INVENTION

More particularly, the present invention relates to novel penicillins represented by the formula

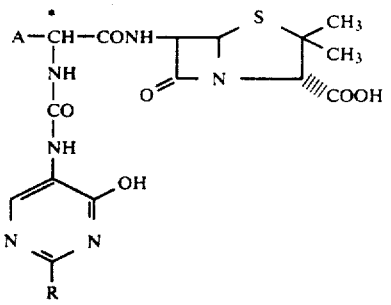

(I)

wherein

A represents the phenyl, 4-hydroxyphenyl, 2- or 3-thienyl, cyclohexyl, cyclohexen-1-yl or cyclohexa-1,4-dien-1-yl group; as well as a phenyl group disubstituted in 3,4-position, where the substituents may be the same or different and can represent chlorine atoms, hydroxy or methoxy groups;

R represents a hydrogen atom, an aliphatic straight or branched hydrocarbon radical with 1 to 8 carbon atoms optionally containing one or two double bonds or optionally containing a triple bond; the cyclopropyl radical, which optionally may be substituted with one or two methyl groups or an ethyl group or a phenyl group; a cycloalkyl radical with 4 to 8 carbon atoms optionally containing one or more double bonds;

a group of the general formula

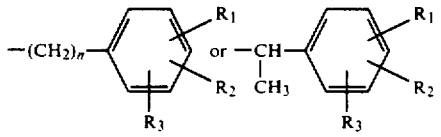

where n represents 0 or 1, and $R_1$, $R_2$ and $R_3$, which may be the same or different from each other, represent hydrogen or halogen atoms, free amino groups, alkylamino or dialkylamino groups of 1 to 4 carbon atoms, hydroxy groups, alkoxy groups of 1 to 4 carbon atoms, nitro groups, formylamino groups, aliphatic acylamino groups of 1 to 4 carbon atoms in the alkyl moiety; alkylsulfonylamino groups of 1 to 4 carbon atoms; alkylcarbonyl groups of 1 to 4 carbon atoms in the alkyl moiety; alkylcarbonyloxy groups of 1 to 4 carbon atoms in the alkyl part; alkoxy-carbonyl groups of 1 to 4 carbon atoms in the alkyl moiety; aminocarbonyl groups optionally substituted by one or two alkyl groups of 1 to 3 carbon atoms; cyano groups; alkylmercapto, alkylsulfoxy or alkylsulfonyl groups of 1 to 4 carbon atoms; aminosulfonyl, alkylaminosulfonyl or dialkylaminosulfonyl groups of 1 to 4 carbon atoms in the alkyl moiety; trifluoromethylsulfonyl groups; straight or branched alkyl groups of 1 to 4 carbon atoms; trifluoromethyl groups; or phenyl groups;

R furthermore represents the $\beta$-phenylethyl group, the $\gamma$-phenyl-propyl group or the $\beta$-phenylethylidene group; the cyclopropyl-methyl or the 1-cyclopropylethyl group; the hydroxy group; an alkoxy or alkenyloxy group of 1 to 8 carbon atoms; a cycloalkoxy group of 3 to 6 carbon atoms; the phenoxy or benzyloxy group; the free mercapto group; an alkylmercapto group of 1 to 8 carbon atoms; a cycloalkylmercapto group of 3 to 6 carbon atoms; the phenylmercapto, benzylmercapto or p-chlorobenzylmercapto group; an alkylsulfinyl group of 1 to 4 carbon atoms; a group of the formula

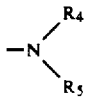

where $R_4$ and $R_5$, which may be the same or different, represent hydrogen atoms; aliphatic straight or branched hydrocarbon radicals of 1 to 8 carbon atoms optionally containing one or two double bonds or a triple bond; cycloalkyl radicals of 3 to 8 carbon atoms which may be substituted with one or two methyl groups or ethyl groups and may contain one or more double bonds; cycloalkyl-substituted alkyl groups of 3 to 8 carbon atoms in the cycloalkyl moiety and 1 to 3 carbon atoms in the alkyl moiety; or $R_4$ and $R_5$ together can also form an alkylene chain of 2 to 7 carbon atoms, so that a 3- to 8-membered heterocyclic ring is formed, which may optionally be substituted with one or two alkyl groups of 1 to 3 carbon atoms or a benzyl group, or may contain one or two double bonds or may be fused with a phenyl ring;

R represents, moreover, a group of the formula

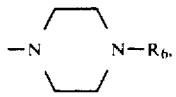

where $R_6$ represents a hydrogen atom; the formyl, acetyl, ethoxycarbonyl, benzyloxycarbonyl, methyl, ethyl, phenyl or benzyl group;

R also represents the morpholino, thiomorpholino, thiomorpholino-S-oxide or thiomorpholino-S,S-dioxide group; or a group of the formula

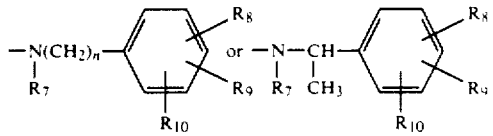

where $R_7$ represents a hydrogen atom or the methyl or ethyl group;

n represents the numbers 0, 1 or 2; and $R_8$, $R_9$ and $R_{10}$, which may be the same or different from each other, represent hydrogen; halogen; free amino groups; alkylamino or dialkylamino groups, where each alkyl moiety contains 1 to 6 carbon atoms, preferably 1 to 3 carbon atoms; pyrrolidyl; piperidyl; hydroxy or alkoxy groups of 1 to 6 carbon atoms, preferably 1 to 3 carbon atoms; formylamino and formylalkylamino groups of 1 to 3 carbon atoms; aliphatic acylamino and acylalkylamino groups of 1 to 4 carbon atoms in the alkyl moiety and 1 to 3 carbon atoms in the acyl moiety; trifluoroacetylamino groups; aminocarbonylamino, alkylaminocarbonylamino or dialkylaminocarbonylamino groups of 1 to 6, preferably 1 to 3 carbon atoms in each alkyl group; nitro; alkylsulfonylamino and alkylsulfonylalkylamino groups of 1 to 4 carbon atoms in each alkyl moiety; hydroxysulfonylamino or hydroxysulfonylalkylamino groups of 1 to 3 carbon atoms in the alkyl moiety; amidino; guanidino; formyl or alkylcarbonyl groups of 1 to 6, preferably 1 to 3 carbon atoms; benzoyl groups; alkylcarbonyloxy, alkoxycarbonyl or alkoxycarbonyloxy groups of 1 to 6, preferably 1 to 3 carbon atoms; formyloxy; carboxyl; aminocarbonyl; alkyl- or dialkylaminocarbonyl, aminocarboxyl, alkylaminocarboxyl or dialkylaminocarboxyl groups, each of 1 to 4 carbon atoms; alkoxycarbonylamino and alkoxycarbonylalkylamino groups of 1 to 4 carbon atoms in each alkyl moiety; cyano; mercapto; alkylmercapto, trifluoromethylmercapto, alkylsulfoxy and alkylsulfonyl groups of 1 to 6, preferably 1 to 3 carbon atoms; trifluoromethylsulfonyl, aminosulfonyl, alkyl- or dialkylaminosulfonyl groups of 1 to 4 carbon atoms; hydroxysulfonyl, alkoxysulfonyl, aminosulfonyloxy, alkyl- or dialkylaminosulfonyloxy groups of 1 to 4 carbon atoms; straight or branched alkyl groups of 1 to 6, preferably 1 to 3 carbon atoms, which may also contain double bonds or may be substituted with further halogen atoms; azido, dialkylmethyleneimino or dialkylaminomethylideneimino groups of 2 to 6 carbon atoms; or phenyl groups;

R may further represent a group of the formula

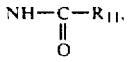

where $R_{11}$ represents a hydrogen atom; an alkyl or alkenyl group of 1 to 8 carbon atoms; a cycloalkyl group of 3 to 6 carbon atoms; a phenyl or benzyl group; or a group of the formula

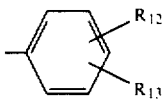

where $R_{12}$ and $R_{13}$, which may be the same or different from each other, represent hydrogen or chlorine atoms; methoxy or methyl groups;

$R_{11}$ may also represent a group of the formula $C_nF_{2n+1}$, where n represents the numbers 1 to 4; an alkoxy group of 1 to 4 carbon atoms; the benzyloxy group; a cycloalkoxy group of 3 to 6 carbon atoms; the free amino group; an alkyl- or dialkylamino group of 1 to 8 carbon atoms in the alkyl moiety; a cycloalkylamino group of 3 to 6 carbon atoms; a cycloalkyleneamino group with 3 to 6 carbon atoms; [or] a group of the formula

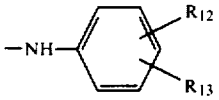

where $R_{12}$ and $R_{13}$ have the meanings defined above; or the benzylamino group; or R may also represent a group of the formula $NHSO_2R_{14}$, where $R_{14}$ represents an alkyl group of 1 to 6 carbon atoms, a cycloalkyl group of 3 to 6 carbon atoms, the benzyl group, phenyl optionally substituted with one to three methyl groups, the free amino group or an alkyl- or dialkylamino group of 1 to 6 carbon atoms in the alkyl moiety.

Preferred compounds of the formula I are those where

A represents the phenyl, p-hydroxyphenyl, 2- or 3-thienyl, 3-chloro-4-hydroxyphenyl, 3,4-dihydroxyphenyl or 1,4-cyclohexadien-1-yl group; and R is a hydrogen atom; an aliphatic straight or branched hydrocarbon group of 1 to 4 carbon atoms, which may contain a double or a triple bond; the cyclopropyl group which may be substituted by a methyl or ethyl group; a cycloalkyl group of 4 to 6 carbon atoms which may contain a double bond; a group of the formula

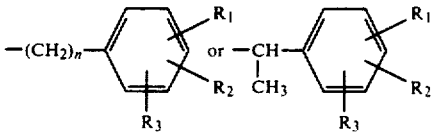

where [N] $n$ and $R_1$, $R_2$ and $R_3$ have the meaning previously defined; the cyclopropylmethyl and the 1-cyclopropylethyl groups; the hydroxy group; and alkoxy group of 1 to 4 carbon atoms; a group of the formula

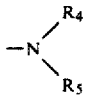

where $R_4$ and $R_5$ have the previously defined meanings; a group of the formula

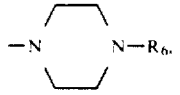

where $R_6$ has the previously defined meanings, the morpholino, thiomorpholino, thiomorpholino-S-oxide or thiomorpholino-S,S-dioxide group; a group of the formula

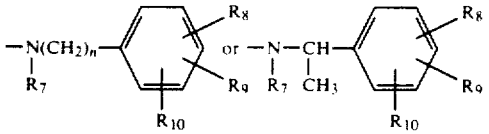

where $R_7$ to $R_{10}$ and n have the previously defined meanings; a group of the formula $NHCOR_{11}$, where $R_{11}$ represents a hydrogen atom, an alkyl group of 1 to 4 carbon atoms, a cycloalkyl group of 3 to 6 carbon atoms, an optionally chlorine substituted phenyl group, a group of the formula $C_nF_{2n+1}$, where n represents the numbers 1 to 4, an alkoxy group of 1 to 4 carbon atoms, the free amino group, an alkyl- or dialkylamino group of 1 to 4 carbon atoms in the alkyl moiety, a cyclopropylamino group, a cycloalkyleneamino group of 4 to 5 carbon atoms or a group of the formula

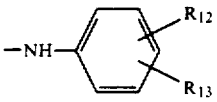

where $R_{12}$ and $R_{13}$ have the previously defined meanings; or R further represents an alkylsulfonylamino group of 1 to 3 carbon atoms in the alkyl moiety, the toluenefonylamino group, the aminosulfonylamino group or an alkyl- or dialkylaminosulfonylamino group of 1 to 4 carbon atoms in the alkyl moiety.

Especially preferred compounds of the formula I are those where

A represents the phenyl, p-hydroxyphenyl or 1,4-cyclohexadien-1-yl group; and

R is a hydrogen atom; the methyl, ethyl, isopropyl, vinyl, allyl, propargyl or crotyl group; the cyclopropyl group; the 1- or 2-methylcyclopropyl-(1)-group; the cyclobutyl group; or a group of the formula

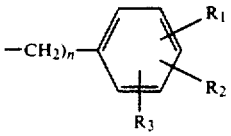

where n represents the numbers 0 or 1, and one or two of the radicals $R_1$, $R_2$ and $R_3$ represent halogen atoms, particularly chlorine or fluorine atoms; methyl, ethyl, methoxy, ethoxy, methylamino, dimethylamino, acetylamino, methylsulfonylamino, acetyl, methoxycarbonyl, methylaminocarbonyl, dimethylaminocarbonyl, methylmercapto, methylsulfoxy, methylsulfonyl, methylcarbonyloxy, nitro, cyano, trifluoromethyl or hydroxy groups, and the other radicals $R_1$, $R_2$ and $R_3$ represent hydrogen atoms; or R represents the 1-phenyl-ethyl group, the cyclopropylmethyl group, the hydroxy, methoxy or ethoxy group or a group of the formula

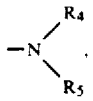

where $R_4$ and $R_5$ have the previously defined meanings; or

R represents a group of the formula

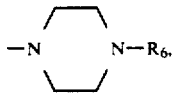

where $R_6$ represents the phenyl, formyl or acetyl group; or

R represents the morpholino group or a group of the formula

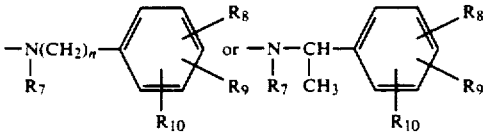

where $R_7$ represents a hydrogen atom or the methyl group;

n represents the numbers 0, 1 or 2; and one or two of the radicals $R_8$, $R_9$, $R_{10}$ represent halogen atoms, especially bromine, chlorine or fluorine atoms; methyl, ethyl, isopropyl, amino, methylamino, dimethylamino, hydroxy, methoxy, ethoxy, nitro, acetylamino, methylsulfonyl, amidino, guanidino, acetyl, methylcarbonyloxy, methoxycarbonyl, carboxyl, aminocarbonyl, methyl and dimethylaminocarbonyl, cyano, methylmercapto, methylsulfoxy, methylsulfonyl, aminosulfonyl or trifluoromethyl groups, and the remaining radicals $R_8$, $R_9$ and $R_{10}$ represent hydrogen; or R represents a group of the general formula $NHCOR_{11}$, where $R_{11}$ represents a hydrogen atom, an alkyl group of 1 to 4 carbon atoms, a cycloalkyl group of 3 to 6 carbon atoms, the trifluoroacetyl, pentafluoroethyl, heptafluoropropyl group, an ethoxy group, an amino, alkyl- or dialkylamino group of 1 to 4 carbon atoms, in the alkyl moiety, a cyclopropylamino group, a pyrrolidino or piperidino group, a phenylamino or p-chlorophenylamino group; or R represents the methyl-, ethyl- or toluene-sulfonylamino group.

The penicillin compounds of the formula I can occur in two tautomeric forms (i.e. of the lactim or of the lactam type). Which of the forms I or I' is predominant, depends especially on the respective solvent and on the type of substituent R:

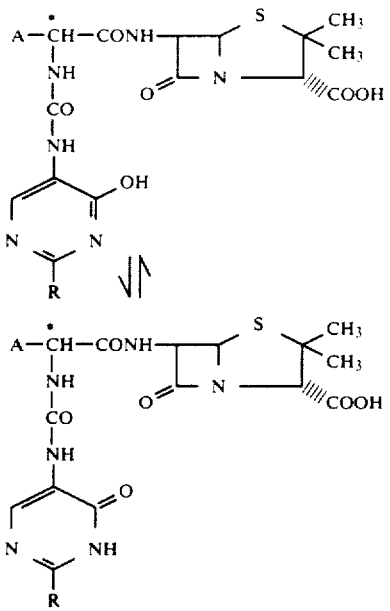

(I)

(I')

It goes without saying that the compounds of type I mentioned hereinbefore, always include both tautomers.

The compounds of the formula I may be present with regard to the chiral centre C+ in both possible R− and S-configurations, but also as a mixture of both these configurations. Especially preferred compounds are those to which the D=R-configuration applies.

The compounds of the formula I may be prepared by the following methods:

Method A

By reacting a compound of the formula

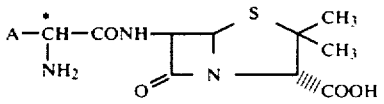

(III)

wherein A has the same meanings as in formula I, with a pyrimidine derivative of the formula

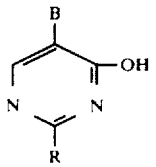

(IV)

wherein R has the same meanings as in formula I, and B represents the group —NCO or a reactive derivative of the group NHCOOH, such as for example, the groups —NHCOCl, —NHCOBr or

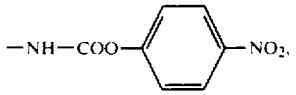

where the group NHCOCl is especially preferred. Also, mixtures of those pyrimidine derivatives of the formula IV can be used, where B has two of the above-mentioned meanings, for example the groups —NCO and

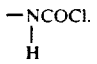

The starting compounds of the formula III can be used in the form of their inorganic or organic salts, e.g. as the triethylammonium salt or the sodium salt. The reaction can be carried out in any desired mixtures of water and these organic solvents which can be mixed with water; for instance in ketones, such as acetone; in cyclic ethers, such as tetrahydrofuran or dioxane; in nitriles, such as acetonitrile; in formamides, such as dimethylformamide; in dimethylsulfoxide; or in alcohols, such as isopropanol or in hexametapol. The pH-value of the reaction mixture is kept by addition of bases or by use of buffer solutions, within a pH-range of about 2.0 to 9.0, preferably between a pH-value 6.5 and 8.0. But it is also possible to carry out the reaction in anhydrous organic solvents, such as halogenated hydrocarbons like chloroform or methylene chloride, in the presence of a base, preferably triethylamine, diethylamine or N-ethyl-piperidine. The reaction can also be carried out in a mixture consisting of water and a solvent immiscible with water, like ethers such as diethylether; halogenated hydrocarbons such as chloroform or methylene chloride; carbon disulfide; ketones such as isobutyl methyl ketone; esters such as ethyl acetate; or aromatic solvents such as benzene; under these conditions it is advantageous to stir vigorously and to keep the pH-value, by addition of bases or by using of buffer solutions, in a range of about pH 2.0 to 9.0, preferably between 6.5 and 8.0. The reaction can also be carried out in water alone in the presence of an organic or inorganic base or by adding of buffering agents.

If silyl derivatives of the compounds of the formula III (for instance mono- or di-trimethylsilyl derivatives) are used as starting compounds for this method and they are reacted with compounds of the formula IV, it is advantageous to work in anhydrous solvents free from hydroxyl groups, for example in halogenated hydrocarbons, such as methylene chloride or chloroform, benzene, tetrahydrofuran, acetone or dimethylformamide, etc. The addition of bases is not necessary, but can be of advantage in individual cases to improve the yield and the purity of the products. As optionally added bases tertiary aliphatic or aromatic amines, such as pyridine or triethylamine, or due to steric hindrance difficulty acylatable secondary amines, such as dicyclohexylamine are used.

Instead of silyl esters all other carboxyl derivatives of α-aminobenzyl penicillins which are known in the field of preparation of semi-synthetized penicillins can also be used. Typical examples are the trityl esters, the p-nitrobenzyl esters or the phenacyl esters. Subsequent to the reactions, these derivatives can be converted into the penicillins of the present invention by known methods. The amount of bases used is fixed, for example, by the desired adherence to a certain pH-value.

Where a pH-measurement and adjustment is not carried out or is not possible or purposeful because of the lack of sufficient water in the diluting agent, preferably 1.0 to 2.0 mol equivalents of bases are used if the starting compound is a non-silylated compound of the formula II. If a silylated compound is used, preferably up to one mol equivalent of base is supplied.

In principle, all bases are used which are usually used in organic chemistry as organic or inorganic bases, such as alkali metal hydroxides and alkaline earth metal hydroxides, alkaline earth metal oxides, alkali metal carbonates and alkaline earth metal carbonates and bicarbonates, ammonia, primary, secondary and tertiary aliphatic and aromatic amines, as well as heterocyclic bases. Examples are sodium, potassium or calcium hydroxide, calcium oxide, sodium or potassium carbonate, sodium or potassium bicarbonate, ethylamine, methylethylamine, triethylamine, hydroxy ethylamine, aniline, pyridine and piperidine. When using silylated starting materials, however, the above-mentioned restrictions concerning the kind of bases should be noted.

As buffer systems all usual buffer mixtures can be used, such as phosphate buffer, citrate buffer and tris(-hydroxy-methyl)-amino methane buffer.

The reaction temperature can be varied within a wide range. In general, it is between about −20° and about +50° C., preferably between 0° and +20° C.

The reaction partners of the formula II and III can be reacted with each other in equimolar amounts. However, in individual cases it can be of advantage to use one of the two reaction partners in excess, in order to facilitate the purification of the end product or to increase the yield.

Method B

By reacting a ureido-carboxylic acid of the formula

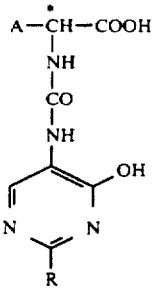

(V)

wherein A and R have the same meanings as in formula I, or a salt or reactive derivative thereof, with 6-aminopenicillanic acid of the formula

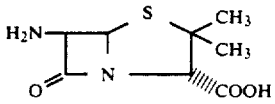

(VI)

or with an inorganic or organic salt or derivative thereof which is easily convertible into 6-aminopenicillanic acid. The reaction product obtained is optionally subsequently hydrolyzed or catalytically hydrogenated into a penicillin or the formula I.

Suitable reactive derivatives of the ureido-carboxylic acids of the formula V are, for example, acid anhydrides, such as those which derive from chloroformates, for instance ethyl chloroformate or isobutyl chloroformate, or their reactive esters such as the p-nitrophenyl ester or the N-hydroxysuccinimid ester, or their reactive amides such as the N-carbonylimidazole, or also their acid halides such as the corresponding acid chloride, or their acid azides. In principle, however, all reaction methods can be used which are known from the $\beta$-lactam chemistry.

The 6-amino-penicillanic acid is advantageously used in the form of one of its derivatives. Suitable derivatives thereof are, for example the trimethylsilyl ester, the trityl ester, the p-nitrobenzylester, the phenacyl ester and the O,N-bis-trimethylsilyl derivative. These derivatives are reacted preferably in an aprotic solvent like methylene chloride or tetrahydrofuran. But the 6-amino-penicillanic acid can also be used in the form of its salts, for example its triethylammonium salt; in that case methylene chloride or a protic solvent or an aqueous medium or an aqueous-organic solvent, such as tetrahydrofuran-water mixtures, are used.

The ureido-carboxylic acid, its salts or its reactive derivatives are reacted with the 6-amino-penicillanic acid or its derivatives in a solvent at temperatures between $-40°$ and $+40°$ C., optionally in the presence of a base. If, for example, an anhydride of the ureido-carboxylic acid such as the anhydride with ethylchloroformate, is reacted with a derivative of the 6-aminopenicillanic acid, the reaction is carried out while cooling, for example at temperatures between $-10°$ and $+10°$ C., in the presence of a tertiary amine such as triethylamine or N,N-dimethylaniline, in a solvent such as acetone, tetrahydrofuran, dimethylformamide, chloroform, dichloromethane, hexametapol or a mixture of these solvents. If, for example, an N-hydroxy-succinimid ester of the ureido-carboxylic acid is reacted with 6-amino-penicillanic acid, the reaction is preferably carried out at temperatures between 0° and 20° C. in the presence of a base such as triethylamine, in a solvent like dimethylformamide, dichloromethane, dioxane or a mixture of such solvents.

The reaction of a ureido-carboxylic acid of the formula IV itself or a salt thereof with 6-amino-penicillanic acid or its salts is carried out advantageously in the presence of a condensation agent such as N,N'-dicyclohexlcarbodiimide.

If a derivative of 6-amino-penicillanic acid is used, for example one of the above-mentioned esters, a reaction product can be obtained which, for example, still contains the ester function, depending on the reaction conditions. Such a reaction product is easily convertible into a penicillin of the formula I. If, for example, the carboxylic group of the 6-amino-penicillanic acid is present in the form of a silyl ester, this group can also be present after the reaction in the obtained penicillin of the formula I in the form of the silyl ester. In this case, subsequent to the actual reaction, this silyl ester group is hydrolyzed off, whereby the corresponding compound of the formula I results. In other cases, for example if a p-nitrobenzyl ester is present, this p-nitrobenzyl ester group is split off by hydrogenation after the actual reaction, whereby the corresponding penicillin of the formula I is obtained.

Further processing of the reaction mixtures resulting from methods A and B is carried out according to methodswhich are conventional for $\beta$-lactam-antibiotics; the same is the case for the isolation and purification of the end products, for example for liberating the acid from its salts and converting the free acid in other salts with inorganic or organic bases. For the preparation of the potassium or sodium salts, particularly the precipitation of these salts from an alcoholic-ethereal solution of the free acid by adding of potassium- or sodium-2-ethylhexanoate is suitable.

The starting compounds of the formula III are known from the literature; see, for example, E. H. Flynn, Cephalosporin and Penicillins, Academic Press, New York and London (1972).

The starting compounds of the formula IV can be obtained, for example, by reaction of the corresponding 5-amino-pyrimidines of the formula

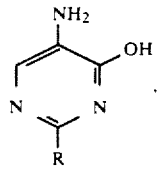

(VII)

wherein R has the same meanings as in formula I, with phosgene. This reaction is preferably carried out in a solvent not containing hydroxyl groups, such as tetrahydrofuran, methylene chloride, chloroform, dimethoxyethane or hexametapol, at temperatures between $-40°$ and $+60°$ C., preferably between $-10°$ and $+20°$ C., where it is advisable to bind the resulting hydrogen chloride by equimolar amounts of an inert organic base like triethylamine or pyridine. An excess of pyridine can also be used as the solvent. If the corresponding aminopyrimidines of the formula VII are difficultly soluble in one of the mentioned solvents, the phosgenation can also be carried out in a heterogeneous phase. Furthermore, the aminopyrimidines of the formula VII can, by treatment with a silylating agent like hexamethyldisilazane or trimethyl-chlorosilane/triethylamine, be converted into a mono- or, depending upon the number of exchangeable hydrogen atoms, multi-silylated aminopyrimidine which is easily soluble in the above-mentioned solvents. The thus obtained aminopyrimidine is reacted with phosgene into the corresponding compound of the formula IV. Depending on the kind of the solvent, the height of the temperature, the amount and the kind of the base used, either mainly the corresponding isocyanate or carbamic acid halide or a mixture of these two compounds is obtained. Depending on the reaction conditions, the compound of the formula IV can also be present, slightly or partly as an isocyanate isomer, that is, as a tetrahydro-oxazolo-pyrimidine of the formula

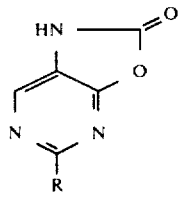

(IVa)

The starting compounds of the formula IV or their mixtures obtained by phosgenation are, in general, readily soluble in the above-mentioned solvents, and after removal of the excess phosgene, they can be reacted directly without further purification with the corresponding penicillin derivatives of the formula III.

2-Substituted 5-amino-4-hydroxy-pyrimidines of the formula VII are sparsely described in the literature; for example, for

| | |
|---|---|
| R | = hydrogen: J. Chem. Soc. 1952, 4942; |
| | = ethylthio: J. Chem. Soc. 1952, 4942; |
| | = hydroxy: J. Am. Chem. Soc. 46, 702(1924); |
| | = dimethylamino: J. Chem. Soc. 1956, 3232. |

For the preparation of pyrimidines of the formula VII therefore, several processes were developed, of which the most important ones are indicated below, where, depending upon the meaning of R, the most favorable method should be used for the synthesis of compound VII.

(a) Reaction of ethyl-carbethoxyamino-formyl acetate sodium salt of the formula VIII with compounds of the formula IX, wherein R has the meanings previously defined, and subsequent alkaline hydrolysis, pursuant to the reaction sequence:

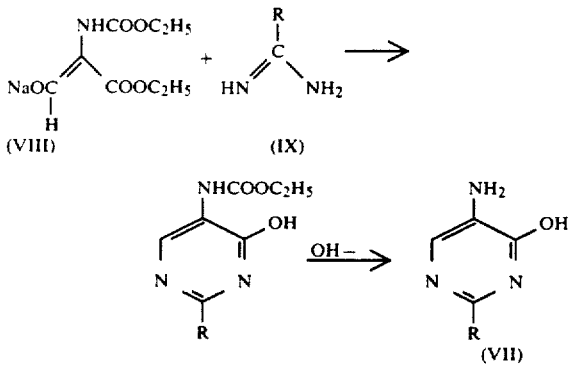

(b) Reaction of ethyl ethoxymethylene-nitroacetate of the formula X with compounds of the formula IX and subsequent reduction of the nitro group according to known methods pursuant to the reaction sequence.

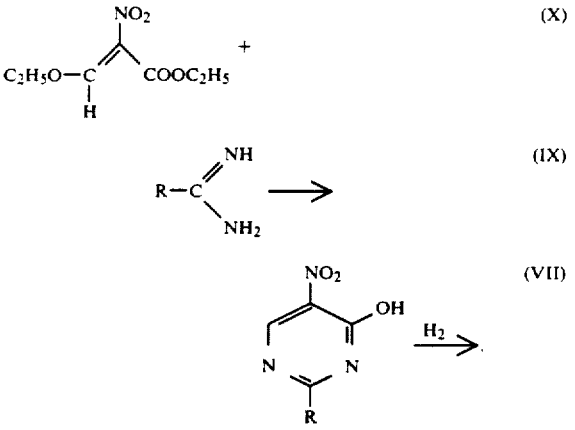

(c) Reaction of 2-phenyl-4-ethoxymethylene-5-oxo-2-oxazoline of the formula XI with compounds of the formula IX and subsequent acid or alkaline hydrolysis (see also Clarke, Johnson and Robinson. The Chemistry of Penicillins, Princeton University Press 1949, page 803).

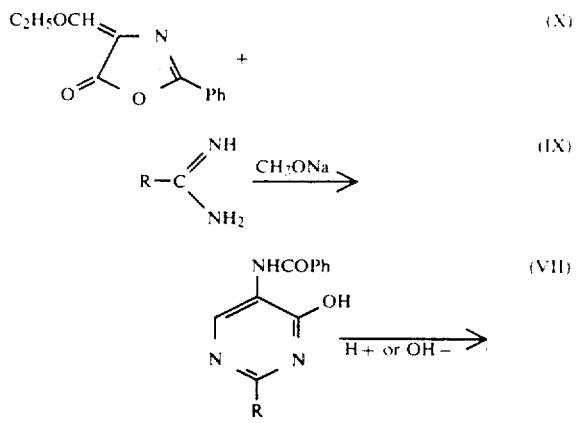

(d) Acylation of 2-amino-4-hydroxy-5-nitropyrimidines of the formula XII and subsequent reduction

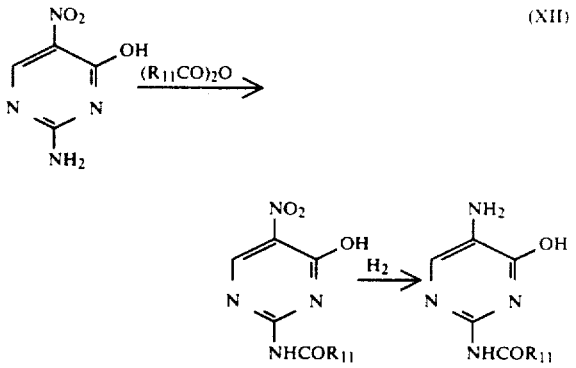

By this method compounds of the formula VII are obtained where R represents the group—$NHCOR_{11}$.

(e) Reaction of 2-methylmercapto-4-hydroxy-5-nitropyrimidines of the formula XIIIa [literature reference: Vorbrüggen and Strehlke, Chem. Ber. 106, p. 3039 (1973)] or of 5-benzoylamino-4-hydroxy-2-methylmercapto-pyrimidines of the formula XIIIb (or its derivatives oxidized at the sulfur atom) with substituted amines, and subsequent reduction or hydrolysis:

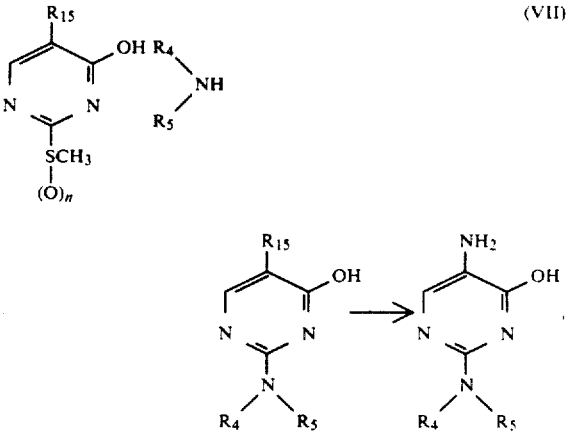

(n = 0, 1 or 2)
XIIIa $R_{15}$ = $NO_2$
XIIIb $R_{15}$ = $NHCOC_6H_5$

By this method compounds of the formula VII are obtained, where R represents the group —$NR_4R_5$.

In order to characterize the thus obtained starting compounds of the formula VII the following typical representatives should be mentioned.

5-Amino-2-methyl-4-hydroxy-pyrimidine
5-Amino-2-ethyl-4-hydroxy-pyrimidine
5-Amino-2-isopropyl-4-hydroxy-pyrimidine
5-Amino-2-allyl-4-hydroxy-pyrimidine
5-Amino-2-propargyl-4-hydroxy-pyrimidine
5-Amino-2-cyclopropyl-4-hydroxy-pyrimidine
5-Amino-2-(1'-methyl)-cyclopropyl-4-hydroxy-pyrimidine
5-Amino-2-(2'-methyl)-cyclopropyl-4-hydroxy-pyrimidine
5-Amino-2-cyclobutyl-4-hydroxy-pyrimidine
5-Amino-2-cyclohexyl-4-hydroxy-pyrimidine
5-Amino-2-benzyl-4-hydroxy-pyrimidine
5-Amino-2-(p-chlorobenzyl)-4-hydroxy-pyrimidine
5-Amino-2-(m-chlorobenzyl)-4-hydroxy-pyrimidine
5-Amino-2-(o-chlorobenzyl)-4-hydroxy-pyrimidine
5-Amino-2-(p-fluorobenzyl)-4-hydroxy-pyrimidine
5-Amino-2-(p-hydroxybenzyl)-4-hydroxy-pyrimidine
5-Amino-2-(p-acetylbenzyl)-4-hydroxy-pyrimidine
5-Amino-2-(p-nitrobenzyl)-4-hydroxy-pyrimidine
5-Amino-2-(p-dimethylaminobenzyl)-4-hydroxy-pyrimidine
5-Amino-2-(p-methylbenzyl)-4-hydroxy-pyrimidine
5-Amino-2-(o,p-dichlorobenzyl)-4-hydroxy-pyrimidine
5-Amino-2-(m,p-dichlorobenzyl)-4-hydroxy-pyrimidine
5-Amino-2-(p-amino-m,m-dichlorobenzyl)-4-hydroxy-pyrimidine
5-Amino-2-phenyl-4-hydroxy-pyrimidine
5-Amino-2-(p-chlorophenyl)-4-hydroxy-pyrimidine
5-Amino-2-(m-trifluoromethyl-phenyl)-4-hydroxy-pyrimidine 5-Amino-2-(p-methoxyphenyl)-4-hydroxy-pyrimidine
5-Amino-2-(p-dimethylamino-phenyl)-4-hydroxy-pyrimidine
5-Amino-2-(m-chlorophenyl)-4-hydroxy-pyrimidine
5-Amino-2-(p-amino-m,m-dichlorophenyl)-4-hydroxy-pyrimidine
5-Amino-2-(1'-phenylethyl)-4-hydroxy-pyrimidine
5-Amino-2-cyclopropylmethyl-4-hydroxy-pyrimidine
5-Amino-2,4-dihydroxy-pyrimidine
5-Amino-2-methoxy-4-hydroxy-pyrimidine
2,5-Diamino-4-hydroxy-pyrimidine
5-Amino-2-ethoxy-4-hydroxy-pyrimidine
5-Amino-2-methylamino-4-hydroxy-pyrimidine
5-Amino-2-dimethylamino-4-hydroxy-pyrimidine
5-Amino-2-ethylamino-4-hydroxy-pyrimidine
5-Amino-2-diethylamino-4-hydroxy-pyrimidine
5-Amino-2-propylamino-4-hydroxy-pyrimidine
5-Amino-2-isopropylamino-4-hydroxy-pyrimidine
5-Amino-2-butylamino-4-hydroxy-pyrimidine
5-Amino-2-hexylamino-4-hydroxy-pyrimidine
5-Amino-2-allylamino-4-hydroxy-pyrimidine
5-Amino-2-propargylamino-4-hydroxy-pyrimidine
5-Amino-2-cyclopropylamino-4-hydroxy-pyrimidine
5-Amino-2-cyclobutylamino-4-hydroxy-pyrimidine
5-Amino-2-cyclohexylamino-4-hydroxy-pyrimidine
5-Amino-2-cycloheptylamino-4-hydroxy-pyrimidine
5-Amino-2-(1'-methyl)-cyclopropylamino-4-hydroxy-pyrimidine
5-Amino-2-cyclopropylmethylamino-4-hydroxy-pyrimidine
5-Amino-2-(N-methyl)-N-cyclohexylamino-4-hydroxy-pyrimidine
5-Amino-2-pyrrolidino-4-hydroxy-pyrimidine
5-Amino-2-piperidino-4-hydroxy-pyrimidine
5-Amino-2-morpholino-4-hydroxy-pyrimidine
5-Amino-2-piperazino-4-hydroxy-pyrimidine
5-Amino-2-(N-formyl)-piperazino-4-hydroxy-pyrimidine
5-Amino-2-(N-ethoxycarbonyl)-piperazino-4-hydroxy-pyrimidine
5-Amino-2-(N-acetyl)-piperazino-4-hydroxy-pyrimidine
5-Amino-2-(N-phenyl)-piperazino-4-hydroxy-pyrimidine
5-Amino-2-anilino-4-hydroxy-pyrimidine
5-Amino-2-p-chloroanilino-4-hydroxy-pyrimidine
5-Amino-2-p-dimethylaminoanilino-4-hydroxy-pyrimidine
5-Amino-2-o-chloroanilino-4-hydroxy-pyrimidine
5-Amino-2-m,p-dichloroanilino-4-hydroxy-pyrimidine
5-Amino-2-p-hydroxyanilino-4-hydroxy-pyrimidine
5-Amino-2-p-methylanilino-4-hydroxy-pyrimidine
5-Amino-2-p-acetylamino-anilino-4-hydroxy-pyrimidine
2-Amino-2-p-fluoroanilino-4-hydroxy-pyrimidine
5-Amino-2-m-chloroanilino-4-hydroxy-pyrimidine
5-Amino-2-p-bromoanilino-4-hydroxy-pyrimidine
5-Amino-2-(p-chloro-m-trifluoromethyl)-anilino-4-hydroxy-pyrimidine
5-Amino-2-trifluoromethylanilino-4-hydroxy-pyrimidine
5-Amino-2-p-hydroxyanilino-4-hydroxy-pyrimidine
5-Amino-2-benzylamino-4-hydroxy-pyrimidine
5-Amino-2-p-chlorobenzylamino-4-hydroxy-pyrimidine
5-Amino-2-(N-methyl)-anilino-4-hydroxy-pyrimidine
5-Amino-2-(N-methyl)-p-chloroanilino-4-hydroxy-pyrimidine
5-Amino-2-formylamino-4-hydroxy-pyrimidine
5-Amino-2-acetylamino-4-hydroxy-pyrimidine
5-Amino-2-propionylamino-4-hydroxy-pyrimidine
5-Amino-2-isobutyrylamino-4-hydroxy-pyrimidine
5-Amino-2-butyrylamino-4-hydroxy-pyrimidine
5-Amino-2-cyclopropionylamino-4-hydroxy-pyrimidine
5-Amino-2-cyclohexanoylamino-4-hydroxy-pyrimidine
5-Amino-2-benzoylamino-4-hydroxy-pyrimidine
5-Amino-2-p-chlorobenzoylamino-4-hydroxy-pyrimidine
5-Amino-2-trifluoroacetylamino-4-hydroxy-pyrimidine
5-Amino-2-pentafluoropropionylamino-4-hydroxy-pyrimidine
5-Amino-2-heptafluorobutyrylamino-4-hydroxy-pyrimidine
5-Amino-2-ethoxycarbonylamino-4-hydroxy-pyrimidine
5-Amino-2-ureido-4-hydroxy-pyrimidine
5-Amino-2-(3'methyl)-ureido-4-hydroxy-pyrimidine
5-Amino-2-(3'-dimethyl)-ureido-4-hydroxy-pyrimidine
5-Amino-2-pyrrolidinocarbonylamino-4-hydroxy-pyrimidine
5-Amino-2-(3'-phenyl)-ureido-4-hydroxy-pyrimidine 5-Amino-2-methylsulfonylamino-4-hydroxy-pyrimidine 5-Amino-2-toluenesulfonylamino-4-hydroxy-pyrimidine 5-Amino-2-mercapto-4-hydroxy-pyrimidine 5-Amino-2-methylmercapto-4-hydroxy-pyrimidine 5-Amino-2-ethylmercapto-4-hydroxy-pyrimidine 5-Amino-2-p-chlorophenylmercapto-4-hydroxy-pyrimidine 5-Amino-2-methylsulfinyl-4-hydroxy-pyrimidine 5-Amino-2-ethylsulfinyl-4-hydroxy-pyrimidine The ureido-carboxylic acids of the formula V can be easily obtained by reaction of the pyrimidine derivatives of the formula IV with glycine derivatives of the formula

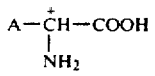

(XIV)

wherein A has the meanings previously defined. The reaction is carried out at temperatures between −20° and +40° C., preferably between 0°and +20° C. in a solvent. As solvents can be used, for example, mixtures of water and watermiscible organic solvents, such as acetone, tetrahydrofuran, dioxane, acetonitrile, dimethylformamide, ethanol or dimethylsulfoxide. In some instances the use of a halogen hydride-binding agent is necessary. As such agents, for example, trialkylamines such as triethylamine or inorganic bases such as dilute sodium hydroxide solution are suitable The following examples illustrate the present invention and will enable others skilled in the art to understand it more completely. It should be understood, However, that the invention is not limited solely to the particular examples given below.

The $R_f$ values refer to the system n-butanol-waterglacial acetic acid=60:25:15, $SiO_2$-plate. "Ampicillin" means α-aminobenzylpenicillin, "amoxycillin" means α-amino-p-hydroxy-benzylpenicillin and "epicillin" means α-amino- α-(1,4-cyclohexadien-1-yl)-methylpenicillin, each with the D=R-configuration in the side chain.

1. PREPARATION OF THE STARTING MATERIALS

EXAMPLE A

5-Amino-2-p-chlorobenzyl-4-hydroxy-pyrimidine 27.1 gm of p-chlorobenzylamidine hydrochloride (0.132 mol) are stirred for 1 hour with ice cooling in a solution of 3.03 gm of sodium in 200 ml of absolute ethanol. The common salt is subsequently separated off. 30 gm (0.13 mol) of ethylcarbethoxyamino-formyl acetate sodium salt (for preparation see M. Boarland and Mc. Omie, J. Chem. Soc. 1952, page 4942) are added thereto. The mixture is stirred for 3 hours at 0° C. and 3 hours at room temperature and subsequently evaporated to dryness in vacuo. The residue is taken up in dilute sodium hydroxide solution and mixed with concentrated hydrochloric acid until a pH value of 5.0 is obtained. The precipitated product is extracted, by filtration washed with water and dissolved in 80 ml of water with 12 gm of sodium hydroxide solution. The solution is refluxed for 30 minutes. It is thereafter cooled, acidified with acetic acid and the precipitated product is extracted.

Yield: 13 gm (42.5%).

M.p.: 245° C. from ethanol.

Calculated: C,53.80; H,4.49; N,18.76. Found: C,53.03; H,4.51; N,18.32.

The pyrimidines listed in the following table were synthesized according to this method:

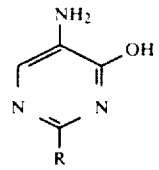

| R | Yield in % | Melting Point |
|---|---|---|
| $C_2H_5$ | 44 | 189° C. |
| $CH(CH_3)_2$ | 31 | 202° C. |
| $C(CH_3)_3$ | 39 | 218° C. |
| $C_5H_{11}$ | 46 | 200° C. |
| $C_8H_{17}$ | 23 | sinters >130° C. |
| Cyclobutyl | 41 | 208°-210° C. |
| Cyclopentyl | 52 | 235° C. |
| Cyclohexyl | 58 | 230°-231° C. |
| $CH_2—CH_2—C_6H_5$ | 54 | 193°-195° C. |
| $(CH_2)_3—C_6H_5$ | 48 | 176° C. |
| $—CH(CH_3)—C_6H_5$ | 44 | 197°-199° C. |
| $—CH=CH—C_6H_5$ | 36 | 115°-118° C. |

or

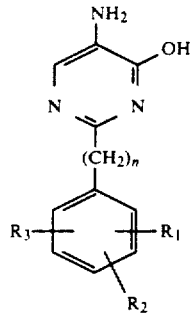

| | n | $R_1$, $R_2$, $R_3$ | Yield in % | Melting Point |
|---|---|---|---|---|
| (b) | 1 | p-Fluoro | 41 | 242° C. |
| (c) | 1 | Hydrogen | 47 | 202°-204° C. |
| (d) | 1 | o,o'Dichloro | 31 | 252°-255° C. |
| (e) | 0 | p-Hydroxy | 34 | 210°-215° C. (decomp.) |
| (f) | 0 | p-dimethylamino | 40 | 250° C. (decomp.) |
| (g) | 1 | o-Methoxy | 51 | 247°-250° C. |
| (h) | 1 | p-ethoxy | 54 | 265°-268° C. (decomp.) |
| (i) | 1 | p-Nitro | 46 | >300° C. |
| (k) | 1 | $p-CH_3—CO$ | 29 | 250°-251° C. |
| (l) | 0 | p-Methylamino | 24 | 232°-235° C. (decomp.) |
| (m) | 0 | o-Chloro | 42 | 243°-245° C. |
| (n) | 1 | p-methylmercapto | 38 | 242°-244° C. (decomp.) |
| (o) | 1 | p-Methylsulphoxy | 37 | 265°-267° C. (decomp.) |
| (p) | 1 | p-Methoxy | 58 | 228° C. |

EXAMPLE B (a) 5-Amino-4-hydroxy-2-phenyl-pyrimidine 20 gm (0.089 mol) of ethylcarbethoxyamino-formyl acetate sodium salt are dissolved at room temperature in 40 ml of water. Added thereto is a solution which has been prepared from 16.7 gm (0.09 mol) benzamidine hydrochloride and 3.6 gm (0.09 mol) of sodium hydroxide solution in 15 ml of water. The mixture is stirred overnight at room temperature and subsequently refluxed for 1 hour. Concentrated hydrochloric acid is then added thereto with cooling, so that the pH value is approximately 5.5. The precipitated product is extracted and washed with water.

This compound is refluxed crude for half an hour with a solution of 8 gm of sodium hydroxide solution in 50 ml of water. It is allowed to cool and concentrated hydrochloric acid is carefully added thereto until a pH value of 5.0 is obtained. The precipitated product is extracted, washed with a little water and dried.

Yield: 11.4 gm (67%).

M.p.: 220° C. (decomposition).

Calculated: C, 64.16; H, 4.85; N, 22.45. Found: C, 63.92; H, 4.79; N, 22.69.

The following pyrimidines were synthesized according to this method:

| | n | $R_1$, $R_2$, $R_3$ | Yield | Melting Point |
|---|---|---|---|---|
| (b) | 1 | m-Chloro | 39 | 220° C. (decomp.) |
| (c) | 1 | p-Bromo | 53 | 232° C. |
| (d) | 1 | m,p-Dichloro | 48 | 245°-250° C. |
| (e) | 0 | p-methoxy | 40 | 221° C. |
| (f) | 0 | p-$CONH_2$ | 28 | 189°-190° C. |
| (g) | 1 | m,p-dimethoxy | 58 | 230°-235° C. |
| (h) | 0 | m-Trifluoromethyl | 31 | 202° C. |
| (i) | 0 | p-Chloro | 42 | 195°-197° C. |
| (k) | 0 | m-Methyl | 27 | 191° C. |
| (l) | 0 | m-Chloro | 51 | 214°-216° C. |
| (m) | 1 | m,m,p-Trimethoxy | 54 | 234°-238° C. |
| (n) | 1 | o,p-Dichloro | 48 | 245°-248° C. |
| (o) | 1 | p-Dimethylamino | 35 | 251° C. (decomp.) |
| (p) | 1 | m,m'-Dichloro p-amino | 18 | 189°-192° C. (decomp.) |
| (q) | 1 | p-Cyano | 47 | 227° C. (decomp.) |

EXAMPLE C

If the p-chlorobenzylamidine hydrochloride of Example A is replaced by the corresponding S- or O-alkylisothiourea, then the pyrimidines of the following table are obtained:

| R | Yield | Melting Point |
|---|---|---|
| $CH_3O$— | 32 | 140° C. (decomp.) |
| $C_2H_5O$ | 38 | 155° C. (decomp.) |
| —O—$C_6H_5$ | 64 | 206° C. (decomp.) |
| $C_2H_5S$ | 71 | 166° C. |
| 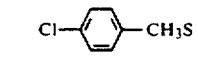 | 26 | 141°-145° C. (decomp.) |

EXAMPLE D (a) 5-Amino-2-cyclopropyl-4-hydroxy-pyrimidine 120 gm of 2-phenyl-4-ethoxymethylene-5-oxo-2-oxaline (0.55 mol), 71 gm of cyclopropylformamidinehydrochloride (0.59 mol) and 98 gm of sodium acetate are refluxed for 3 hours in 3 liters of absolute ethanol. The mixture is subsequently evaporated in vacuo to 1.2 liters and poured into 5 liters of ice water. The precipitated product is extracted and recrystallized from glacial acetic acid.

M.p. 258° C.

Yield: 118 gm (84%).

(b) 90 gm (0.35 mol) of the product thus prepared are refluxed for 2 hours with 140 gm of sodium hydroxide solution and 560 ml of water. The mixture is cooled and acidified with concentrated hydrochloric acid to pH 1.5 with cooling. The precipitated benzoic acid is taken up in ether. The aqueous phase is brought to pH 6.5 and evaporated to dryness. The desired product is extracted with tetrahydrofurane.

Yield: 44 gm (83%).

M.p.: 206° C.

The following pyrimidines are synthesized according to this method:

| R | Yield | Melting Point |
|---|---|---|
| 2-Methyl-cyclopropyl | 64% | 192°-195° C. |
| 1-Methyl-cyclopropyl | 56% | 186° C. |
| Allyl | 36% | 174°-175° C. |
| Propargyl | 31% | 177°-180° C. |
| Crotyl | 38% | 154°-155° C. |
| Cyclopropylmethyl | 51% | 216° C. |
| 2-Phenyl-cyclopropyl | 64% | 248°-250° C. |
| Cyclohexen-(2)-yl | 46% | 189°-190° C. |

If the amidine is replaced by corresponding guanidines and the benzoyl group is split off refluxing with 5 N hydrochloric acid, then the following pyrimidines are obtained

| | | |
|---|---|---|
| Pyrrolidino | 64 | Decomposition from 230° C. |
| Hexahydroazepino | 51 | Decomposition from 218°-220° C. |
| Diethylamino | 56 | 211°-212° C. |

EXAMPLE E 1.4-Hydroxy-2-methylmercapto-5-nitro-pyrimidine 104.5 gm of S-methyl-isothiourea (0.75 mol) and 53.3 gm (1.333 mol) of sodium hydroxide solution are stirred together for 10 minutes in 350 ml of water. 114.5 gm (0.605 mol) of ethyl-ethoxymethylene-nitroacetate are then slowly added thereto, the temperature being kept at 20° C. by cooling. The precipitate is extracted and washed with a little ice-cold water. It is dissolved in approximately 9 liters of hot water and acidified with concentrated hydrochloric acid with cooling. The precipitated product is extracted and washed with ether.

Yield: 65 gm (58%).

M.p.: 220°-222° C.

2.2-Anilino-4-hydroxy-5-nitro-pyrimidine 4.65 gm of 4-hydroxy-2-methylmercapto-5-nitropyrimidine (0.025 mol) are dissolved with heating in 150 ml of ethanol and refluxed for 5 hours with 4.68 gm of aniline (0.05 mol). The precipitated product is extracted in the cold, washed with ethanol and dried.

Yield: 4.1 gm (70%).

M.p.: >300° C.

Calculated: C, 51.73; H, 3.47; N, 24.13. Found: C, 51.70; H, 3.39; N, 23.95.

3.5-Amino-2-anilino-4-hydroxy-pyrimidine 2.3 gm of the nitro compound (0.01 mol) of Example 2 are hydrogenated in 100 ml of dimethyl formamide with 500 mg of Raney-nickel until absorption of hydrogen is completed. The catalyst is separated, the solvent is evaporated in vacuo and a little ethanol is added. The precipitated crystalline product is extracted and dried.

Yield: 1.1 gm (55%)

M.p.: 240°-242° C.

Calculated: C, 59.40; H, 4.98; N, 27.71. Found: C, 58.70; H, 5.08; N, 27.10.

The following pyrimidines of the general formula were synthesized analogously:

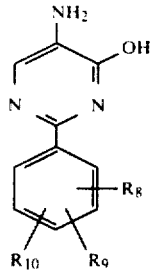

| $R_8$, $R_9$, $R_{10}$ | Melting Point | Yield |
|---|---|---|
| p-Chloro | 240°-242° C. | 44% |
| p-methoxy | 220°-222° C. | 61% |
| p-hydroxy | 290°-293° C. | 37% |
| m,p-dichloro | 280° C. | 47% |
| p-methyl | 212°-215° C. | 34% |
| p-acetylamino | 255°-256° C. | 51% |
| o-chloro | 219°-220° C. | 42% |
| p-fluoro | 238°-240° C. | 54% |
| m-chloro | 241°-242° C. | 46% |
| o,p-dichloro | 264°-265° C. | 40% |
| p-dimethylamino | 264°-265° C. | 48% |
| p-nitro | >300° C. | 34% |
| m-trifluoromethyl-p-chloro | 283°-285° C. | 61% |
| o-methyl | 220°-222° C. | 31% |
| p-bromo | 235°-236° C. | 44% |
| m,m'-dichloro-p-amino | 275° C. (decomp.) | 38% |

By reaction of 4-hydroxy-2-methylmercapto-5-nitropyrimidine with aliphatic or araliphatic amines and subsequent reduction of the nitro group the following pyrimidines were obtained:

| R | Yield | Melting Point |
|---|---|---|
| $CH_2{=}CH{-}CH_2NH$ | 43% | sinters from 80° C. |
| $CH_3{-}CH{=}CH{-}CH_2NH$ | 39% | decomp. 114° C. |
| $HC{\equiv}C{-}CH_2NH$ | 48.5% | 186°-187° C. |
| $(CH_2{=}CH{-}CH_2)_2N$ | 53% | 139°-140° C. |
| Cyclopropylamino | 58% | 246° C. |
| Cyclobutylamino | 41% | 261° C. |
| Cyclopentylamino | 52% | 270° C. |
| Cyclohexylamino | 41% | sinters from 170° C. |
| Dimethylamino | 58% | 225° C. |
| Formylpiperazino | 21% | 246°-249° C. |
| Acetylpiperazino | 27% | 255°-260° C. (decomp.) |
| Carbethoxypiperazino | 38% | 205° C. |
| Benzyloxycarbonylpiperazino | 44% | sinters from 180° C. |
| Phenylpiperazino | 46.5% | 264°-265° C. |
| Methylpiperazino | 42% | 176°-180° C. |
| Morpholino | 59% | 175°-185° C. |
| Thiomorpholino | 46% | 183°-186° C. |
| Thiomorpholino-s-oxide | 37% | >300° C. |
| Thiomorpholino-S,S—dioxide | 34% | >300° C. |
| Methylamino | 52% | 196°-198° C. |
| Phenethylamino | 55% | 89°-90° C. |
| Benzylamino | 40% | sinters from 140° C. |
| p-Chlorobenzylamino | 39% | sinters from 90° C. |
| l-Phenylethylamino | 46% | 166°-169° C. |

EXAMPLE F

5-Benzoylamino-4-hydroxy-2-methylmercapto-pyrimidine 120 gm of 2-phenyl-4-ethoxymethylene-5-oxo-2-oxaline (0.55 mol) are refluxed for 6 hours together with 115 gm of S-methyl-isothiourea sulphate and 99 gm of sodium acetate in 2 liters of absolute ethanol. Ethanol is drawn off in vacuo and the residue is stirred in 3 liters of ice water. It is extracted and recrystallized from 1.2 liters of glacial acetic acid.

Yield: 87 gm (60%)

Melting Point: 270° C.

5-Amino-2-cyclohexylmethylamino-4-hydroxy-pyrimidine

A mixture of 10.2 gm of cyclohexylmethylamine (0.09 mol) and 5.4 gm of glacial acetic acid (0.09 mol) is melted at 180° C. for 1 hour with 7.8 gm of the above compound. The residue is triturated with 50% ethanol and extracted.

Yield: 8.6 gm (88%).

The product obtained is refluxed for 1 hour in 100 ml of concentrated hydrochloric acid, the precipitated benzoic acid is removed with ether and the residue is brought with concentrated sodium hydroxide solution to pH 6.5 with cooling. The product obtained is extracted.

Yield: 4.8 gm (84%).

Melting point: decomposition >90° C.

In the case of R=substituted anilino, separation of the benzoyl group is effected more conveniently with a mixture of concentrated sulphuric acid and glacial acetic acid.

The following pyrimidines were prepared according to this method:

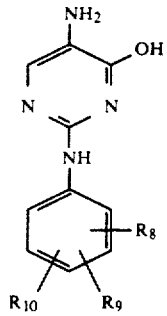

| $R_8$, $R_9$, $R_{10}$ | Yield | Melting Point |
|---|---|---|
| p-$CF_3$ | 51% | 214° C. |
| p-$C_2H_5$ | 61% | 224°-225° C. |
| p-$CH(CH_3)_2$ | 54% | 200°-202° C. |
| p-$CH_3NH$ | 46% | 244°-245° C. |
| p-$CH_3SO_2$ | 54% | 288°-290° C. |
| p-$CH_3CO$ | 67% | >300° C. |
| p-$H_2NCO$ | 61% | 279°-280° C. |
| p-CN | 44% | 246°-250° C. |
| m,p-$CH_3O$ | 54% | 234°-235° C. |
| m,m-Cl | 42% | 280°-282° C. |
| p-$CH_3SO$ | 51% | 259°-260° C. |

or

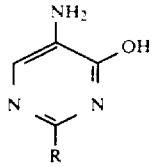

| R | Yield | Melting Point |
|---|---|---|
| 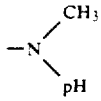 | 64% | 192°-193° C. |
| Ethylamino | 41% | decomp. >150° C. |
| Propylamino | 56% | 141°-144° C. |
| Isopropylamino | 52% | 138°-140° C. |
| Butylamino | 34% | 146°-148° C. |
| Isobutylamino | 48% | 162°-163° C. |
| Hexylamino | 58% | sinters over 115° C. |
| Octylamino | 37% | sinters over 100° C. |
| Hexahydroazepinylamino | 33% | 193°-196° C. |
| Cyclopenten-2-ylamino | 33% | 176°-178° C. |
| Cyclohexen-3-ylamino | 42% | 184°-185° C. |
| 4-Methyl-cyclohexylamino | 61% | sinters >120° C. |
| N—cyclohexyl-N—methylamino | 62% | 181°-182° C. |
| N—cyclopropyl-N—methylamino | 48% | 144°-146° C. |
| Cyclopropylmethylamino | 47% | 164°-167° C. |
| 2-cyclohexylethylamino | 64% | 204°-206° C. |

EXAMPLE G

5-Amino-4-hydroxy-2-propionylamino-pyrimidine 7.8 gm (0.055 mol) of 2-amino-4-hydroxy-5-nitropyrimidine are heated for 4 hours to 140° C. in 50 ml of propionic acid anhydride. The mixture is cooled and the precipitated product is extracted and washed with ether. The compound is suspended in 200 ml of dimethyl formamide and hydrogenated at room temperature and normal pressure with 1 gm of Pd/C as catalyst.

Yield: 6.8 gm (71%); decomposition >240° C.

The following pyrimidines were prepared according to this method:

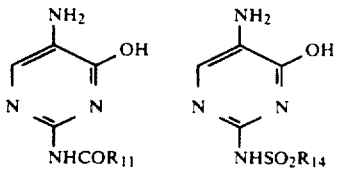

| $R_{11}$ | Yield | Melting Point |
|---|---|---|
| Propyl | 69% | 202° C. |
| Isopropyl | 74% | 214° C. |
| Butyl | 81% | 237° C. |
| Trifluoromethyl | 32% | decomp. 110° C. |
| Pentafluoroethyl | 31% | decomp. 90° C. |
| Heptafluoropropyl | 43% | decomp. 105° C. |

If an acid chloride or an isocyanate is used as acylating agent in this method, the reaction is effected in dry pyridine as solvent. Reduction of the acylated nitro compound obtained is effected analogously to above Examples.

The following pyrimidines can thus be synthesized:

| | Yield | Melting Point |
|---|---|---|
| $R_{11}$ | | |
| Cyclopropyl | 46% | decomp. 160° C. |
| Cyclohexyl | 42% | 247-248° C. |
| Phenyl | 61% | 218-220° C. |
| Ethoxy | 32% | 244-245° C. |
| Dimethylamino | 28% | 251-254° C. |
| Methylamino | 47% | 196° C. |
| Cyclopropylamino | 41% | 185° C. |
| Amino | 22% | 220-225° C. |
| Anilino | 47% | 264-265° C. |
| Pyrrolidino | 39% | 214-215° C. |
| or | | |
| $R_{14}$ | | |
| Methyl- | 34% | 151-152° C. |
| Ethyl- | 31% | 164-168° C. |
| Tolyl- | 56% | 166-170° C. |

EXAMPLE H

D-α-[3-(2-p-fluorobenzyl-4-hydroxy-5-pyrimidyl)-ureido]-phenylglycine 2.18 gm of 5-amino-2-p-fluorobenzyl-4-hydroxy-pyrimidine (0.01 mol) are dissolved in the heat in 120 ml of absolute tetrahydrofurane and mixed with 1.35 ml of triethylamine. The solution is dropped into an ice-cold solution of 1.05 gm of phosgene in 40 ml of tetrahydrofurane. The mixture is subsequently evaporated in vacuo to approximately 50 ml and then dropped with ice-cooling into a solution of 1.51 gm (0.01 mol) of D-phenylglycine which has been dissolved with N/10 sodium hydroxide solution at pH 9 in a 1:1 mixture of tetrahydrofurane and water. After addition, the mixture is stirred at room temperature for 2 hours, the pH value being kept between 9 and 9.5 with N/10 sodium hydroxide solution.

Tetrahydrofurane is subsequently removed in vacuo. The aqueous solution is shaken at pH 7 twice with ethyl acetate, then acidified to pH 2 and carefully shaken with ethyl acetate. After drying and evaporation in a rotary evaporator 2.7 gm of colorless product remain (69%).

IR spectrum: 1720, 1650, 1550 $cm^{-1}$

NNR spectrum (DMSO+$CD_3OD$), signals at ppm: 3.9 (2H), 5.4 (1H), 7.4 (m, 9H), 8.6 (1H).

Calculated: C, 60.60; H, 4.32; N, 14.14. Found: C, 60.40; H, 4.64; N, 14.34.

The following starting materials were synthesized analogously.

(a) D-α-[3-(2-benzyl-4-hydroxy-5-pyrimidyl)-ureido]-phenylglycine, (b) D-α-[3-(2-benzyl-4-hydroxy-5-pyrimidyl)-ureido]-p-hydroxy-phenyl glycine.

(c) D-α-[3-(2-p-chlorophenyl-4-hydroxy-5-pyrimidyl)-ureido]-p-hydroxy-phenylglycine.

(d) D-α-[3-(2-o-chlorobenzyl-4-hydroxy-5-pyrimidyl)-ureido]-p-hydroxyphenylglycine.

(e) D-α-[3-(2-m-chlorobenzyl-4-hydroxy-5-pyrimidyl)-ureido]-phenylglycine.

EXAMPLE J

D-α-[3-(2-p-chloroanilino-4-hydroxy-5-pyrimidyl)-ureido]-phenylglycine 2.36 gm (0.01 mol) of 5-amino-2-p-chloroanilino-4-hydroxypyrimidine are reacted, as specified in Example H, with 1.05 gm of phosgene and 1.35 ml of triethylamine in absolute tetrahydrofurane. The solution is dropped at 0° to 5° C. into a solution of 1.73 gm of the sodium salt of D-α-phenylglycine in 50 ml of 80% aqueous tetrahydrofurane. During the addition, the pH value of the solution is kept at 9.5 to 10 by the addition of 2 N sodium hydroxide solution. The solution is kept for 1 hour at 5° C. and for 2 hours at room temperature. After the reaction, the tetrahydrofurane is removed under reduced pressure and the remaining aqueous phase is shaken twice with ethyl acetate at pH 7.5. The mixture is then brought to pH 1.5 with ice-cooling (dilute hydrochloric acid). The aqueous phase is shaken twice, each time with 100 ml of ethyl acetate. The organic phases are washed with water and dried over anhydrous sodium sulphate. To the organic phase then was added to it the calculated quantity of the sodium salt of 2-ethylhexanic acid, aqueous crystals being separated, which are extracted and dried. Yield: 2.57 gm (56%).

The following can be prepared analogously:

D-α[3-(2-m,p-dichloroanilino-4-hydroxy-5-pyrimidyl)-ureido]-phenylglycine sodium.

D-α-[3-(4-hydroxy-2-o-methylanilino-5-pyrimidyl)-ureido]phenylglycine.

D-α-[3-(2-p-chloro-m-trifluoromethylanilino)-4-hydroxy-5-pyrimidyl)-ureido]phenylglycine D-α-[3-(2-p-bromoanilino-4-hydroxy-5-pyrimidyl)-ureido]phenylglycine.

II. PREPARATION OF THE FINAL PRODUCTS

EXAMPLE 1

D-α-[3-(4-hydroxy-5-pyrimidyl)-ureido]-p-hydroxybenzylpenicillin sodium 1.1 gm (0.01 mol) of 4-hydroxy-5-amino-pyrimidine are dissolved with heating in 800 ml of absolute tetrahydrofurane. The solution is mixed with 1.35 ml of triethylamine (0.01 mol). The mixture is dropped at 0° C. into a solution of 1.05 gm (0.01 mol) of phosgene in 50 ml of absolute tetrahydrofurane. The mixture obtained is subsequently evaporated in vacuo to approximately 100 ml.

4.2 gm (0.01 mol) of amoxycillin trihydrate are suspended in 60 ml of 80% aqueous tetrahydrofurane and mixed slowly at 0° C. with triethylamine until everything has dissolved. The solution prepared above is then added thereto with ice-cooling, the pH value being kept at 7.5 by the addition of triethylamine. After addition, the mixture is stirred for 1 hour at 5° C. and for 1 hour at room temperature and the tetrahydrofurane is subsequently removed in vacuo. The mixture diluted with water to 50 ml and shaken twice at pH 7.0, each time with 50 ml of ethyl acetate. The aqueous phase is then covered with a layer of 300 ml of ethyl acetate and brought to pH 2.0 with 2 N hydrochloric acid with ice-cooling and stirring. The organic phase is separated, the aqueous phase is shaken once again with 50 ml of ethyl acetate and the organic phases are united, dried with sodium sulphate and evaporated to dryness in vacuo.

The remaining product is mixed with a solution of 1.28 gm (0.007 mol) of sodium hexanoate in 25 ml of dry methanol and is thereby dissolved. 300 ml of dry diethyl ether are added thereto while stirring. The precipitated solid product is extracted and dried in vacuo.

Yield: 3.26 gm (62%)

Rf: 0.54.

IR spectrum: 1770, 1650, 1600, 1490 $cm^{-1}$

NMR spectrum ($DMSO+CD_3OD$): Signals at ppm: 1.55 (d,6H), 4.05 (1H), 5.40 (q,2H), 5.5. (1H), 6.8 (d,2H), 7.35 (d,2H), 7.9 (1H), 8.6 (1H).

EXAMPLE 2

D-α-[3-(4-hydroxy-5-pyrimidyl)-ureido]-benzylpenicillin sodium 1.1 gm (0.01 mol) of 4-hydroxy-5-amino-pyrimidine are refluxed for 3 hours with 20 ml of hexamethyl disilazane and a few grains of ammonium sulphate. Excess hexamethyl disilazane is subsequently blown off with nitrogen. The residue is dissolved in 30 ml of absolute tetrahydrofurane, mixed with 1.38 ml of triethylamine and dropped with ice-cooling into a solution of 1 gm of phosgene in 50 ml of absolute tetrahydrofurane. The mixture is then stirred at 0° C. for approximately 1 hour. Triethylamine hydrochloride is filtered off under nitrogen and the solution is evaporated to dryness in vacuo.

4 gm of ampicillin trihydrate (0.01 mol) are dissolved with 2.5 ml of triethylamine in 80 ml of methylene chloride. The solution is dried over magnesium sulphate, filtered and cooled to 0° C. A solution of the solid product obtained above is then dropped into 80 ml of absolute methylene chloride. The mixture is stirred for 1 hour and for 2 hours at room temperature. It is then evaporated to dryness in vacuo. The solid product obtained is mixed with 50 ml of ethyl acetate and 50 ml of water and the pH value adjusted to 7.5. The aqueous phase is shaken twice with a little ethyl acetate. The aqueous phase is then covered with a layer of 500 ml of ethyl acetate and the pH value is slowly brought with dilute hydrochloric acid to 2.0 with ice-cooling. It is filtered off from the hardly soluble product and the aqueous phase is shaken once again with 100 ml of ethyl acetate. After drying and evaporation of the solvent, the sodium salt is prepared, as described in Example 1. Yield: 2.45 gm (48%).

Rf: 0.57.

IR spectrum: 1770, 1660, 1610, 1525 $cm^{-1}$.

NMR ($D_2O$) signals at ppm: 1.4 (3H), 1.5 (3H), 4.25 (1H), 5.3–5.6 (3H), 7.5 (5H), 8.3 (1H), 8.6 (1H).

EXAMPLE 3

D-α-[3-(4-hydroxy-5-pyrimidyl)-ureido]-cyclohexa-1,4-dien-1-yl-methyl-penicillin sodium This penicillin is synthesized analogously to Example 1 by starting from the reaction product of 550 mg (0.005 mol ) of 5-amino-4-hydroxy-pyrimidine with 0.68 ml (0.005 mol) of triethylamine and 0.50 gm of phosgene (0.005 mol) as well as 1.87 gm (0.005 mol) of epicillin sodium.

Yield: 3.12 gm of sodium salt (61%).

IR spectrum: 1770, 1655, 1605, 1535 $cm^{-1}$.

NMR spectrum ($DMSO+CD_3OD$) signals at ppm: 1.50 (6H), 2.50 (4H), 4.05 (1H), 4.90 (1H), 5.30 (2H), 5.65 (3H), 7.9 (1H), 8.55 (1H).

The following are synthesized analogously to Example 1.

D-α-[3-(4-hydroxy-5-pyrimidyl)-ureido]-2-thienylmethyl-penicillin sodium.

D-α-[3-(4-hydroxy-5-pyrimidyl)-ureido]-m,p-dihydroxy benzyl-pencillin sodium.

D-α-[3-(4-hydroxy-5-pyrimidyl)-ureido]-m-chloro-p-hydroxy-benzyl-penicillin sodium.

EXAMPLE 4

D-α-[3-(4-hydroxy-2-methyl-5-pyrimidyl)-ureido]-p-hydroxybenzyl-penicillin sodium.

Analogously to Example 1, starting from 2.5 gm of 5-amino-4-hydroxy-2-methyl-pyridimide (0.02 mol) which has firstly been reacted with 2.1 gm of phosgene and 2.7 ml of triethylamine and then with 8.5 gm of amoxycillin trihydrate (0.002 mol).

Yield: 6.45 gm of sodium salt (60%).

Rf. 0.55.

IR spectrum: 1770, 1660, 1610, 1545 $cm^{-1}$.

NMR spectrum ($D_2O$) signals at ppm: 1.45 (6H), 2.4 (3H), 4.2 (1H), 5.3 (1H), 5.45 (2H), 6.9 (2H), 7.35 (2H), 8.3 (1H).

EXAMPLE 5

D-α-[3-(4-hydroxy-2-methyl-5-pyrimidyl]-ureido]-benzyl-penicillin sodium

Analogously to Example 1, starting from 750 mg of the pyrimidine of Example 4 (0.006 mol), 0.8 ml of triethylamine, 600 mg of phosgene and 2.25 gm (0.006 mol) of ampicillin sodium salt.

Yield: 1.76 gm of sodium salt (56%).

IR spectrum: 1770, 1660, 1610, 1530 $cm^{-1}$.

NMR spectrum ($D_2O$) signals at ppm: 1.50 (6H), 2.45 (3H), 4.15 (1H), 5.3–5.6 (3H), 7.5 (5H), 8.3 (1H).

The following are synthesized analogously:

D-α[3-(4-hydroxy-2-methyl-5-pyrimidyl)-ureido]-2-thienyl methyl-penicillin sodium.

D-α-[3-(4-hydroxy-2-methyl-5-pyrimidyl)-ureido]-m,p-dihydroxybenzyl-penicillin sodium.

D-α-[3-(4-hydroxy-2-methyl-5-pyrimidyl)-ureido]-m-chloro-p-hydroxybenzyl-penicillin sodium.

D-α-[3-(4-hydroxy-2-methyl-5-pyrimidyl)-ureido]-cyclo-hexa-1,4-dien-1-yl-methyl-penicillin sodium.

EXAMPLE 6

D-α-[3-(2-ethyl-4-hydroxy-5-pyrimidyl)-ureido]-p-hydroxybenzyl-penicillin sodium This penicillin is synthesized in the way specified in Example 1 by starting from 2.1 gm (0.005 mol) of amoxycillin trihydrate and the reaction product of 0.7 gm (0.005 mol) of 5-amino-2-ethyl-4-hydroxy-pyrimidine with 500 mg of phosgene and 0.68 ml of triethylamine Yield: 1.62 gm (57%).

Rf: 0.58.

IR spectrum: 1770, 1650, 1600, 1540, 1510 $cm^{-1}$.

NMR spectrum ($DMSO+CD_3OD$) signals at ppm: 1.2 (3H); 1.55 (6H), 2.45 (2H), 4.1 (1H), 5.4 (3H), 6.8 (2H), 7.3 (2H), 8.5 (1H).

The following are synthesized analogously:

D-α[3-(2-ethyl-4-hydroxy-5-pyrimidyl)-ureido]-benzyl-penicillin sodium.

D-α-[3(2-ethyl-4-hydroxy-5-pyrimidyl)-ureido]-cyclohexa-1,4-dien-1-yl-methyl-penicillin sodium

EXAMPLE 7

D-α-[3-(4-hydroxy-2-isopropyl-5-pyrimidyl)-ureido -p-hydroxybenzyl-penicillin sodium Analogously to Example 1, starting from 4.2 gm of amoxycillin trihydrate (0.01 mol) as well as the reaction product of 1.52 gm (0.01 mol) of 5-amino-4-hydroxy-2-isopropyl-pyrimidine with 1.05 gm of phosgene and 1.35 ml of triethylamine.

Yield: 3.0 gm (53%) of sodium salt.

Rf: 0.69

IR spectrum: 1765, 1650, 1610, 1550 $cm^{-1}$

NMR spectrum ($D_2O$) signals at ppm: 1.25 (6H), 1.45 (6H), 2.9 (1H), 4.2 (1H), 5.4 (3H), 6.9 (2H), 7.3 (2H), 8.35 (1H).

EXAMPLE 8

D-α-[3-(2-t-butyl-4-hydroxy-5-pyrimidyl)-ureido]-p-hydroxybenzyl-penicillin sodium This pyrimidine is synthesized analogously to Example 1 by starting from 1.26 gm of amoxycillin trihydrate (0.003 mol) as well as the reaction product of 0.47 gm (0.003 mol) of 5-amino-2-t-butyl-4-hydroxy-pyrimidine with 300 mg of phosgene and 0.41 ml of triethylamine.

Yield: 850 mg of sodium salt (49%).

Rf: 0.64

IR spectrum: 1770, 1650, 1600, 1550 $cm^{-1}$.

NMR spectrum ($D_2O$) signals at ppm: 1.3 (9H), 1.45 (6H), 4.2 (1H), 5.4 (3H), 6.9 (2H), 7.3 (2H), 8.35 (1H).

EXAMPLE 9

D-α-[3-(2-amyl-4-hydroxy-5-pyrimidyl)-ureido]-p-hydroxybenzyl-penicillin sodium

Synthesis analogous to Example 1, starting from 2.1 gm of amoxycillin trihydrate (0.005 mol) as well as the reaction product of 0.85 gm (0.005 mol) of 5-amino-2-amyl-4-hydroxy-pyrimidine with 500 mg of phosgeneand 0.68 ml of triethylamine.

Yield: 1.9 gm of sodium salt (65%).

Rf: 0.70.

IR spectrum: 1770, 1650, 1600, 1550 $cm^{-1}$.

NMR spectrum ($DMSO+CD_3OD$) signals at ppm: 0.9 (3H), 1.3 (6H), 1.55 (6H), 2.5 (2H), 4.05 (1H), 5.45 (3H), 6.8 (2H), 7.3 (2H), 8.55 (1H).

EXAMPLE 10

D-α-[3-(4-hydroxy-2-octyl-5-pyrimidyl)-ureido]-p-hydroxy-benzyl-penicillin sodium Synthesis analogous to Example 1, starting from 840 mg of amoxycillin trihydrate (0.002 mol) and the reaction product of 420 mg (0.002 mol) of 5-amino-4-hydroxy-2-octyl-pyrimidine with 200 mg of phosgene and 0.27 ml of triethylamine.

Yield: 440 mg of sodium salt (35%).

IR spectrum: 1770, 1650, 1600, 1545 $cm^{-1}$

NMR Spectrum ($DMSO+CD_3OD$) signals at ppm: 0.9 (3H), 1.3 (12H), 1.55 (6H), 2.45 (2H), 4.1 (1H), 5.40 (3H), 6.85 (2H), 7.30 (2H), 8.45 (1H).

EXAMPLE 11

D-α-[3-(2-cyclopropyl-4-hydroxy-5-pyrimidyl)-ureido]-p-hdroxybenzyl-penicillin sodium 18.2 gm of 5-amino-2-cyclopropyl-4-hydroxy-pyrimidine (0.12 mol) are dissolved with heating in 800 ml of absolute tetrahydrofurane and mixed with 16.5 ml of triethylamine. This solution is dropped at 0° C. into a solution of 12 gm of phosgene in 250 ml of absolute tetrahydrofurane. The mixture is stirred with ice-cooling for approximately 30 minutes. Nitrogen is subsequently bubbled through the solution in order to remove unreacted phosgene.

50.4 gm of amoxycillin trihydrate are suspended in1.6 liters of aqueous 80% tetrahydrofurane and cooled to 0° C. Enough triethylamine is then added thereto for a solution to be obtained (16.5 ml). The suspension prepared above is added within 60 minutes, the pH value being kept at 7.5 with triethylamine. A further 100 ml of water are added and the reaction mixture is kept at 0°-2° C. for 1 hour. The cooling is removed and the mixture is stirred for 1 hour at room temperature.

500 ml of water are then added thereto and the tetrahydrofurane is removed in vacuo. The remaining water phase is washed twice with 280 ml of ethyl acetate. It is diluted with ice water to 2.5 liters and covered with a layer of 6 liters of ethyl acetate. 2 N hydrochloric acid is slowly added thereto with constant stirring until pH 2.0, the temperature being kept below 5° C. Any insoluble product is filtered off and the layers are separated. The water phase is washed again with 1 liter of ethyl acetate. The organic phase is dried over sodium sulphate and the solvent is removed in vacuo.

The product is suspended in a little water and, with ice-cooling and stirring, mixed dropwise with N/10 sodium hydroxide solution until a pH value of 6.8. The solution obtained is freeze-dried.

Yield: 60.2 gm of sodium salt (89%).

Rf: 0.71.

IR spectrum: 1775, 1660, 1615, 1555 $cm^{-1}$.

NMR Spectrum (DMSO+$CD_3OD$) signals at ppm: 0.95 (4H), 1.55 (6H), 1.9 (1H), 4.05 (1H), 5.35 (2H), 5.45 (1H), 6.8 (2H), 7.3 (2H), 8.48 (1H).

EXAMPLE 12

D-α-[3-(2-cyclopropyl-4-hydroxy-5-pyrimidyl)-ureido]-benzyl-penicillin sodium

This penicillin is prepared analogously to Example 11, starting from 4.0 gm of ampicillin trihydrate as well as the reaction product of 1.51 gm (0.01 mol) of the pyrimidine of Example 11 with 1.0 gm of phosgene and 1.35 ml of triethylamine.

Yield: 4.2 gm of sodium salt (78%).

Rf: 0.74.

IR spectrum: 1770, 1655, 1615, 1540 $cm^{-1}$.

NMR spectrum (DMSO+$CD_3OD$) signals at ppm: 0.95 (4H), 1.55 (6H), 1.9 (1H), 4.0 (1H), 5.45 (3H), 7.45 (5H), 8.40 (1H).

EXAMPLE 13

D-α-[3-(2-cyclopropyl-4-hydroxy-5-pyrimidyl)-ureido]-cyclohexa-1,4-dien-1-yl-methyl-penicillin sodium This penicillin is prepared analogously to Example 11, starting from 1.87 gm of epicillin sodium (0.005 mol) as well as the reaction product of 0.75 gm (0.005 mol) of the pyrimidine of Example 11 with 500 mg of phosgene and 0.68 ml of triethylamine.

Yield: 2.03 gm of sodium salt (74%).

IR spectrum: 1770, 1660, 1605, 1550 $cm^{-1}$,

NMR spectrum (DMSO+$CD_3OD$) signals at ppm: 0.9 (4H), 1.5 (6H), 1.95 (1H), 2.50 (4H), 4.05 (1H), 4.95 (1H), 5.30 (2H), 5.65 (3H), 8.40 (1H).

The following are synthesized analogously:

D-α-[3-(2-cyclopropyl-4-hydroxy-5-pyrimidyl)-ureido]-2-thienylmethyl-penicillin sodium.

D-α-[3-(2-cyclopropyl-4-hydroxy-5-pyrimidyl)-ureido]-m,p-dihydroxybenzyl-penicillin sodium.

D-α-[3-(2-cyclopropyl-4-hydroxy-5-pyrimidyl)-ureido]-m-chloro-p-hydroxybenzyl-penicillin sodium.

D-α-[3-(2-cyclopropyl-4-hydroxy-5-pyrimidyl)-ureido]-m-fluoro-p-hydroxybenzyl-penicillin sodium.

EXAMPLE 14

D-α-[3-(2-cyclobutyl-4-hydroxy-5-pyrimidyl)-ureido]-p-hydroxybenzyl-penicillin sodium This penicillin is prepared analogously to Example 11, starting from 4.2 gm of amoxycillin trihydrate (0.01 mol) as well as the reaction product of 1.65 gm (0.01 mol) of 5-amino-2-cyclobutyl-4-hydroxy-pyrimidine with 1.0 gm of phosgene and 1.38 ml of triethylamine.

Yield: 4.85 gm of sodium salt (84%)

Rf: 0.73.

IR spectrum: 1770, 1660, 1605, 1545 $cm^{-1}$.

NMR spectrum (DMSO+$CH_3OD$) signals at ppm: 1.55 (6H), 1.8-2.5 (m,6H), 3.4 (1H), 5.4 (q,2H), 5.5 (1H), 6.8 (2H), 7.3 (2H), 8.6 (1H).

The following are synthesized analogously:

D-α-[3-(2-cyclobutyl-4-hydroxy-5-pyrimidyl)-ureido]-benzyl-penicillin sodium.

D-α-[3-(2-{2'-ethyl-cyclopropyl}-4-hydroxy-5-pyrimidyl)-ureido]-p-hydroxybenzyl-penicillin sodium.

D-α-[3(2-{2'-ethyl-cyclopropyl}-4-hydroxy-5-pyrimidyl)-ureido]-benzyl-penicillin sodium.

D-α-(3-4-hydroxy-2-{2'-phenyl-cyclopropyl}-5-pyrimidyl)-ureido]-p-hydroxybenzyl-penicillin sodium.

D-α-[3-(4-hydroxy-2-{2'-phenyl-cyclopropyl}-5-pyrimidyl)-ureido]-benzyl-penicillin sodium.

EXAMPLE 15

D-α-[3-(2-cyclopentyl-4-hydroxy-5-pyrimidyl)-ureido]-p-hydroxybenzyl-penicillin sodium This penicillin is prepared analogously to Example 11, starting from 420 mg of amoxycillin sodium (0.001 mol) as well as the reaction product of 180 mg of 5-amino-2-cyclopentyl-4-hydroxy-pyrimidine (0.001 mol) with 100 mg of phosgene and 0.14 ml of triethylamine.

Yield: 405 mg of sodium salt (69%).

Rf: 0.65.

IR spectrum: 1770, 1650, 1600, 1550 $cm^{-1}$.

NMR spectrum (DMSO+$CD_3OD$) signals at ppm: 1.0-2.1 (m,15H), 4.0 (1H), 5.5 (3H), 6.8 (2H), 7.3 (2H), 8.55 (1H).

EXAMPLE 16

D-α-[3-(2-cyclohexyl-4-hydroxy-5-pyrimidyl)-ureido]-p-hydroxybenzyl-penicillin sodium This penicillin is prepared analogously to Example 11, starting from 840 mg of amoxycillin trihydrate (0.002 mol) as well as the reaction product of 385 mg of 5-amino-2-cyclohexyl-4-hydroxy-pyrimidine (0.002 mol) with 200 mg of phosgene and 0.27 ml of triethylamine.

Yield: 720 mg of sodium salt (60%).

Rf: 0.62.

IR spectrum: 1770, 1645, 1600, 1545 $cm^{-1}$.

NMR spectrum (DMSO+$CD_3OD$) signnals at ppm: 1.0-2.1 (m,17H), 4.05 (1H), 5.35 (2H), 5.45 (1H), 6.85 (2H, 7.3 (2H), 8.50 (1H).

EXAMPLE 17

D-α-[3-(4-hydroxy-2-{2'-methyl-cyclopropyl}-5-pyrimidyl)-ureido]-p-hydroxybenzyl-penicillin sodium This penicillin is prepared analogously to Example 11, starting from 4.2 gm of amoxycillin of trihydrate as well as the reaction product of 1.65 gm (0.01 mol) of 5-amino-4-hydroxy-2-(2'-methyl-cyclopropyl)-pyrimidine with 1.0 gm of phosgene and 1.37 ml of triethylamine.

Yield: 3.81 gm of sodium salt (66%).

IR spectrum: 1770, 1650, 1600, 1550 $cm^{-1}$.

NMR spectrum (DMSO+$CD_3OD$) signals at ppm: 0.9–1.7 (m,12H), 1.95 (1H), 4.05 (1H), 5.45 (3H), 6.8 (2H), 7.3 (2H), 8.45 (1H).

The following are prepared analogously:

D-α-[3-(4-hydroxy-2-{2'-methyl-cyclopropyl}-5-pyrimidyl)-ureido]-benzyl-penicillin sodium.

D-α-[3-(4-hydroxy-2-{2'-methyl-cyclopropyl}-5-pyrimidyl)-ureido]-cyclohexa-1,4-dien-1-yl-methyl-penicillin sodium. D-α-[3-(2-cyclohexen-2'-yl-4-hydroxy-5-pyrimidyl)-ureido]-p-hydroxybenzyl-penicillin sodium.

EXAMPLE 18

D-α-[3-(4-hydroxy-2-{1'-methyl-cyclopropyl}-5-pyrimidyl)-ureido]-p-hydroxy-benzyl-penicillin sodium This penicillin is prepared analogously to Example 11, starting from 2.1 gm of amoxycillin trihydrate (0.005 mol) as well as the reaction product of 0.83 gm (0.005 mol) of 5-amino-4-hydroxy-2-(1'-methyl-cyclopropyl)-pyrimidine with 500 mg of phosgene and 0.67 ml of triethylamine.

Yield: 1.54 gm of sodium salt (53%).

Rf: 0.70

IR spectrum: 1765, 1655, 1610, 1550 $cm^{-1}$.

NMR spectrum (DMSO+$CD_3OD$) signals at ppm: 0.9–1.4 (7H), 1.55 (6H), 4.0 (1H), 5.35 (2H), 5.45 (1H), 6.8 (2H), 7.3 (2H), 8.50 (1H).

The following are synthesized analogously:

D-α-[3-(4-hydroxy-2-}1'-methyl-cyclopropyl}-5-pyrimidyl)-ureido]-benzyl-penicillin sodium.

D-α-[3-(2-cyclopropylmethyl-4-hydroxy-5-pyrimidyl)-ureido]-p-hydroxybenzyl-penicillin sodium.

D-α-[3-(2-cyclopropylmethyl-4-hydroxy-5-pyrimidyl)-ureido]-benzyl-penicillin sodium.

EXAMPLE 19

D-α-[3-(2-allyl-4-hydroxy-5-pyrimidyl)-ureido]-p-hydroxybenzyl-penicillin sodium This penicillin is prepared analogously to Example 11, starting from 4.2 gm of amoxycillin trihydrate (0.01 mol) as well as the reaction product of 1.5 1 gm (0.01 mol) of 2-allyl-5-amino-4-hydroxy-pyrimidine with 1.0 gm of phosgene and 1.37 ml of triethylamine.

Yield: 2.54 gm of sodium salt (44%).

IR Spectrum: 1765, 1645, 1610, 1550 $cm^{-1}$.

NMR spectrum (DMSO+$CD_3OD$) signals at ppm: 1.55 (6H), 4.05 (1H), 4.1 (2H), 5.0 (2H), 5.3–6.0 (1,4H), 6.8 (2H), 7.3 (2H), 8.40 (1H).

The following are synthesized analogously.

D-α-[3-(2-allyl-4-hydroxy-5-pyrimidyl)-ureido]-benzyl-penicillin sodium.

D-α-[3-(2-allyl-4-hydroxy-5-pyrimidyl)-ureido]-cyclohexa-1,4-dien-1-yl-methyl-penicillin sodium.

EXAMPLE 20

D-α-[3-(4-hydroxy-2-vinyl-5-pyrimidyl)-ureido]-p-hydroxy-benzyl-penicillin sodium This penicillin is prepared analogous to Example 11, starting from 1.68 gm of amoxycillin trihydrate (0.004 mol) as well as the reaction product of 520 mg (0.004 mol) of 5-amino-4-hydroxy-2-vinyl-pyrimidine with 400 mg of phosgene and 0.54 ml of triethylamine.

Yield: 1.02 gm of sodium salt (51%).

Rf: 0.56.

IR spectrum: 1770, 1655, 1610, 1545 $cm^{-1}$.

NMR spectrum (DMSO+$CD_3OD$) signals at ppm: 1.55 (6H), 4.05 (1H), 5.0–7.0 (m,6H), 6.8 (2H), 7.3 (2H), 8.35 (1H).

The following are synthesized analogously:

D-α-[3-(4-hydroxy-2-vinyl-5-pyrimidyl)-ureido[-benzyl-penicillin sodium.

D-α-[3-(4-hydroxy-2-vinyl-5-pyrimidyl)-ureido]-cyclohexa-1,4-dien-1-yl-methyl-penicillin sodium.

EXAMPLE 21

D-α-[3-(4-hydroxy-2-propargyl-5-pyrimidyl)-ureido]-p-hydroxybenzyl-penicillin sodium This penicillin is prepared analogous to Example 11, starting from 2.52 gm of amoxycillin trihydrate (0.006 mol) as well as the reaction product of 900 mg (0.006 mol) of a 5-amino-4-hydroxy-2-propargyl-pyrimidine with 600 mg of phosgene and 0.8 ml of triethylamine.

Yield: 1.67 gm of sodium salt (46%).

IR spectrum: 1770, 1660, 1610, 1550 $cm^{-1}$.

NMR spectrum (DMSO+$CO_3OD$) signals at ppm: 1.55 (6H), 2.1 (1H), 4.0 (2H), 4.05 (1H), 5.45 (3H), 6.8 (2H), 7.3 (2H), 8.6 (1H).

The following is prepared analogously.

D-α-[3-(4-hydroxy-2-propargyl-5-pyrimidyl)-ureido]-benzyl-penicillin sodium.

EXAMPLE 22

D-α-[3-(2-crotyl-4-hydroxy-5-pyrimidyl)-ureido]-p-hydroxybenzyl-penicillin sodium This penicillin is prepared analogous to Example 11, starting from 4.2 gm of amoxycillin trihydrate (0.01 mol) as well as the reaction product of 1.66 gm (0.01 mol) of 5-amino-2-crotyl-4-hydroxy-pyrimidine with 1.0 gm of phosgene and 1.35 ml of triethylamine.

Yield: 2.33 gm of sodium salt (38%).

Rf. 0.62

IR spectrum: 1765, 1655, 1600, 1550 $cm^{-1}$.

NMR spectrum: (DMSO+$CD_3CD$) signals at ppm: 1.55 (6H), 2.05 (3H), 3.95 (2H), 4.05 (1H), 4.85–6.05 (m,5H), 6.8 (2H), 7.3 (2H), 8.45 (1H).

EXAMPLE 23

D-α-[3-(2-p-chlorobenzyl-4-hydroxy-5-pyrimidyl)-ureido]-p-hydroxybenzyl-penicillin sodium 2.35 gm (0.01 mol) of 5-amino-2-p-chlorobenzyl-4-hydroxy-pyrimidine are dissolved with heating in 100 ml of absolute tetrahydrofurane. 1.0 gm (0.01 mol) of triethylamine is added to this solution. The mixture is dropped with ice-cooling into a solution of 1.05 gm of phosgene (0.01 mol) in absolute tetrahydrofurane. The mixture is then evaporated in vacuo to approximately 40 ml.

4.2 gm of amoxycillin trihydrate are dissolved with ice-cooling in 80 ml of tetrahydrofurane-water mixture (4:1) by means of triethylamine. The mixture prepared above is dropped with cooling into this solution, the pH value being kept at approximately 7.5 by means of triethylamine. After the addition, the mixture is stirred for 1 hour in an ice bath and for 1 hour at room temperature. The tetrahydrofurane is subsequently removed in vacuo. The remaining aqueous solution is shaken at pH 7.0 twice with a little ethyl acetate. The aqueous phase is thereafter covered with a layer of ethyl acetate and slowly brought with dilute hydrochloric acid to pH 2.0 with cooling and stirring. The ethyl acetate phase is removed and the aqueous phase is shaken once again with ethyl acetate. The acid ethyl acetate phases are united, dried with sodium sulphate and evaporated to dryness.

The penicillin obtained is dissolved in a little methanol and mixed with the calculated quantity of sodium hexanoate and the sodium salt obtained is precipitated by the addition of ether. After drying, 4.7 gm of sodium salt (73% yield) are obtained.

Rf: 0.79.

IR spectrum: 1770, 1650, 1610, 1550 $cm^{-1}$.

NMR spectrum ($DMSO+CD_3OD$) signals at ppm: 1.5 (6H), 3.8 (2H), 4.0 (1H), 5.4 (q,2H), 5.45 (1H, 7.0 (dD,4H), 7.35 (4H), 8.45 (1H).

EXAMPLE 24

D-α-[3-(2-p-chlorobenzyl-4-hydroxy-5-pyrimidyl)-ureido]-benzyl-penicillin sodium 1.17 gm (0.005 mol) of pyrimidine of Example 23 are reacted, as specified above, with phosgene and triethylamine. The mixture obtained is dropped with ice-cooling into a solution of 2.0 gm of ampicillin trihydrate and triethylamine in 80% tetrahydrofurane. Treatment is effected analogous to Example 23.

Yield: 2.55 gm of sodium salt (79% yield).

Rf. 0.80.

IR spectrum: 1765, 1650, 1600, 1540 $cm^{-1}$.

NMR spectrum ($DMSO/CD_3OD$): signals at ppm: 1.5 (6H), 3.85 (2H), 4.0 (1H), 5.4 (2H), 5.65 (1H), 7.4 (9H), 8.4 (1H).

EXAMPLE 25

D-α-[3-(2-p-chlorobenzyl-4-hydroxy-5-pyrimidyl)-ureido]-1,4-cyclohexadien-1-yl-methyl-penicillin sodium This penicillin is prepared in the way described in Example 23 from 3.7 gm of epicillin sodium salt (0.01 mol) and the reaction product of 2.35 gm (0.01 mol) of 5-amino-2-p-chlorobenzyl-4-hydroxy-pyrimidine and 1.0 gm of phosgene as well as 1.0 gm of triethylamine.

Yield: 4.9 gm of sodium salt (77%).

IR spectrum: 1770, 1660, 1610, 1550, 1510 $cm^{-1}$.

NMR spectrum (DMSO): signals at ppm: 1.5 (6H), 2.7 (4H), 3.85 (2H), 4.0 (1H), 5.05 (1H), 5.4 (2H), 5.75 (3H), 7.4 (m,4H), 8.5 (1H).

The following are synthesized analogously:

D-α-[3-(2-p-chlorobenzyl-4-hydroxy-5-pyrimidyl)-ureido]-m,p-dihydroxybenzyl-penicillin sodium.

D-α-[3-(2-p-chlorobenzyl-4-hydroxy-5-pyrimidyl)-ureido]-m-chloro-p-hydroxybenzyl-penicillin sodium.

EXAMPLE 26

D-α-[3-(2-p-fluorobenzyl-4-hydroxy-5-pyrimidyl)-ureido]-p-hydroxybenzyl-penicillin sodium This penicillin is synthesized in the way described in Example 23, starting from 4.2 gm of amoxycillin trihydrate (0.01 mol) and the reaction product of 2.2 gm (0.01 mol) of 5-amino-2-p-fluorobenzyl-4-hydroxypyrimidine with 1.01 gm of phosgene and 1.0 gm of triethylamine. Treatment is effected analogous to Example 23.

Yield: 5.1 gm of sodium salt (80%)

Rf: 0.78

NMR spectrum ($DMSO/CD_3OD$): signals at ppm: 1.5 (6H), 3.85 (2H), 4.0 (1H), 5.35 (q,2H), 5.5 (1H), 6.95 (m,4H), 7.35 (m,4H), 8.55 (1H).

EXAMPLE 27

D-α-[3-(2-p-fluorobenzyl-4-hydroxy-5-pyrimidyl)-ureido]-1,4-cyclohexadien-1-yl-methyl-penicillin sodium 3.7 gm (0.01 mol) of epicillin sodium are dissolved in 50 ml of a tetrahydrofurane-water mixture. With ice-cooling the reaction product of 2.2 gm (0.01 mol) of the pyrimidine of Example 26 with 1.01 gm of phosgene and 1.0 gm of triethylamine is added thereto. The pH value is kept at 7.5 with triethylamine and the mixture is allowed to react for 1 hour with ice-cooling and for 2 hours at room temperature. Treatment of the mixture is effected analogous to Example 23.

Yield: 5.2 gm of sodium salt (84%).

Rf: 0.85.

IR spectrum: 1765, 1660, 1610, 1550 $cm^{-1}$.

NMR spectrum ($DMSO+CD_3OD$): signals at ppm: 1.55 (6H), 2.75 (4H), 3.90 (2H), 4.05 (1H), 5.1 (1H), 5.45 (2H), 5.75 (3H), 7.4 (m,4H), 8.55 (1H).

The following is synthesized analogously:

D-α-[3-(2-p-fluorobenzyl-4-hydroxy-5-pyrimidyl-ureido]m,p-dihydroxybenzyl-penicillin sodium.

EXAMPLE 28

D-α-[3-(2-m-chlorophenyl-4-hydroxy-5-pyrimidyl)-ureido]-p-hydroxybenzyl-penicillin sodium Analogous to Example 23 from 8.4 gm of amoxycillin trihydrate (0.02 mol) and the reaction product of 4.43 gm (0.02 mol) of 5-amino-2-m-chlorophenyl-4-hydroxypyrimidine with 2.1 gm of phosgene and 2.0 gm of N-methyl morpholine.

Yield: 9.4 gm of sodium salt (74%).

Rf: 0.77.

IR spectrum: 1770, 1650, 1600, 1550 $cm^{-1}$.

NMR spectrum: ($DMSO+CD_3OD$): signals at ppm: 1.55 (6H), 4.1 (1H), 5.45 (q,2H), 5.6 (1H), 7.1 (dd/4H), 7.6 (2H), 8.1 (2H), 8.6 (1H).

EXAMPLE 29

D-α-[3-(2o'-dichlorobenzyl-4-hydroxy-5-pyrimidyl)-ureido]-benzyl-penicillin sodium Analogous to Example 23 from 1.9 gm of ampicillin sodium (0.005 mol) and the reaction product of 1.35 gm (0.005 mol) of 5-amino-2-o', o'-dichlorobenzyl-4-hydroxypyrimidine with 500 mg of phosgene and 0.68 ml of triethylamine.

Yield: 2.67 gm (80%) of sodium salt.

Rf: 0.80.

IR spectrum: 1770, 1655, 1610, 1545 $cm^{-1}$.

NMR spectrum ($DMSO+CD_3OD$): signals at ppm: 1.5 (6H), 4.0 (1H), 4.3 (2H), 5.4 (q,2H), 5.7 (1H), 7.5 (m,8H), 8.45 (1H).

EXAMPLE 30

D-α-[3-(2-o,p-dichlorobenzyl-4-hydroxy-5-pyrimidyl)-ureido]-p-hydroxybenzyl-penicillin sodium 2.16 gm of 5-amino-2-o,p-dichlorobenzyl-4-hydroxypyrimidine (0.008 mol) are dissolved with heating in 100 ml of tetrahydrofurane. 1.1 ml of triethylamine (0.0078 mol) are added to this solution and the mixture is dropped rapidly into an ice-cooled solution of 850 mg (0.0085 mol) of phosgene in 30 ml of tetrahydrofurane. After approximately 20 minutes excess phosgene is blown off with nitrogen and the mixture is evaporated in vacuo to approximately 40 ml. 3.4 gm of amoxycillin trihydrate (0.008 mol) are dissolved with triethylamine in 60 ml of 80% aqueous tetrahydrofurane. The mixture prepared above is dropped into this solution with ice-cooling. The pH value is kept at approximately 7.5 by the addition of triethylamine. After the addition, the mixture is stirred for two hours with ice-cooling and for 1 hour at room temperature. Tetrahydrofuran is subsequently removed in vacuo and the mixture is filled up with water to approximately 100 ml and shaken twice, each time with 50 ml of ethyl acetate. The aqueous phase is then brought with hydrochloric acid to pH 2 with vigorous cooling. The precipitated product is extracted immediately, washed with a little cold water and ether and dried in vacuo. The sodium salt is prepared in the way specified in Example 23.

Yield: 3.5 gm of sodium salt (66%).

RF: 0.91.

IR spectrum: 1770, 1660, 1605, 1545 $cm^{-1}$.

NMR spectrum (DMSO+$CD_3OD$): signals at ppm: 1.55 (6H), 4.05 (1H), 4.1 (2H), 5.45 (q,2H) 5.55 (1H), 7.1 (dd,4H), 7.45 (2H), 7.65 (1H), 8.55 (1H).

EXAMPLE 31

D-α-[3-(2-o,p-dichlorobenzyl-4-hydroxy-5-pyrimidyl)-ureido]-benzyl-penicillin sodium This penicillin is prepared analogous to Example 30 from 2.7 gm (0.01 mol) of the pyrimidine of Example 30 and 4.0 gm of ampicillin trihydrate (0.01 mol).

Yield: 5.03 gm of sodium salt (76%).

Rf: 0.91.

IR spectrum: 1765, 1660, 1610, 1540 $cm^{-1}$. NMR spectrum (DMSO+$CD_3OD$); signals at ppm: 1.5 (6H), 4.05 (3H), 5.4 (q,2H), 5.7 (1H), 7.45 (8H), 8.55 (1H).

EXAMPLE 32

D-α-[3-(2-m,p-dichlorobenzyl-4-hydroxy-5-pyrimidyl)-uredio]-benzyl-penicillin sodium Analogous to Example 30 from 2.0 gm of ampicillin trihydrate (0.005 mol) and 1.35 gm (0.005 mol) of 5-amino-2-m,p-dichlorobenzyl-4-hydroxy-pyrimidine.

Yield: 2.5 gm of sodium salt (75%).

Rf: 0.89.

IR spectrum: 1775, 1655, 1615, 1555 $cm^{-1}$.

NMR spectrum (DMSO+$CD_3OD$): signals at ppm: 1.55 (6H), 4.05 (1H), 4.2 (2H), 5.45 (q,2H), 5.65 (1H), 7.5 (m,8H), 8.50 (1H).

EXAMPLE 33

D-α-[3-(2-p-amino-m,m-dichlorobenzyl-4-hydroxy-5-pyrimidyl)-ureido]-p-hydroxybenzyl-penicillin sodium This penicillin is prepared analogous to Example 30 by starting from 2.5 gm of amoxycillin (0.006 mol) and the reaction product of 1.71 gm of 5-amino-2-(p-amino-m,m-dichloro)-benzyl-4-hydroxy-pyrimidine (0.006 mol) with 600 mg of phosgene and 0.82 ml of triethylamine.

Yield: 2.95 gm of sodium salt (54%).

Rf: 0.88.

IR spectrum: 1770, 1650, 1615, 1550 $cm^{-1}$.

NMR spectrum (DMSO+$CD_3OD$): signals at ppm: 1.55 (6H), 4.0 (1H), 4.10 (2H), 5.45 (q,2H), 5.65 (1H), 6.9 (m,4H), 7.3 (d,2H), 8.50 (1H).

EXAMPLE 34

D-α-[3-(2-o-chlorobenzyl-4-hydroxy-5-pyrimidyl)-ureido]-benzyl-penicillin sodium Analogously to Example 30 starting from 4.0 gm of ampicillin trihydrate (0.01 mol) and 2.35 gm (0.01 mol) of 5-amino-2-o-chlorobenzyl-4-hydroxy-pyrimidine.

Yield: 5.8 gm of sodium salt (91%).

Rf: 0.70.

IR spectrum: 1770, 1660, 1610, 1540 $cm^{-1}$.

NMR spectrum (DMSO+$CD_3OD$): signals at ppm: 1.55 (6H), 3.95 (1H), 4.05 (2H), 5.5 (q,2H), 5.75 (1H), 7.5 (m,9H), 8.6 (1H).

EXAMPLE 35

D-α-[3-(2-m-chlorobenzyl-4-hydroxy-5-pyrimidyl)-ureido]-p-hydroxybenzyl-penicillin sodium This penicillin is prepared analogous to Example 30, starting from 840 mg of amoxycillin trihydrate (0.002 mol) and the reaction product of 470 mg of 5-amino-2-m-chlorobenzyl-4-hydroxy-pyrimidine (0.002 mol) with 200 mg of phosgene and 0.27 ml of triethylamine.

Yield: 1.3 gm of sodium salt (88%).

Rf: 0.73.

IR spectrum: 1770, 1665, 1610, 1550 $cm^{-1}$.

NMR spectrum (DMSO+$CD_3OD$): signals at ppm: 1.5 (6H), 3.95 (1H), 4.10 (2H), 5.45 (q,2H), 5.55 (1H), 6.85 (d,2H), 7.45 (m,6H), 8.60 (1H).

EXAMPLE 36

D-α-[3-(2-o-chlorophenyl-4-hydroxy-5-pyrimidyl)-ureido]-p-hydroxybenzyl-penicillin sodium 2.16 gm (0.01 mol) of 5-amino-2-o-chlorophenyl-4-hydroxy-pyrimidine. 1.05 gm of phosgene and 1.35 ml of triethylamine are reacted, as described in Example 30 in absolute tetrahydrofurane. Triethylamine hydrochloride is filtered off and the solution is evaporated to approximately 50 ml. This solution is dropped with ice-cooling into the solution, prepared with triethylamine, of 4.2 gm of amoxycillin trihydrate in 60 ml of 80% aqueous tetrahydrofurane. Treatment is effected, as described in Example 23, by shaking the desired penicillin acid from water at pH 2 with ethyl acetate.

Yield: 5.3 gm of sodium salt (84%).

Rf: 0.80.

IR spectrum: 1770, 1660, 1600, 1545 $cm^{-1}$.

NMR Spectrum (DMSO+$CD_3OD$): signals at ppm: 1.55 (6H), 4.1 (1H), 5.5 (q,2H), 5.6 (1H), 6.9 (d,2H), 7.4 (d,2H), 7.7 (4H), 8.8 (1H).

The following penicillins are prepared analogous to Example 36 from amoxycillin and the reaction product of the corresponding pyrimidine with phosgene.

D-α-[3-(4-hydroxy-2-o-methylphenyl-5-pyrimidyl)-ureido]-p-hydroxybenzyl-penicillin sodium.

D-α-[3-(4-hydroxy-2-p-methoxycarbonylbenzyl-5-pyrimidyl)-ureido]-p-hydroxybenzyl-penicillin sodium.

D-α-[3-(2-p-dimethylaminocarbonyl-benzyl-4-hydroxy-5-pyrimidyl)-ureido]-p-hydroxybenzyl-penicillin sodium.

D-α-[3-(4-hydroxy-2-m-methylbenzyl-5-pyrimidyl)-ureido]-p-hydroxybenzyl-penicillin sodium.

D-α-[3-(2-p-ethylbenzyl-4-hydroxy-5-pyrimidyl)-ureido]-p-hydroxybenzyl-penicillin sodium.

D-α-[3-(2-p-ethoxybenzyl-4-hydroxy-5-pyrimidyl)-ureido]-p-hydroxybenzyl-penicillin sodium.

EXAMPLE 37

D-α-[3-(4-hydroxy-2-p-methoxyphenyl-5-pyrimidyl)-ureido]-p-hydroxybenzyl-penicillin sodium This penicillin is prepared analogous to Example 36, starting from 4.2 gm of amoxycillin trihydrate (0.01 mol) and the reaction product of 2.17 gm (0.01 mol) of 5-amino-4-hydroxy-2-p-methoxyphenyl-pyrimidine with 1.05 gm of phosgene.

Yield: 5.4 gm of sodium salt (77%).

Rf: 0.69.

IR spectrum: 1765, 1655, 1610, 1550, 1510 $cm^{-1}$.

NMR spectrum (DMSO+$CD_3OD$): signals at ppm: 1.5 (6H), 3.85 (s,3H), 4.05 (1H), 5.4 (q,2H), 5.5 (1H), 6.8 (d,2H), 7.1 (d,2H), 7.3 (d,2H), 8.1 (d,2H), 8.5 (s,1H).

EXAMPLE 83

D-α-[3-(4-hydroxy-2-m-trifluoromethylphenyl-5-pyrimidyl)-ureido]-p-hydroxybenzyl-penicillin sodium Analogous to Example 23, starting from 2.1 gm of amoxycillin trihydrate (0.005 mol) and 1.28 gm of 5-amino-4-hydroxy-2-m-trifluoromethylphenyl-pyrimidine (0.005 mol).

Yield: 2.45 gm of sodium salt (73%).

Rf: 0.78

IR spectrum: 1765, 1660, 1600, 1550 $cm^{-1}$.

NMR spectrum (DMSO+$CD_3OD$): signals at ppm: 1.5 (6H), 4.0 (1H), 5.35 (q,2H), 5.5 (1H), 7.0 (dD,4H), 7.8 (m,2H), 8.4 (m,2H), 8.8 (1H).

EXAMPLE 39

D-α-[3-(4-hydroxy-2-m-methylphenyl-5-pyrimidyl)-ureido]-benzyl-penicillin sodium Analogous to Example 23 from 4.0 gm of ampicillin trihydrate (0.01 mol) and 2.0 gm (0.01 mol) of 5-amino-4-hydroxy-2-m-methylphenyl-pyrimidine.

Yield: 4.14 gm (69%).

Rf: 0.78.

IR spectrum: 1770, 1650, 1600, 1550 $cm^{-1}$.

NMR spectrum (DMSO+$CD_3OD$): signals at ppm: 1.55 (6H), 2.4 (3H), 4.0 (1H), 5.4 (q,2H), 5.5 (1H), 7.5 (m,7H), 8.0 (m,2H), 8.7 (1H).

EXAMPLE 40

D-α-[3-(4-hydroxy-2-p-methylbenzyl-5-pyrimidyl)-ureido]-benzyl-penicillin sodium.

Analogous to Example 23 from 1.6 gm of ampicillin trihydrate (0.004 mol) and 860 mg (0.04 mol) of 5-amino-4-hydroxy-2-p-methylbenzyl-pyrimidine.

Yield: 1.5 gm of sodium salt (64%).

Rf: 0.73.

IR spectrum: 1770, 1660, 1600, 1540 $cm^{-1}$.

NMR spectrum ($CD_3OD$): signals at ppm: 1.55 (6H), 2.3 (3H), 3.9 (2H), 4.2 (1H), 5.5 (q,2H), 5.5 (1H), 7.5 (m,9H), 8.6 (1H).

EXAMPLE 41

D-α-[3-(4-hydroxy-2-o-methylbenzyl-5-pyrimidyl)-ureido]-benzyl-penicillin sodium Analogous to Example 23 from 2.4 gm of ampicillin trihydrate (0.006 mol) and 1.28 gm (0.006 mol) of 5-amino-4-hydroxy-2-o-methylbenzyl-pyrimidine.

Yield: 2.0 gm of sodium salt (55%).

Rf: 0.66.

IR spectrum: 1775, 1660, 1605, 1545 $cm^{-1}$.

NMR spectrum (DMSO+$CD_3OD$): signals at ppm: 1.5 (6H), 2.3 (3H), 4.9 (2H), 4.05 (1H), 5.4 (q,2H), 5.7 (1H), 7.4 (m,9H), 8.55 (1H).

EXAMPLE 42

D-α-[3-(4-hydroxy-2-p-methylmercaptobenzyl-5-pyrimidyl)-ureido]-p-hydroxybenzyl-penicillin sodium Analogous to Example 36, starting from 420 mg of amoxycillin trihydrate (0.001 mol) and the reaction product of 250 mg (0.001 mol) of 5-amino-4-hydroxy-2-p-methylmercaptobenzyl-pyrimidine with 105 mg of phosgene. Treatment is effected analogously to Example 23.

Yield: 320 mg of sodium salt (50%).

Rf: 0.84.

IR spectrum: 1765, 1665, 1610, 1545 $cm^{-1}$.

NMR spectrum (DMSO+$CD_3OD$): signals at ppm: 1.55 (6H), 2.95 (3H), 4.0 (2H), 4.1 (1H), 5.40 (q,2H), 5.65 (1H), 7.1 (dd,4H), 7.5 (dd,4H), 8.6 (1H).

The following are synthesized analogously:

(a) D-α-[3-(4-hydroxy-2-p-methylsulphinylbenzyl-5-pyrimidyl)-ureido]-p-hydroxybenzyl-penicillin sodium.

(b) D-α-[3-(4-hydroxy-2-p-methylsulphonylbenzyl-5-pyrimidyl)-ureido]-p-hydroxybenzyl-penicillin sodium.

EXAMPLE 43

D-α-[3-(4-hydroxy-2-p-methoxybenzyl-5-pyrimidyl)-ureido]-p-hydroxybenzyl-penicillin sodium Analogous to Example 23, starting from 16.8 gm of amoxycillin trihydrate (0.04 mol) and the reaction product of 9.08 gm (0.04 mol) of 5-amino-4-hydroxy-2-p-methylbenzyl-pyrimidine with 4.1 gm of phosgene and 5.4 ml of triethylamine.

Yield: 18.6 gm of sodium salt (72%).

Rf: 0.79.

IR spectrum: 1770, 1660, 1615, 1550 $cm^{-1}$.

NMR spectrum (DMSO+$CD_3OD$): signals at ppm: 1.55 (6H), 3.75 (2H), 3.95 (1H), 5.35 (q,4H), 5.45 (1H), 7.0 (m,8H), 8.4 (1H).

The following are synthesized analogously:

(a) D-α-[3-(2-p-acetoxybenzyl-4-hydroxy-5-pyrimidyl)-ureido]-p-hydroxybenzyl-penicillin sodium.

(b) D-α-[3-(2-p-acetylaminobenzyl-4-hydroxy-5-pyrimidyl)-ureido]-p-hydroxybenzyl-penicillin sodium.

(c) D-α-[3-(2-p-aminocarbonylbenzyl-4-hydroxy-5-pyrimidyl)-ureido]-p-hydroxybenzyl-penicillin sodium.

(d) D-α-[3-(4-hydroxy-2-p-methylsulphonylaminobenzyl-5-pyrimidyl)-ureido]-p-hydroxybenzyl-penicillin sodium.

(e) D-α-[3-(4-hydroxy-2-o-methoxybenzyl-5-pyrimidyl)-ureido]-p-hydroxybenzyl-penicillin sodium

EXAMPLE 44

D-α-[3-(2-m,p-dimethoxybenzyl-4-hydroxy-5-pyrimidyl)-ureido]-benzyl-penicillin sodium This penicillin is synthesized analogous to Example 23, starting from 1.3 gm (0.005 mol) of 5-amino-4-hydroxy-2-m,p-dimethoxybenzyl-pyrimidine and 530 mg of phosgene as well as 2.0 gm of ampicillin trihydrate (0.005 mol). Treatment is effected analogous to Example 23.

Yield: 2.24 gm of sodium salt (68%).

Rf: 0.82.

NMR spectrum (DMSO+$CD_3OD$): signals at ppm: 1.5 (6H), 3.75 (6H), 3.8 (2H), 4.0 (1H), 5.45 (q,2H), 5.7 (1H), 7.0 (d,2H), 7.5 (m,5H), 8.6 (1H).

The following is synthesized analogously.

D-α-[3-(4-hydroxy-2-m,m,p-trimethoxybenzyl-5-pyrimidyl)ureido]-p-hydroxybenzyl-penicillin sodium.

EXAMPLE 45

D-α-[3-(2-p-bromobenzyl-4-hydroxy-5-pyrimidyl)-ureido]-p-hydroxybenzyl-penicillin sodium 2.79 gm (0.01 mol) of 5-amino-2-p-bromobenzyl-4-hydroxy-pyrimidine are reacted in the conventional way with 1.05 gm of phosgene and 1.35 ml of triethylamine in 100 ml of absolute tetrahydrofurane. Triethylamine hydrochloride is filtered off and the solution obtained is dropped with ice-cooling into 4.2 gm (0.01 mol) of amoxycillin trihydrate which has been dissolved with N/100 sodium hydroxide solution in 80 ml of 80% aqueous tetrahydrofurane with control of the pH value. Further reaction and treatment are effected analogous to Example 23.

Yield: 4.05 gm of sodium salt (59%).

Rf: 0.81

IR spectrum: 1770, 1655, 1610, 1545 $cm^{-1}$.

NMR spectrum (DMSO+$CD_3OD$): signals at ppm: 1.55 (6H), 3.9 (1H), 4.1 (2H), 5.45 (q,2H), 5.6 (1H), 6.8 (d,2H), 7.45 (m,6H), 6.8 (1H).

EXAMPLE 46

D-α-[3-(4-hydroxy-2-p-nitrobenzyl-5-pyrimidyl)-ureido]-p-hydroxybenzyl-penicillin sodium 500 mg of 5-amino-4-hydroxy-2-p-nitrobenzylpyrimidine (0.002 mol) are dissolved with heating in 50 ml of dry pyridine. This solution is dropped rapidly into a solution of 210 mg of phosgene in 50 ml of absolute tetrahydrofurane. The mixture obtained is evaporated to dryness in vacuo. The remaining solid product is added with ice-cooling portionwise to 850 mg (0.002 mol) of amoxycillin trihydrate which has been dissolved with triethylamine in 40 ml of 80% tetrahydrofurane. In so doing, the pH value is kept at approximately 7.5.

The mixture is left to react for 1 hour with ice-cooling and for 2 hours at room temperature. The tetrahydrofurane is then removed in vacuo and the aqueous solution is shaken twice with a little ethyl acetate. The mixture is subsequently cooled with ice and carefully acidified to pH 2 with 2 N hydrochloric acid. The precipitated product is filtered off and dried. The sodium salt is prepared in a conventional way. Yield: 650 mg of sodium salt (49%).

Rf: 0.87.

IR spectrum: 1770, 1655, 1605, 1545 $cm^{-1}$.

NMR spectrum (DMSO+$CD_3OD$): signals at ppm: 1.5 (6H), 3.95 (1H), 4.2 (2H), 5.5 (q,2H), 5.75 (1H), 7.1 (dd,4H), 8.0 (m,4H), 8.8 (1H).

The following is synthesized analogously:

D-α-[3-(2-p-cyanobenzyl-4-hydroxy-5-pyrimidyl)-ureido]-p-hydroxybenzyl-penicillin sodium.

EXAMPLE 47

D-α-[3-(2-p-dimethylaminophenyl-4-hydroxy-5-pyrimidyl)-ureido]-p-hydroxybenzyl-penicillin sodium Analogous to Example 23, starting from 5.0 gm of amoxycillin trihydrate (0.012 mol) and 2.9 gm (0.012 mol) of 5-amino-2-p-dimethylaminophenyl-4-hydroxypyrimidine. Treatment analogous to Example 23.

Yield: 3.0 gm of sodium salt (39%).

Rf: 0.82.

IR spectrum: 1775, 1660, 1615, 1570 $cm^{-1}$.

NMR spectrum (DMSO+$CD_3OD$): signals at ppm: 1.6 (6H), 3.05 (6H), 4.05 (1H), 5.45 (q,2H), 5.5 (1H), 6.9 (4H), 7.45 (2H), 8.1 (2H), 8.7 (1H).

The following are synthesized analogously:

(a) D-α-[3-(2-p-dimethylaminobenzyl-4-hydroxy-5-pyrimidyl)-ureido]-p-hydroxybenzyl-penicillin sodium, (b) D-α-[3-(4-hydroxy-2-p-methylaminophenyl-5-pyrimidyl)-ureido]-benzyl-penicillin sodium.

(c) D-α-[3-(2-p-hydroxyphenyl-4-hydroxy-5 -pyrimidyl)-ureido]-p-hydroxybenzyl-penicillin sodium.

EXAMPLE 48

D-α-[3-(2-p-acetylbenzyl-4-hydroxy-5-pyrimidyl)-ureido]-p-hydroxybenzyl-penicillin sodium Analogous to Example 23 starting from 1.21 gm (0.005 mol) of 5-amino-2-p-acetylbenzyl-4-hydroxypyrimidine and 2.1 gm of amoxycillin trihydrate (0.005 mol).

Yield: 2.45 mg of sodium salt (75%).

Rf: 0.79.

IR spectrum: 1770, 1665, 1610, 1550 $cm^{-1}$.

NMR spectrum (DMSO+$CD_3OD$): signals at ppm: 1.55 (6H), 2.6 (3H), 4.0 (2H), 4.05 (1H), 5.5 (q,4H), 5.55 (1H), 6.85 (d,2H), 7.4 (d,2H), 7.6 (d,2H), 8.05 (d,2H), 8.65 (1H).

EXAMPLE 49

D-α-[3-(2-p-fluorobenzyl-4-hydroxy-5-pyrimidyl)-ureido]-benzyl-penicillin sodium 1.98 gm of D-α-[3-(2-p-fluorobenzyl-4-hydroxy-5-pyrimidyl)-ureido]-phenylglycine (0.005 mol) are dissolved with 500 mg (0.005 mol) of N-methylmorpholine in 40 ml of absolute tetrahydrofuran. The mixture is cooled to −15° C. and a solution of 550 mg (0.0055 mol) of ethyl chloroformate in 5 ml of absolute tetrahydrofurane is added thereto. The clear solution is stirred for 30 minutes at −10° C. A solution os 1.58 gm of 6-aminopenicillin acid-triethyl ammonium salt (0.005 mol) in 20 ml of methylene chloride is then added thereto in such a way that the temperature does not exceed −10° C. The mixture is allowed to react for 1 hour at −5° C., for 1 hour at 5° C. and for 1 hour at room temperature. It is subsequently evaporated to dryness in vacuo, 50 ml of water are added thereto and the pH value is brought to 7.0. The aqueous phase is shaken out twice with ethyl acetate, the mixture is then covered with a layer of 200 ml of ethyl acetate and dilute hydrochloric acid is added thereto with cooling and stirring until the pH value has reached 2.0 The ethyl acetate phase is removed, the aqueous phase is shaken once again with 50 ml of ethyl acetate and the two ethyl acetate phases are united, dried over sodium sulphate and evaporated to dryness. The free acid is then converted into the sodium salt in methanol/ether with sodium hexanoate.

Yield: 1.57 gm of sodium salt (51%).

Rf: 0.67.

IR spectrum: 1770, 1660, 1610, 1550 $cm^{-1}$.

NMR spectrum (DMSO+$CD_3OD$): signals at ppm: 1.5 (6H), 3.9 (2H), 4.1 (1H), 5.45 (q,2H), 5.7 (1H), 7.5 (m,9H), 8.6 (1H).

EXAMPLE 50

D-α-[3-(2-benzyl-4-hydroxy-5-pyrimidyl)-ureido]-benzylpenicillin sodium

Analogous to Example 49, starting from 3.15 gm of 6-aminopenicillanic acid-triethylammonium salt (0.01 mol) and 3.78 gm (0.01 mol) of D-α-[3-(2-benzyl-4-hydroxy-5-pyrimidyl)-ureido]-phenylglycine.

Yield: 3.55 gm of sodium salt (60%).

Rf: 0.71.

IR spectrum: 1775, 1665, 1620, 1550 $cm^{31\ 1}$.

NMR spectrum (DMSO+$CD_3OD$): signals at ppm: 1.5 (6H), 4.0 (1H), 4.1 (2H), 5.40 (q,2H),5.5 (1H), 7.5 (m,10H), 8.5 (1H).

EXAMPLE 51

D-α-[3-(2-benzyl-4-hydroxy-5-pyrimidyl)-ureido]-p-hydroxybenzyl-penicillin sodium Analogous to Example 49, starting from 950 mg of 6-aminopenicillanic acid-triethylammonium salt (0.003 mol) and 1.15 gm (0.003 mol) of D-α-[3-(2-benzyl-4-hydroxy-5-pyrimidyl)-ureido]-p-hydroxyphenylglycine.

Yield: 980 mg of sodium salt (55%).

Rf: 0.68.

IR spectrum: 1770, 1660, 1610, 1545 $cm^{-1}$.

NMR spectrum (DMSO+$CD_3OD$): signals at ppm: 1.55 (6H), 4.05 (1H), 4.15 (2H), 5.45 (q,2H), 5.60 (1H), 6.9 (d,2H), 7.5 (m,7H), 8.55 (1H).

EXAMPLE 52

D-α-[3-(2-p-chlorophenyl-4-hydroxy-5-pyrimidyl)-ureido]-p-hydroxybenzyl-penicillin sodium Analogous to Example 49 from 1.67 gm of 6-aminopenicillanic acid-triethylammonium salt (0.005 mol) and 2.05 gm of D-α-[3-(2-p-chlorophenyl-4-hydroxy-5-pyrimidyl)ureido]-p-hydroxyphenyl glycine (0.005 mol).

Yield: 1.94 gm of sodium salt (61%).

Rf. 0.78.

IR spectrum: 1770, 1655, 1610, 1550 $cm^{-1}$.

NMR spectrum (DMSO+$CD_3OD$): signals at ppm: 1.55 (6H), 4.0 (1H), 5.45 (q,2H), 5.55 (1H), 6.8 (d,2H), 7.35 (d,2H), 7.6 (d,2H), 8.2 (d,2H), 8.8 (1H).

EXAMPLE 53

D-α-[3-(2-m-chlorobenzyl-4-hydroxy-5-pyrimidyl)-ureido]-benzyl-penicillin sodium A suspension of 2.16 gm (0.01 mol) of 6-aminopenicillanic acid and 3 ml of N,O-bis-(trimethylsilyl)acetamide in dry dimethyl formamide (30 ml) is stirred for 2 hours at room temperature. This solution is dropped at −10° C. into a solution prepared at −15° C. of 4.25 gm (0.01 mol) of D-α-[3-(2-m-chlorobenzyl-4-hydroxy-5-pyrimidyl)-ureido]-phenylglycine, 1.0 gm of N-methylmorpholine and 1.0 gm of ethyl chloroformate in absolute tetrahydrofurane. The mixture is stirred for 1 hour at 0° C. and for 1 hour at room temperature, tetrahydrofurane and a part of the dimethyl formamide are removed in vacuo and the product is then mixed with 250 ml of ice water. The aqueous solution is adjusted to pH 7.0 and extraced twice with ethyl acetate. It is then cooled, covered with a layer of 200 ml of ethyl acetate and adjusted to pH 2 with dilute hydrochloric acid. The aqueous phase is extracted once again with ethyl acetate, the ethyl acetate phases are united and dried and the solvent is removed in vacuo. The sodium salt is prepared in a conventional way from the penicillin acid.

Yield: 2.92 gm of sodium salt (46%).

Rf: 0.76%.

IR spectrum: 1770, 1665, 1610, 1545 $cm^{-1}$.

NMR spectrum (DMSO+$CD_3OD$): signals at ppm: 1.55 (6H), 3.8 (2H), 4.0 (1H), 5.40 (q,2H), 5.6 (1H), 7.4 (m,9H), 8.5 (1H).

The following is synthesized analogously:

D-α-[3-(4-hydroxy-2-phenyl-5-pyrimidyl)-ureido]-p-hydroxybenzyl-penicillin sodium.

EXAMPLE 54

D-α-[3-(2-o-chlorobenzyl-4-hydroxy-5-pyrimidyl)-ureido]-p-hydroxybenzyl-penicillin sodium Analogous to Example 53, starting from 1.13 gm (0.005 mol) of 6-amino-penicillanic acid and 2.2 gm (0.005 mol) of D-α-[3-(2-o-chlorobenzyl-4-hydroxy-5-pyrimidyl)-ureido]-p-hydroxyphenylglycin. Treatment analogous to Example 53.

Yield: 2.27 gm of sodium salt (70%).

Rf: 0.80.

IR spectrum: 1770, 1655, 1610, 1540 $cm^{-1}$.

NMR spectrum (DMSO+$CD_3OD$): signals at ppm: 1.55 (6H), 4.05 (1H), 4.1 (2H), 5.4 (q,2H), 5.45 (1H), 6.8 (d,2H), 7.4 (M,6H), 8.55 (1H).

EXAMPLE 55

D-α-[3(4-hydroxy-2-{1'-phenylethylγ-5-pyrimidyl)-ureido]-p-hydroxybenzyl-penicillin sodium.

This penicillin is prepared analogously to Example 11, starting from 4.2 gm of amoxycillin trihydrate as well as the reaction product of 2.15 gm (0.01 mol) of 5-amino-4-hydroxy-2-(1'-phenylethyl)-pyrimidine with 1.0 gm of phosgene and 1.35 ml of triethylamine.

Yield: 3.29 gm of sodium salt (64%).

Rf: 0.69.

IR spectrum: 1770, 1660, 1616, 1550 $cm^{-1}$.

NMR spectrum (DMSO+$CD_3OD$): signals at ppm: 1.5 (6H), 2.15 (3H), 4.1 (1H), 4.65 (1H), 5.4 (q,2H), 5.45 (1H), 6.8 (d,2H), 7.4 (m,7H), 8.50 (1H).

The following are prepared analogously:

D-α-[3-(4-hydroxy-2-{1'-phenylethyl}-5 -pyrimidyl)-ureido]-benzyl-penicillin sodium.

D-α-[3-(2-{1'-p-chlorophenylethyl}-4-hydroxy-5-pyrimidyl)-ureido]-p-hydroxybenzyl-penicillin sodium.

EXAMPLE 56

D-α-[3-(2,4-dihydroxy-5-pyrimidyl)]ureido]-benzyl-penicillin sodium

As in Example 2, 1.3 gm (0.01 mol) of 5-amino-2,4-dihydroxy-pyrimidine are treated with hexamethyl disilazane and phosgene. The product obtained is dissolved in 25 ml of absolute methylene chloride and is droppd at 0° C. into a solution of 4.3 gm of ampicillin triethylammonium salt in 50 ml of absolute methylene chloride. The mixture is stirred for two hours at room temperature. It is then evaporated in vacuo and the solid product obtained is dissolved in a mixture of 50 ml of ethyl acetate and 50 ml of water, the pH value being set at 7.5 with triethylamine. The aqueous phase is separated, covered with a layer of 50 ml of ethyl acetate and brought with dilute hydrochoric acid to a pH value of 2.0. The potassium salt is precipitated from the dried ethyl acetate solution with potassium hexanoate.

Yield: 1.5 gm (29% of theory).

IR spectrum: 1770, 1660, 1625, 1555 $cm^{-1}$.

NMR spectrum ($CD_3OD$) signals at ppm: 1.4–1.5 (d,6H), 4.2 (1H), 5.4–5.6 (3H), 7.5 (5H), 8.4 (1H).

EXAMPLE 57

D-α-[3-(2,4-dihydroxy-5-pyrimidyl)-ureido]-p-hydroxybenzylpenicillin sodium.

This penicillin is prepared analogous to Example 56, starting from 4.7 gm of amoxycillin triethylammonium salt as well as the reaction product of 1.3 gm (0.01 mol) of the pyrimidine of Example 56 with 1.05 mg of phosgene and 1.35 ml of triethylamine.

Yield: 1.97 gm of sodium salt (34%).

IR spectrum: 1770, 1650, 1610, 1560 $cm^{-1}$.

NMR spectrum ($CD_3OD$) signals at ppm: 1.5 (6H), 4.15 (1H), 5.35–5.6 (3H), 6.8 (2H), 7.3 (2H), 8.45 (1H).

The following are synthesized analogously:

D-α-[3-(2,4-dihydroxy-5-pyrimidyl)-ureido]-2-thienylmethyl-penicillin sodium.

D-α-[3-(2,4-dihydroxy-5-pyrimidyl)-ureido]-m,p-dihydroxybenzyl-penicillin sodium.

D-α-[3-(2,4-dihydroxy-5-pyrimidyl)-ureido]-m-chloro-p-hydroxybenzyl-penicillin sodium.

EXAMPLE 58

D-α-[3-(4-hydroxy-2-methoxy-5-pyrimidyl)-ureido]-p-hydroxybenzyl-penicillin sodium This penicillin is prepared analogously to Example 1, starting from 8.4 gm of amoxycillin trihydrate (0.02 mol) as well as the reaction product of 2.82 gm of 5-amino-4-hydroxy-2-methoxy-pyrimidine (0.02 mol) with 2.1 gm of phosgene and 2.75 ml of triethylamine.

Yield: 7.5 gm of sodium salt (63%).

Rf: 0.61.

IR spectrum: 1770, 1655, 1610, 1550 $cm^{-1}$.

NMR spectrum ($D_2O$) signals at ppm: 1.55 (6H), 3.85 (3H), 4.15 (1H), 5.3–5.7 (3H), 6.9 (2H), 7.4 (2H), 8.1 (1H).

EXAMPLE 59

D-α-[3-(4-hydroxy-2-methoxy-5-pyrimidyl)ureido]-benzylpenicillin sodium

This penicillin is prepared analogously to Example 1, starting from 4 gm of ampicillin trihydrate (0.01 mol) as well as the reaction product of 1.41 gm (0.01 mol) of 5-amino-4-hydroxy-2-methoxy-pyrimidine with 1.0 gm of phosgene and 1.37 ml of triethylamine.

Yield: 3.41 gm of sodium salt (59%).

IR spectrum: 1770, 1660, 1600 $cm^{-1}$.

NMR spectrum ($D_2O$) signals at ppm: 1.5 (6H), 3.9 (3H), 4.2 (1H), 5.3–5.7 (3H), 7.5 (5H), 8.05 (1H).

The following are synthesized analogously:

D-α-[3-(4-hydroxy-2-methoxy-5-pyrimidyl)-ureido]-m,p-dihydroxybenzyl-penicillin sodium.

D-α-[3-(4-hydroxy-2-methoxy-5-pyrimidyl)-ureido]-m-chloro-p-hydroxybenzyl-penicillin sodium.

EXAMPLE 60

D-α-'3-(2-ethoxy-4-hydroxy-5-pyrimidyl)-ureido]-p-hydroxybenzyl-penicillin sodium 1.0 gm (0.006 mol) of 5-amino-2-ethoxy-4-hydroxy-primidine are treated in 50 mol of absolute tetrahydrofurane with 0.6 gm of triethylamine and 0.6 gm of phosgene. The solid product obtained after filtering and after distillation of the solvent is dissolved in a little tetrahydrofurane and is dropped at 0° C. into a solution of 2.4 gm of amoxycillin trihydrate in 80% aqueous tetrahydrofurane and triethylamine (pH 8.0). Treatment is effected in the conventional way.

Yield: 2.2 gm (63% of theory).

Rf: 0.66.

IR spectrum: 1770, 1670, 1620, 1560 $cm^{-1}$.

NMR spectrum ($D_2O$) signals at ppm: 1.4 (3H), 1.5 (3H), 1.6 (3H), 4.2 (1H), 4.4 (2H), 5.3 (1H), 5.5 (2H), 6.8 (2H), 7.3 (2H), 8.1 (1H).

The following are synthesized analogously:

D-α-[3-(2-ethoxy-4-hydroxy-5-pyrimidyl)-ureido]-benzylpenicillin sodium.

D-α-[3-(2-ethoxy-4-hydroxy-5-pyrimidyl)-ureido]-cyclohexa-1,4-dien-1-yl-methyl-penicillin sodium.

D-α-[3(2-ethoxy-4-hydroxy-5-pyrimidyl)-ureido]-m,p-dihydroxybenzyl-penicillin sodium.

D-α-[3-(2-ethoxy-4-hydroxy-5-pyrimidyl)-ureido]-m-chloro-p-hydroxybenzyl-penicillin sodium.

EXAMPLE 61

D-α-[3-(4-hydroxy-2-phenoxy-5-pyrimidyl)-ureido]-p-hydroxybenzyl-penicillin sodium This penicillin is prepared analogously to Example 1, starting from 4.2 gm of amoxycillin trihydrate (0.01 mol) as well as the reaction product of 1.92 gm (0.01 mol) of 5-amino-4-hydroxy-2-phenoxy-pyrimidine with 1.0 gm of phosgene and 1.35 ml of triethylamine.

Yield: 4.6 gm of sodium salt (68%).

IR spectrum: 1770, 1660, 1610 $cm^{-1}$.

NMR spectrum (DMSO+$CD_3OD$) signals at ppm: 1.5 (6H), 4.0 (1H), 5.4 (2H), 5.5 (1H), 6.8 (2H), 7.3 (7H).

EXAMPLE 62

D-α-[3-(4-hydroxy-2-methylmercapto-5-pyrimidyl)-ureido]-p-hydroxybenzyl-penicillin sodium This penicillin is prepared analogously to Example 1, starting from 4,2 gm of amoxycillin trihydrate (0.01 mol) as well as the reaction product of 1.48 gm (0.01 mol of 5-amino-4-hydroxy-2-methylmercapto-pyrimidine with 1.0 gm of phosgene and 1.35 ml of triethylamine.

Yield: 4.7 gm of sodium salt (77%).

Rf: 0.76.

IR spectrum: 1770, 1660, 1600, 1530 $cm^{-1}$.

NMR spectrum (DMSO+$CD_3OD$) signals at ppm: 1.55 (6H), 2.5 (3H), 4.05 (1H), 5.5 (q,2H), 5.55 (1H), 7.1 (4H), 8.5 (1H).

EXAMPLE 63

D-α-[3-(4-hydroxy-2-methylmercapto-5-pyrimidyl)-ureido]-benzyl-penicillin sodium This penicillin is prepared analogous to Example 1, starting from 4.0 gm (0.01 mol) of ampicillin trihydrate as well as the reaction product of 1.58 gm (0.01 mol) of 5-amino-4-hydroxy-2-methylmercaptopyrimidine with 1.0 gm of phosgene and 1.35 ml of triethylamine.

Yield: 4.13 gm of sodium salt (70%).

Rf: 0.78.

IR spectrum: 1770, 1660, 1610, 1540 $cm^{-1}$.

NMR spectrum (DMSO+$CO_3OD$) signals at ppm: 1.50 (6H), 2.45 (3H), 4.10 (1H), 5.45 (3H), 7.5 (5H), 8.45 (1H).

EXAMPLE 64

D-α-[3-(4-hydroxy-2-mercapto-5-pyrimidyl)-ureido]-p-hydroxybenzyl-penicillin sodium This penicillin is prepared analogous to Example 1, starting from 2.1 gm of amoxycillin trihydrate (0.005 mol) as well as the reaction product of 0.66 gm (0.005 mol) of 5-amino-4-hydroxy-2-mercapto-pyrimidine with 500 mg of phosgene and 0.67 ml of triethylamine.

Yield: 1.52 gm of sodium salt (51%).

Rf: 0.61.

IR spectrum: 1770, 1665, 1605, 1535 $cm^{-1}$.

NMR spectrum (DMSO+$CD_3OD$) signals at ppm: 1.55 (6H), 4.10 (1H), 5.40 (3H), 6.8 (2H), 7.3 (2H), 8.55 (1H).

EXAMPLE 65

D-α-[3-(4-hydroxy-2-mercapto-5-pyrimidyl)-ureido]-benzyl-penicillin sodium

This penicillin is prepared analogous to Example 1, starting from 2.0 gm of ampicillin trihydrate (0.005 mol) as well as the reaction product of 0.66 gm (0.005 mol) of 5-amino-4-hydroxy-2-mercapto-pyrimidine with 0.005 gm of phosgene and 0.67 ml of triethylamine.

Yield: 1.89 gm of sodium salt (65%).

Rf: 0.58.

IR spectrum: 1770, 1660, 1600, 1525 $cm^{-1}$.

NMR spectrum (DMSO+$CD_3OD$) signals at ppm: 1.55 (6H), 4.10 (1H), 5.35 (q,2H), 5.45 (1H), 7.5 (5), 8.5 (1H).

EXAMPLE 66

D-α-[3-(2-ethylmercapto-4-hydroxy-5-pyrimidyl)]-ureido-p-hydroxybenzyl-penicillin sodium This compound is synthesized analogous to Example 1, starting from 1.1 gm of 2-ethylmercapto-4-hydroxy-5-aminopyrimidine (0.007 mol) and 3.0 gm of amoxycillin trihydrate (0.007 mol).

Yield: 3 gm (69.5% of theory).

Rf: 0.57.

NMR spectrum ($D_2O$) signals at ppm: 1.35 (3H), 1.5 (d,6H), 3.15 (2H), 4.2 (1H), 5.3 (1H), 5.5 (2H), 6.8 (2H), 7.3 (2H), 8.3 (1H).

The following is synthesized analogously:

D-α-[3-(2-ethylmercapto-4-hydroxy-5-pyrimidyl)]-ureidobenzyl-penicillin sodium.

EXAMPLE 67

D-α-[3-(2-p-chlorobenzylmercapto-4-hydroxypyrimidyl)ureido]-p-hydroxybenzyl-penicillin sodium This penicillin is prepared analogous to Example 1, starting from 420 mg of amoxycillin trihydrate (0.001 mol) as well as the reaction product of 260 mg (0.001 mol) of 5-amino-2-p-chlorobenzylmercapto-4-hydroxypyrimidine with 100 mg of phosgene and 0.14 ml of triethylamine.

Yield: 290 mg of sodium salt (41%).

Rf: 0.79.

IR spectrum: 1770, 1650, 1600, 1540 $cm^{-1}$.

NMR spectrum (DMSO+$CD_3OD$) signals at ppm: 1.55 (6H), 3.5 (2H), 4.05 (1H), 5.5 (3H), 6.8 (2H), 7.4 (6H), 8.5 (1H).

The following are prepared analogously:

D-α-[3-(2-butoxy-4-hydroxy-5-pyrimidyl)-ureido]-p-hydroxybenzyl-penicillin sodium.

D-α-[3-(2-allyloxy-4-hydroxy-5-pyrimidyl)-ureido]-p-hydroxybenzyl-penicillin sodium.

D-α-[3-(2-cyclopropyloxy-4-hydroxy-5-pyrimidyl)-ureido]-p-hydroxybenzyl-penicillin sodium.

D-α-[3-(2-cylcohexyloxy-4-hydroxy-5-pyrimidyl)-ureido]-p-hydroxybenzyl-penicillin sodium.

D-α-[3-(2-benzyloxy-4-hydroxy-5-pyrimidyl)-ureido]-p-hydroxybenzyl-penicillin sodium.

EXAMPLE 68

D-α-[3-(4-hydroxy-2-methylsulphinyl-5-pyrimidyl)-ureido]-p-hydroxybenzyl-penicillin sodium This penicillin is prepared analogous to Example 1, starting from 2.1 gm of amoxycillin trihydrate (0.005 mol) as well as the reaction product of 0.85 gm (0.005 mol) of 5-amino-4-hydroxy-2-methylsulphinyl-pyrimidine with 500 mg of phosgene and 0.67 ml of triethylamine.

Yield: 1.7 gm of sodium salt (58%).

Rf: 0.41.

IR spectrum: 1770, 1650, 1610, 1530 $cm^{-1}$.

NMR spectrum (DMSO+CD+OD) signals at ppm: 1.5 (6H), 2.7 (3H), 4.0 (1H), 5.4 (2H), 5.5 (1H), 6.75 (2H), 7.3 (2H), 8.7 (1H).

EXAMPLE 69

D-α-[3-(2-ethylsulphinyl-4-hydroxy-5-pyrimidyl)-ureido]-p-hydroxybenzyl-penicillin sodium This penicillin is prepared analogous to Example 1, starting from 3.12 gm of amoxycillin trihydrate (0.0073 mol) as well as the reaction produce of 1.36 gm (0.0073 mol) of 5-amino-2-ethylsulphinyl-4-hydroxy-pyrimidine with 750 mg of phosgene and 1.0 ml of triethylamine.

Yield: 2.2 gm of sodium salt (53.5%).

Rf: 0.45.

IR spectrum: 1770, 1660, 1600, 1550, 1510 $cm^{-1}$.

NMR spectrum ($D_2O$) signals at ppm: 1.2 (3H), 1.5 (6H), 3.15 (2H), 4.25 (1H), 5.3 (2H), 5.45 (1H), 6.8 (2H), 7.3 (2H), 8.7 (1H).

The following are prepared analogously:

D-α-[3-(4-hydroxy-2-methylsulphonyl-5-pyrimidyl)-ureido]-p-hydroxybenzyl-penicillin sodium.

D-α-[3-(4-hydroxy-2-methylsulphonyl-5-pyrimidyl)-ureido]-benzyl-penicillin sodium.

D-α]3-(2-ethylsulphonyl-4-hydroxy-5-pyrimidyl)-ureido]-p-hydroxybenzyl-penicillin sodium.

EXAMPLE 70

D-α-[3-(4-hydroxy-2-phenethyl-5-pyrimidyl)-ureido]-p-hydroxybenzyl-penicillin sodium This penicillin is prepared analogous to Example 1, starting from 2.1 gm of amoxycillin trihydrate (0.005 mol) as well as the reaction product of 1.07 gm (0.005 mol) of 5-amino-4-hydroxy-2-phenethyl-pyrimidine with 0.5 gm of phosgene and 0.67 ml of triethylamine.

Yield: 2.14 gm of sodium salt (68%).

Rf: 0.76.

IR spectrum: 1770, 1650, 1600, 1540 $cm^{-1}$.

NMR spectrum (DMSO+$CD_3OD$) signals at ppm: 1.55 (6H), 3.0 (4H), 4.1 (1H), 5.5 (3H), 6.85 (2H), 7.4 (7H), 8.6 (1H).

EXAMPLE 71

D-α-[3-(4-hydroxy-2-{3'-phenylpropyl}-5-pyrimidyl)-ureido]-p-hydroxybenzyl-penicillin sodium This penicillin is prepared analogous to Example 1, starting from 2.1 gm of amoxycillin trihydrate (0.005 mol) as well as the reaction product of 1.15 gm (0.005 mol) of 5-amino-5-hydroxy-2-(3'-phenylpropyl)-pyrimidine with 0.5 gm of phosgene and 0.67 ml of triethylamine.

Yield: 2.31 gm of sodium salt (72%).

Rf: 0.79.

IR spectrum: 1765, 1650, 1600, 1550 $cm^{-1}$.

NMR spectrum ($D_2O$) signals at ppm: 1.5 (6H), 1.9 (2H), 2.5 (4H), 4.25 (1H), 5.45 (3H), 6.9 (7H), 7.3 (2H), 8.3 (1H).

EXAMPLE 72

D-α-[3-(4-hydroxy-2-{2'-phenylethylidene}-5-pyrimidyl)-ureido]-p-hydroxybenzyl-penicillin sodium This penicillin is prepared analogous to Example 1, starting from 2.1 gm of amoxycillin trihydrate (0.005 mol) as well as the reaction product of 1.06 gm of 5-amino-4-hydroxy-2-(2'-phenylethylidene)-pyrimidine with 500 mg of phosgene and 0.67 ml of triethylamine.

Yield: 1.82 gm of sodium salt (58%).

IR spectrum: 1770, 1650, 1600, 1540, 1510 $cm^{-1}$.

NMR spectrum (DMSO+$CD_3OD$) signals at ppm: 1.55 (6H), 4.0 (1H), 5.45 (q,2H), 5.55 (1H), 6.8 (2H), 7.0–8.0 (m,9H).

EXAMPLE 73

D-α-[3-(4-hydroxy-2-methylamino-5-pyrimidyl)-ureido]-p-hydroxybenzyl-penicillin sodium This penicillin is prepared analogous to Example 11, starting from 1.68 gm (0.004 mol) of amoxycillin trihydrate as well as the reaction product of 560 mg (0.004 mol) of 5-amino-4-hydroxy-2-methylamino-pyrimidine with 400 mg of phosgene and 0.54 ml of triethylamine.

Yield: 940 mg of sodium salt (43.5%).

Rf: 0.45.

IR spectrum: 1770, 1650, 1600, 1530 $cm^{-1}$.

NMR spectrum (DMSO+$CD_3OD$) signals at ppm: 1.55 (6H), 2.75 (3H), 4.0 (1H), 5.4 (3H), 6.75 (2H), 7.25 (2H), 8.1 (1H).

EXAMPLE 74

D-α-[3-(4-hydroxy-2-methylamino-5-pyrimidyl)-ureido]-benzyl-penicillin sodium

This penicillin is prepared analogous to Example 73, starting from 375 mg of ampicillin sodium salt (0.001 mol) as well as the reaction product of 140 mg of the pyrimidine of Example 73 with 100 mg of phosgene and 0.14 ml of triethylamine.

Yield: 230 mg of sodium salt (43%).

Rf: 0.41.

IR spectrum: 1770, 1630, 1540 $cm^{-1}$.

NMR spectrum (DMSO+$CD_3OD$) signals at ppm: 1.55 (6H), 2.70 (3H), 4.05 (1H), 5.45 (3H), 7.35 (5H), 8.15 (1H).

EXAMPLE 75

D-α-[3-(2-amino-4-hydroxy-5-pyrimidyl)-ureido]-p-hydroxybenzyl-penicillin sodium 1.26 gm (0.01 mol) of 2,5-diamino-4-hydroxy-pyrimidine are refluxed for 3 hours with 20 ml of hexamethyl disilazane, nitrogen being introduced slowly. A yellow solution is obtained. Hexamethyldisilazane is then blown off with nitrogen. The remaining oil product is dissolved in 40 ml of absolute tetrahydrofurane and dropped with ice-cooling into a solution of 1.0 gm of phosgene in 20 ml of absolute tetrahydrofuran. After addition, the ice bath is removed and nitrogen is blown through the solution to remove excess phosgene.

4.2 gm of amoxycillin trihydrate are dissolved with 2.5 ml of triethylamine in 70 ml of absolute dimethylformamide, 2 gm of magnesium sulphate are added thereto and the mixture is stirred for 1 hour at room temperature. The filtered solution is dropped with ice-bath cooling into the solution prepared above. The mixture is stirred for 2 hours at room temperature and then evaporated to dryness in vacuo. 50 ml of water and 50 ml of ethyl acetate are then added thereto and the pH value is adjusted to 7.0. The aqueous phase is shaken once again with ethyl acetate. The aqueous phase is then brought with 2N hydrochloric acid to pH 2.8 with cooling. The precipitated product is filtered off, washed with a littel ice-cold water and dried. The sodium salt is prepared with sodium hexanoate in methanol/ether.

Yield: 1.45 gm of sodium salt (29%).

Rf: 0.34.

IR spectrum: 1770, 1660, 1605, 1535 $cm^{-1}$.

NMR spectrum (DMSO+$CD_3OD$) signals at ppm: 1.55 (6H), 4.05 (1H), 5.45 (3H), 6.8 (2H), 7.3 (2H), 8.1 (1H).

The following are prepared analogously:

D-α-[3-(2-amino-4-hydroxy-5-pyrimidyl)-ureido]-cyclohexa-1,4-dien-1-yl-methyl-penicillin sodium.

D-α-[3-(2-amino-4-hydroxy-5-pyrimidyl)-ureido]-2-thienylmethyl-penicillin sodium.

D-α-[3-(2-amino-4-hydroxy-5-pyrimidyl)-ureido]-m,p-dihydroxybenzyl-penicillin sodium.

D-α-[3-(2-amino-4-hydroxy-5-pyrimidyl)-ureido]-m-chloro-p-hydroxybenzyl-penicillin sodium.

EXAMPLE 76

D-α-[3-(2-ethylamino-4-hydroxy-5-pyrimidyl)-ureido]-p-hydroxybenzyl-penicillin sodium This penicillin is prepared analogously to Example 11, starting from 6.3 gm (0.015 mol) and amoxycillin trihydrate as well as the reaction product of 2.31 gm (0.015 mol) of 5-amino-2-ethylamino-4-hydroxy-pyrimidine with 1.5 gm of phosgene and 2.05 ml of triethylamine.

Yield: 4.9 gm of sodium salt (57.5%).

Rf: 0.46.

IR spectrum: 1770, 1650, 1530 $cm^{-1}$.

NMR spectrum (DMSO+$CD_3OD$) signals at ppm: 1.5 (9H), 3.1 (2H), 4.0 (1H), 5.4 (q,2H), 5.5 (1H), 6.75 (2H), 7.25 (2H), 8.1 (1H),

EXAMPLE 77

D-α-[3-(2-ethylamino-4-hydroxy-5-pyrimidyl)-ureido]-benzyl-penicillin sodium

This penicillin is prepared analogously to Example 76, starting from 3.75 gm of ampicillin sodium (0.01 mol) as well as the reaction product of 1.53 gm of the pyrimidine of Example 76 (0.01 mol) with 1.0 gm of phosgene and 1.35 ml of triethylamine.

Yield: 2.48 gm of sodium salt (51%).

Rf: 0.49.

IR spectrum: 1770, 1660, 1610, 1555 $cm^{-1}$.

NMR spectrum (DMSO+$CD_3OD$) signals at ppm: 1.50 (3H), 1.55 (6H), 3.1 (2H), 4.05 (1H), 5.45 (3H), 7.4 (5H), 8.15 (1H).

EXAMPLE 78

D-α-[3-(2-ethylamino-4-hydroxy-5-pyrimidyl)-ureido-cyclohexa-1,4-dien-1-yl-methyl-penicillin sodium salt This penicillin is prepared analogous to Example 76, starting from 3.75 gm of epicillin sodium (0.01 mol) as well as the reaction product of 1.53 gm of the pyrimidine of Example 76 (0.01 mol) with 1.0 gm of phosgene and 1.35 ml of triethylamine.

Yield: 2.66 gm of sodium salt (48%).

IR spectrum: 1770, 1650, 1610, 1535 $cm^{-1}$.

NMR spectrum (DMSO+$CD_3OD$) signals at ppm: 1.55 (9H), 2.50 (4H), 3.1 (2H), 4.0 (1H), 4.90 (1H), 5.35 (2H), 5.65 (3H), 8.15 (1H).

EXAMPLE 79

D-α-[3-(4-hydroxy-2-propylamino-5-pyrimidyl)-ureido]-p-hydroxybenzyl-penicillin sodium This penicillin is prepared analogously to Example 11, starting from 2.1 of amoxycillin trihydrate (0.005 mol) as well as the reaction product of 0.84 gm of 5-amino-4-hydroxy-2-propylamino-pyrimidine (0.005 mol) with 0.5 gm of phosgene and 0.68 ml of triethylamine.

Yield: 1.69 gm of sodium salt (58%).

IR spectrum: 1770, 1650, 1610, 1535 $cm^{31\ 1}$.

NMR spectrum (DMSO+$CD_3OD$) signals at ppm: 1.2 (3H), 1.55 (6H), 1.9 (2H), 3.2 (2H), 4.05 (1H), 5.4 (3H), 6.8 (2H), 7.3 (2H), 8.15 (1H).

EXAMPLE 80

D-α-[3-(4-hydroxy-2-propylamino-5-pyrimidyl)-ureido]-benzyl-penicillin sodium

This penicillin is prepared analogous to Example 11, starting from 2.0 gm of ampicillin trihydrate (0.005 mol) as well as the reaction product of 0.84 gm of the pyrimidine of Example 79 (0.005 mol) with 0.5 gm of phosgene and 0.68 ml of triethylamine.

Yield: 1.51 gm of sodium salt (54%).

IR spectrum: 1765, 1650, 1605, 1545 $cm^{-1}$.

NMR spectrum (DMSO+$CD_3OD$) signals at ppm: 1.25 (3H), 1.5 (6H), 1.9 (2H), 3.25 (2H), 4.0 (1H), 5.35 (q,2H), 5.45 (1H), 7.5 (5H), 8.1 (1H).

EXAMPLE 81

D-α-[3-(4-hydroxy-2-isopropylamine-5-pyrimidyl)-ureido]-p-hydrobenzyl-penicillin sodium This penicillin is prepared analogously to Example 11, starting from 2.52 gm of amoxycillin trihydrate (0.006 mol) as well as the reaction product of 1.02 gm of 5-amino-4-hydroxy-2-isopropylamino-pyrimidine (0.006 mol) with 600 mg of phosgene and 0.82 ml of triethylamine.

Yield: 2.17 gm of sodium salt (62%).

IR spectrum (DMSO+$CD_3OD$) signals at ppm: 1.2 (6H), 1.55 (6H), 3.6 (1H), 4.05 (1H), 5.35 (2H), 5.45 (1H), 6.85 (2H), 7.35 (2H), 8.20 (1H).

EXAMPLE 82

D-α-[3-(4-hydroxy-2-isopropylamino-5-pyrimidyl)-ureido]-benzyl-penicillin sodium This penicillin is prepared analogous to Example 11, starting from 4.0 gm of ampicillin trihydrate (0.01 mol) as well as the reaction product of 1.68 gm of the pyrimidine of Example 81 with 1.0 gm of phosgene and 1.35 ml of triethylamine.

Yield: 3.62 gm of sodium salt (64%).

IR spectrum: 1765, 1655, 1610, 1540 $cm^{-1}$.

NMR spectrum (DMSO+$CD_3OD$) signals at ppm: 1.2 (6H), 1.5 (6H), 3.65 (1H), 4.0 (1H), 5.35 (2H), 5.45 (1H), 7.45 (5H), 8.15 (1H).

EXAMPLE 83

D-α-[3-(4-hydroxy-2-isobutylamino-5-pyrimidyl)-ureido]-p-hydroxybenzyl-penicillin sodium.

This penicillin is prepared analogous to Example 11, starting from 1.68 gm of amoxycillin trihydrate (0.004 mol) as well as the reaction product of 650 mg (0.004 mol) of 5-amino-4-hydroxy-2-isobutylamino-pyrimidine with 400 mg of phosgene and 0.54 ml of triethylamine.

Yield: 1.55 gm of sodium salt (65%).

IR spectrum: 1770, 1650, 1610, 1540 $cm^{-1}$.

NMR spectrum (DMSO+$CD_3OD$) signals at ppm: 1.0 (6H), 1.55 (6H), 1.8 (1H), 3.0 (2H), 4.05 (1H), 5.4 (3H), 6.8 (2H), 7.25 (2H), 8.2 (1H).

EXAMPLE 84

D-α-[3-(4-hydroxy-2-isobutylamino-5-pyrimidyl)-ureido]-benzyl-penicillin sodium

This penicillin is prepared analogous to Example 11, starting from 2.0 gm of ampicillin trihydrate (0.005 mol) as well as the reaction product of 0.91 gm of the pyrimidine of Example 83 (0.005 mol) with 0.5 gm of phosgene and 1.35 ml of triethylamine.

Yield: 1.66 gm of sodium salt (57%)

IR spectrum: 1765, 1655, 1610, 1545 $cm^{-1}$.

NMR spectrum (DMSO+$CD_3OD$) signals at ppm: 1.0 (6H), 1.5 (6H), 1.85 (1H), 3.1 (2H), 4.0 (1H), 5.45 (3H), 7.45 (5H), 8.15 (1H).

EXAMPLE 85

D-α-[3-(2-butylamino-4-hydroxy-5-pyrimidyl)-ureido]-p-hydroxybenzyl-penicillin sodium.

This penicillin is prepared analogously to Example 11, starting from 4.2 gm (0.01 mol) of amoxycillin trihydrate as well as the reaction product of 1.82 gm of 5-amino-2-butylamino-4-hydroxy-pyrimidine (0.01 mol) with 1.0 gm of phosgene and 1.35 ml of triethylamine.

Yield: 2.85 gm of sodium salt (49%).

IR spectrum: 1765, 1655, 1610, 1540 $cm^{-1}$.

NMR spectrum (DMSO+$CD_3OD$) signals at ppm: 0.9 (3H), 1.4 (6H), 1.5 (6H), 3.0 (2H), 4.05 (1H), 5.45 (3H), 6.8 (2H), 7.35 (2H), 8.2 (1H).

EXAMPLE 86

D-α-[3-(2-butylamino-4-hydroxy-5-pyrimidyl)-ureido]-benzyl-penicillin sodium

This penicillin is prepared analogous to Example 85, starting from 4.0 gm of ampicillin trihydrate as well as the reaction product of 1.82 gm (0.01 mol) of the pyrimidine of Example 85 with 1.0 gm of phosgene and 1.35 ml of triethylamine.

Yield: 3.02 gm of sodium salt (52%).

IR spectrum: 1765, 1650, 1610, 1535 $cm^{-1}$.

NMR spectrum (DMSO+$CD_3OD$) signals at ppm: 0.9 (3H), 1.5 (10H), 2.9 (2H), 4.0 (1H), 5.4 (3H), 7.45 (5H), 8.15 (1H).

EXAMPLE 87

D-α-[3-(2-hexylamino-4-hydroxy-5-pyrimidyl)-ureido]-p-hydroxybenzyl-penicillin sodium This penicillin is prepared analogous to Example 11, starting from 1.26 gm of amoxycillin trihydrate (0.003 mol) as well as the reaction product of 625 mg. (0.003 mol) of 5-amino-2-hexylamino-4-hydroxy-pyrimidine with 300 mg of phosgene and 0.4 ml of triethylamine.

Yield: 1.05 gm of sodium salt (54%).

IR spectrum: 1770, 1665, 1610, 1520 $cm^{-1}$.

NMR spectrum (DMSO+$CD_3OD$) signals at ppm: 0.9 (3H), 1.2–1.8 (14H), 3.3 (2H), 4.0 (1H), 5.35 (2H), 5.45 (1H), 6.85 (2H), 7.35 (2H), 8.15 (1H).

EXAMPLE 88

D-α-[3-(4-hydroxy-2-octylamino-5-pyrimidyl)-ureido]-p-hydroxybenzyl-penicillin sodium This penicillin is prepared analogous to Example 11, starting from 420 mg of amoxycillin trihydrate (0.01 mol) as well as the reaction product of 240 mg of 5-amino-4-hydroxy-2-octylamino-pyrimidine with 100 mg of phosgene and 0.14 ml of triethylamine.

Yield: 205 gm of sodium salt (34%).

IR spectrum: 1770, 1670, 1620, 1550 $cm^{-1}$.

NMR spectrum (DMSO+$CD_3OD$) signals at ppm: 0.9 (3H), 1.3–1.8 (18H), 3.3 (2H), 4.1 (1H), 5.45 (3H), 6.8 (2H), 7.3 (2H), 8.15 (1H).

The following are synthesized analogously.

D-α-[3-(4-hydroxy-2-methylamino-5-pyrimidyl)-ureido]-cyclohexa-1,4-dien-1-yl-methyl penicillin sodium.

D-α-[3-(4-hydroxy-2-methylamino-5-pyrimidyl)-ureido]-2-thienylmethyl-penicillin sodium.

D-α-[3-(4-hydroxy-2-methylamino-5-pyrimidyl)-ureido]-m,p-dihydroxybenzyl-penicillin sodium.

D-α[3-(4-hydroxy-2-methylamino-5-pyrimidyl)-ureido]-m-chloro-p-hydroxybenzyl-penicillin sodium.

D-α-[3-(2-ethylamino-4-hydroxy-5-pyrimidyl]-2-thienyl]-methyl-penicillin sodium.

D-α-[3-(2-ethylamino-4-hydroxy-5-pyrimidyl)-ureido]-m,p-dihydroxybenzyl-penicillin sodium.

D-α-[3-(2-ethylamino-4-hydroxy-5-pyrimidyl)-ureido]-m-chloro-p-hydroxybenzyl-penicillin sodium.

D-α-[3-(4-hydroxy-2-isopropylamino-5-pyrimidyl)-ureido]-cyclohexa-1,4-dien-1-yl-penicillin sodium.

D-α-[3-(4-hydroxy-2-isopropylamino-5-pyrimidyl)-ureido]-m,p-dihydroxybenzyl-penicillin sodium.

D-α-[3-(4-hydroxy-2-propylamino-5-pyrimidyl)-ureido]-m-chloro-p-hydroxybenzyl-penicillin sodium.

D-α-[3-(4-hydroxy-2-sec-butylamino-5-pyrimidyl)-ureido]-p-hydroxybenzyl-penicillin sodium.

D-α-[3-(4-hydroxy-2-isobutylamino-5-pyrimidyl)-ureido]-m-chloro-p-hydroxybenzyl-penicillin sodium.

D-α-[3-(4-hydroxy-2-isobutylamino-5-pyrimidyl)-ureido]-m,p-dihydroxybenzyl-penicillin sodium.

D-α-[3-(2-t-butylamino-4-hydroxy-5-pyrimidyl)-ureido]-p-hydroxybenzyl-penicillin sodium.

D-α-[3-(2-t-butylamino-4-hydroxy-pyrimidyl)-ureido]-benzyl-penicillin sodium.

D-α-[3-(2-hexylamino-4-hydroxy-5-pyrimidyl)-ureido]-benzyl-penicillin sodium.

EXAMPLE 89

D-α-[3-(2-allylamino-4-hydroxy-5-pyrimidyl)-ureido]-p-hydroxybenzyl-penicillin sodium This penicillin is prepared analogous to Example 11, starting from 2.1 gm of amoxycillin trihydrate (0.005 mol) as well as the reaction product of 840 mg (0.005 mol) of 2-allylamino-5-amino-4-hydroxy-pyrimidine with 500 mg of phosgene and 0.67 ml of triethylamine.

Yield: 1.92 gm of sodium salt (66%).

IR spectrum: 1770, 1660, 1610, 1550 1510 $cm^{-1}$.

NMR spectrum (DMSO+$CD_3OD$) signals at ppm: 1.5 (6H), 3.9 (2H), 3.95 (1H), 5.0–5.6 (m,5H), 5.9 (m,1H), 6.75 (2H), 7.25 (2H), 8.1 (1H).

EXAMPLE 90

D-α-[3-(2-allylamino-4-hydroxy-5-pyrimidyl)-ureido]-benzyl-penicillin sodium

This penicillin is prepared analogous to Example 89, starting from 1.85 gm of ampicillin sodium (0.005 mol) as well as the reaction product of 840 mg of the pyrimidine of Example 89 with 500 mg of phosgene and 0.67 ml of triethylamine.

Yield: 1.7 gm of sodium salt (60%).

IR spectrum: 1770, 1660, 1610, 1550 $cm^{-1}$.

NMR spectrum (DMSO+$CD_3OD$) signals at ppm: 1.5 (6H), 3.95 (2H), 4.0 (1H), 5.0–5.5 (m,5H), 6.0 (m,1H), 7.4 (5H), 8.1 (1H).

EXAMPLE 91

D-α-[3-(2-allylamino-4-hydroxy-5-pyrimidyl)-ureido]-cyclohexa-1,4-dien-1-yl-methyl-penicillin sodium This penicillin is prepared analogous to Example 89, starting from 3.75 gm of epicillin sodium (0.01 mol) as well as the reaction product of 1.66 gm of the amine of Example 89 with 1.0 gm of phosgene and 1.35 ml of triethylamine.

Yield: 3.5 gm of sodium salt (64%).

IR spectrum: 1765, 1655, 1605, 1550 $cm^{-1}$.

NMR spectrum (DMSO+$CD_3OD$) signals at ppm: 1.5 (6H), 2.55 (4H), 3.9 (2H), 4.05 (1H), 4.95 (1H), 5.0–5.7 (m,7H), 6.0 (1H), 8.1 (1H).

EXAMPLE 92

D-α-[3-(2-crotylamino-4-hydroxy-5-pyrimidyl)-ureido]-p-hydroxybenzyl-penicillin sodium This penicillin is prepared analogous to Example 11, starting from 4.2 gm of amoxycillin trihydrate (0.01 mol) as well as the reaction product of 1.8 gm of 5-amino-2-crotylamino-4-hydroxy-pyrimidine with 1.0 gm of phosgene and 1.37 ml of triethylamine.

Yield: 3.27 gm of sodium salt (55%).

IR spectrum: 1770, 1660, 1615, 1550 $cm^{-1}$.

NMR spectrum (DMSO+$CD_3OD$) signals at ppm: 1.5 (9H), 3.8 (2H), 4.0 (1H), 5.5 (m,5H), 6.8 (2H), 7.35 (2H), 8.2 (1H).

EXAMPLE 93

D-α-[3-(2-crotylamino-4-hydroxy-5-pyrimidyl)-ureido]-benzyl-penicillin sodium

This penicillin is prepared analogous to Example 11, starting from 3.7 gm of ampicillin sodium (0.01 mol) as well as the reaction product of 1.8 gm of the amine of Example 92 (0.01 mol) with 1.0 gm of phosgene and 1.37 ml triethylamine.

Yield: 3.55 gm of sodium salt (59%).

IR spectrum: 1770, 1660, 1610, 1555 $cm^{-1}$.

NMR spectrum (DMSO+$CD_3OD$) signals at ppm: 1.55 (9H), 3.75 (2H), 4.05 (1H), 5.3-5.9 (m,5H), 7.45 (5H), 8.15 (1H).

EXAMPLE 94

D-α-[3-(4-hydroxy-2-propargylamino-5-pyrimidyl)-ureido]-p-hydroxy-benzyl-penicillin sodium This penicillin is prepared analogous to Example 11, starting from 8.4 gm of amoxycillin trihydrate (0.02 mol) as well as the reaction product of 3.28 gm (0.02 mol) of 5-amino-4-hydroxy-2-propargylamino-pyrimidine with 2.05 gm of phosgene and 2.70 ml of triethylamine.

Yield: 6.95 gm of sodium salt (60%).

IR spectrum: 1765, 1655, 1610, 1540 $cm^{-1}$.

NMR spectrum ($D_2O$) signals at ppm: 1.5 (6H), 2.6 (1H), 3.9 (1H), 4.15 (2H), 5.5 (3H), 6.9 (2H), 7.3 (2H), 8.05 (1H).

EXAMPLE 95

D-α-[3-(4-hydroxy-2-propargylamino-5-pyrimidyl)-ureido]-benzyl-penicillin sodium This penicillin is prepared analogous to Example 11, starting from 3.7 gm of ampicillin sodium (0.01 mol) as well as the reaction product of 1.64 gm (0.01 mol) of 5-amino-4-hydroxy-2-propargylamino-pyrimidine with 1.05 gm of phosgene and 1.37 ml of triethylamine.

Yield: 2.85 gm of sodium salt (50%).

IR spectrum: 1765, 1650, 1605, 1545 $cm^{-1}$.

NMR spectrum ($D_2O$) signals at ppm: 1.55 (6H), 2.55 (1H), 3.95 (1H), 4.15 (2H), 5.45 (3H), 7.5 (5H), 8.1 (1H).

The following are synthesized analogously:

D-α-[3-(2-allylamino-4-hydroxy-5-pyrimidyl)-ureido]-2-thienylmethyl-penicillin sodium.

D-α-[3-(2-allylamino-4-hydroxy-5-pyrimidyl)-ureido]-m,p-dihydroxy-benzyl-penicillin sodium.

D-α-[3-(2-allylamino-4-hydroxy-5-pyrimidyl)-unreido]-m-chloro-p-hydroxybenzyl-penicillin sodium.

D-α-[3-(2-crotonylamino-4-hydroxy-5-pyrimidyl)-ureido]-m,p-dihydroxybenzyl-penicillin sodium.

D-α-[3-(2-crotonylamino-4-hydroxy-5-pyrimidyl)-ureido]-m-chloro-p-hydroxybenzyl-penicillin sodium.

D-α-[3-(4-hydroxy-2-propargylamino-5-pyrimidyl)-ureido]-cyclohexa-1,4-dien-1-yl-methyl-penicillin sodium.

D-α-[3-(4-hydroxy-2-propargylamino-5-pyrimidyl)-ureido]-2-thienylmethyl-penicillin sodium.

D-α-[3-(4-hydroxy-2-propargylamino-5-pyrimidyl)-ureido]-m,p-dihydroxybenzyl-penicillin sodium.

D-α-[3-(4-hydroxy-2-propargylamino-5-pyrimidyl)-ureido]-m-chloro-p-hydroxybenzyl-penicillin sodium.

D-α-[3-(4-hydroxy-2-octen(3)-ylamino-5-pyrimidyl)-ureido]-p-hydroxybenzyl-penicillin sodium.

D-α-[3-(4-hydroxy-2-pentin(3)-yl(2)-amino-5-pyrimidyl)-ureido]-p-hydroxybenzyl-penicillin sodium.

EXAMPLE 96

D-α-[3-(2-dimethylamino-4-hydroxy-5-pyrimidyl)-ureido]-p-hydroxy-benzyl-penicillin sodium This penicillin is prepared analogous to Example 49, starting from 1.58 gm of 6-aminopenicillanic acid triethylammonium salt (0.005 mol) as well as the reaction product of 1.74 gm of D-α-[3-(2-dimethylamino-4-hydroxy-5-pyrimidyl)-ureido]-p-hydroxyphenylglycine (0.005 mol) with 500 mg of N-methylmorpholine (0.005 mol) and 550 mg of ethylchloroformate (0.005 mol).

Yield: 1.62 gm of sodium salt (57%).

Rf: 0.46.

IR spectrum: 1765, 1660, 1610, 1550, 1530 $cm^{-1}$.

NMR spectrum (DMSO+$CD_3OD$) signals at ppm: 1.55 (6H), 3.1 (6H), 4.05 (1H), 5.4 (q,2H), 5.5 (1H), 6.85 (2H), 7.35 (2H), 8.2 (1H).

EXAMPLE 97

D-α-[3-(2-dimethylamino-4-hydroxy-5-pyrimidyl)-ureido]-benzyl-penicillin sodium

This penicillin is prepared analogous to Example 49, starting from 3.16 gm of 6-aminopenicillanic acid triethylammonium salt (0.01 mol) as well as the reaction product of 3.32 gm (0.01 mol) of D-α-[3-(2-dimethylamino-4-hydroxy-5-pyrimidyl)-ureido]-phenylglycine (0.01 mol) with 1.0 gm of N-methylmorpholine and 1.1 gm of ethylchloroformate (0.01 mol).

Yield: 2.52 gm of sodium salt (46%).

Rf: 0.44.

IR spectrum: 1770, 1660, 1610, 1555 $cm^{-1}$.

NMR spectrum (DMSO+$CD_3OD$) signals at ppm: 1.55 (6H), 3.05 (2H), 4.05 (1H), 5.35 (2H), 5.45 (1H), 7.4 (5H), 8.25 (1H).

EXAMPLE 98

D-α-[3-(2-diethylamino-4-hydroxy-5-pyrimidyl)-ureido]-p-hydroxybenzyl-penicillin sodium This penicillin is prepared analogously to Example 11, starting from 1.26 gm (0.003 mol) of amoxycillin trihydrate as well as the reaction product of 545 mg (0.003 mol) of 5-amino-2-diethylamino-4-hydroxypyrimidine with 300 mg of phosgene and 0.41 ml of triethylamine.

Yield: 1.26 gm of sodium salt (70%).

Rf: 0.51.

IR spectrum: 1770, 1665, 1620, 1560 $cm^{-1}$.

NMR spectrum (DMSO+$CD_3OD$) signals at ppm: 1.4 (6H), 1.6 (6H), 3.5 (4H), 4.1 (1H), 5.5 (3H), 6.9 (2H), 7.35 (2H), 8.15 (1H).

EXAMPLE 99

D-α-[3-(2-diallylamino-4-hydroxy-5-pyrimidyl)-ureido]-p-hydroxybenzyl-penicillin sodium This penicillin is prepared analogous to Example 11, starting from 2.1 gm (0.005 mol) of amoxycillin trihydrate as well as the reaction product of 1.02 gm of 5-amino-2-diallylamino-4-hydroxy-pyrimidine (0.005 mol) with 500 mg of phosgene and 0.67 ml of triethylamine.

Yield: 1.97 gm of sodium salt (63.5%).

IR spectrum: 1765, 1665, 1615, 1540 $cm^{-1}$.

NMR spectrum (DMSO+$CD_3OD$) signals at ppm: 1.5 (6H), 4.0 (1H), 4.1 (4H), 5.1 (4H), 5.4 (q,2H), 5.5 (1H), 6.0 (m,2H), 6.8 (2H), 7.3 (2H), 8.1 (1H).

The following are synthesized analogously:

D-α-[3-(2-diethylamino-4-hydroxy-5-pyrimidyl)-ureido]-m-chloro-p-hydroxybenzyl-penicillin sodium.

D-α-[3-(2-dimethylamino-4-hydroxy-5-pyrimidyl)-ureido]-m,p-dihydroxybenzyl-penicillin sodium.

D-α-[3-(2-ethyl-methylamino-4-hydroxy-5-pyrimidy)-ureido]-p-hydroxybenzyl-penicillin sodium.

D-α-[3-(2-ethyl-methylamino-4-hydroxy-5-pyrimidyl) ureido]-benzyl-penicillin sodium.

D-α-[3-(2-dibutylamino-4-hydroxy-5-pyrimidyl)-ureido]-p-hydroxybenzyl-penicillin sodium.

EXAMPLE 100

D-α-[3-(2-cyclopropylamino-4-hydroxy-5-pyrimidyl)-ureido]-p-hydroxybenzyl-penicillin sodium This penicillin is prepared analogous to Example 11, starting from 4.2 gm of amoxycillin trihydrate (0.01 mol) as well as the reaction product of 1.66 gm (0.01 mol) of 5-amino-2-cyclopropylamino-4-hydroxy pyrimidine with 1.0 gm of phosgene and 1.37 ml of triethylamine.

Yield: 3.48 gm of sodium salt (60%).

Rf: 0.56.

IR spectrum: 1770, 1665, 1615, 1540 $cm^{-1}$.

NMR spectrum (DMSO+$CD_3OD$) signals at ppm: 0.5 (4H), 1.55 (6H), 3.7 (1H), 4.0 (1H), 5.5 (3H), 6.9 (2H), 7.35 (2H), 8.25 (1H).

EXAMPLE 101

D-α-[3-(2-cyclopropylamino-4-hydroxy-5-pyrimidyl)-ureido]-benzyl-penicillin sodium This penicillin is prepared analogous to Example 11, starting from 3.75 gm of ampicillin sodium as well as the reaction product of 1.66 gm of the amine of the Example 100 (0.01 mol) with 1.0 gm of phosgene and 1.37 ml of triethylamine.

Yield: 2.93 gm of sodium salt (52%).

Rf: 0.59.

IR spectrum: 1765, 1660, 1610, 1525 $cm^{-1}$.

NMR spectrum (DMSO+$CD_3OD$) signals at ppm: 0.6 (4H), 1.55 (6H), 3.75 (1H), 4.05 (1H), 5.35 (2H), 5.45 (1H), 6.85 (2H), 7.35 (2H), 8.20 (1H).

EXAMPLE 102

D-α-[3-(2-cyclobutylamino-4-hydroxy-5-pyrimidyl)-ureido]-p-hydroxybenzyl-penicillin sodium This penicillin is prepared analogous to Example 11, starting from 420 mg of amoxycillin trihydrate (0.001 mol) as well as the reaction product of 180 mg of 5-amino-2-cyclobutylamino-4-hydroxy-pyrimidine (0.001 mol) with 100 mg of phosgene and 0.14 ml of triethylamine. Yield: 290 mg of sodium salt (59%). Rf: 0.59.

EXAMPLE 103

D-α-[3-(2-cyclopentylamino-4-hydroxy-5-pyrimidyl)-ureido]-p-hydroxybenzyl-penicillin sodium This penicillin is prepared analogous to Example 11, starting from 840 mg of amoxycillin trihydrate (0.002 mol) as well as the reaction product of 390 mg (0.002 mol) of 5-amino-2-cyclopentylamino-4-hydroxypyrimidine with 200 mg of phosgene and 0.27 ml of triethylamine.

Yield: 610 mg of sodium salt (50%).

Rf: 0.61.

IR spectrum: 1770, 1660, 1615, 1540 $cm^{-1}$.

NMR spectrum (DMSO+$CD_3OD$) signals at ppm: 1.2–2.2 (m,14H), 3.8 (1H), 4.1 (1H), 5.5 (3H), 6.9 (2H), 7.4 (2H), 8.3 (1H).

EXAMPLE 104

D-α-[3-(2-cyclopentylamino-4-hydroxy-5-pyrimidyl)-ureido]-benzyl-penicillin sodium This penicillin is prepared analogous to Example 11, starting from 750 mg of ampicillin sodium (0.002 mol) as well as the reaction product of 380 mg (0.002 mol) of the amine of Example 103 with 200 mg of phosgene and 0.27 ml of triethylamine.

Yield: 685 mg of sodium salt (56%).

Rf: 0.61.

IR spectrum: 1770, 1660, 1615, 1545 $cm^{-1}$.

NMR spectrum (DMSO+$CD_3OD$) signals at ppm: 1.0–2.3 (m,14H), 3.75 (1H), 4.1 (1H), 5.35 (2H), 5.45 (1H), 7.4 (5H), 8.25 (1H).

EXAMPLE 105

D-α-[3-(2-cyclohexylamino-4-hydroxy-5-pyrimidyl)-ureido]-p-hydroxybenzyl-penicillin sodium This penicillin is prepared analogous to Example 11, starting from 4.2 gm of amoxycillin trihydrate (0.01 mol) as well as the reaction product of 2.1 gm (0.01 mol) of 5-amino-2-cyclohexylamino-4-hydroxy-pyrimidine with 1.0 gm of phosgene and 1.35 ml of triethylamine.

Yield: 4.12 gm of sodium salt (65.5%).

Rf: 0.63

IR spectrum: 1770, 1665, 1620, 1525 $cm^{-1}$.

NMR spectrum (DMSO+$CD_3OD$) signals at ppm: 1.0–2.2 (m,16H), 3.75 (1H), 4.05 (1H), 5.35 (q,2H), 5.45 (1H), 6.85 (2H), 7.35 (2H), 8.30 (1H).

EXAMPLE 106

D-α-[3-(2-cyclohexylamino-4-hydroxy-5-pyrimidyl)-ureido]-benzyl-penicillin sodium This penicillin is prepared analogous to Example 11, starting from 1.85 gm (0.005 mol) of ampicillin trihydrate as well as the reaction product of 1.07 gm (0.005 mol) of the amine of Example 105 with 500 mg of phosgene and 0.67 ml of triethylamine.

Yield: 1.78 gm of sodium (57.5%).

Rf: 0.65.

IR spectrum: 1765, 1650, 1600, 1545, 1510 $cm^{-1}$.

NMR spectrum (DMSO+$CD_3OD$) signals at ppm: 1.1–2.2 (m,16H), 3.7 (1H), 4.05 (1H), 5.35 (2H), 5.45 (1H), 7.4 (5H), 8.25 (1H).

EXAMPLE 107

D-α-[3-(2-cyclohexylamino-4-hydroxy-5-pyrimidyl)-ureido]-cyclohexa-1,4-dien-1-yl-methyl-penicillin sodium This penicillin is prepared analogous to Example 11, starting from 3.75 gm of epicillin sodium (0.01 mol) as well as the reaction product of 2.08 gm (0.01 mol) of 5-amino-2-cyclohexylamino-4-hydroxy-5-pyrimidine with 1.0 gm of phosgene and 1.37 ml of triethylamine.

Yield: 3.15 gm of sodium salt (51%).

Rf: 0.64.

IR spectrum: 1765, 1655, 1610, 1540 $cm^{-1}$.

NMR spectrum (DMSO+$CD_3OD$) signals at ppm: 1.1–2.3 (m,16H), 2.5 (4H), 3.75 (1H), 4.05 (1H), 4.85 (1H), 5.35 (2H), 5.60 (3H), 8.25 (1H).

EXAMPLE 108

D-α-[3-(2-cycloheptylamino-4-hydroxy-5-pyrimidyl)-ureido]-p-hydroxybenzyl-penicillin sodium This penicillin is prepared analogous to Example 11, starting from 2.52 gm (0.006 mol) of amoxycillin trihydrate as well as the reaction product of 1.33 gm of 5-amino-2-cycloheptylamino-4-hydroxy-pyrimidine (0.006 mol) with 600 mg of phosgene and 0.82 ml of triethylamine.

Yield: 2.55 gm of sodium salt (66%).

Rf: 0.69.

IR spectrum: 1770, 1650, 1610, 1545 $cm^{-1}$.

NMR spectrum (DMSO+$CD_3OD$) signals at ppm: 1.0–2.3 (m, 18H), 3.65 (1H), 4.05 (1H), 5.35 (2H), 5.45 (1H), 6.8 (2H), 7.3 (2H), 8.25 (1H).

EXAMPLE 109

D-α-[3-(2-cyclopenten-2'-ylamino-4-hydroxy-5-pyrimidyl)-ureido]-p-hydroxybenzyl-penicillin sodium This penicillin is prepared analogous to Example 11, starting from 4.2 gm (0.01 mol) of amoxycillin trihydrate as well as the reaction product of 1.92 gm (0.01 mol) of 5-amino-2-cyclopenten-2'-ylamino-4-hydroxy-pyrimidine with 1.0 gm of phosgene and 1.37 ml of triethylamine.

Yield: 3.45 gm of sodium salt (57%).

Rf: 0.61.

EXAMPLE 110

D-α-[3-(2-cyclohexen-3'-ylamino-4-hydroxy-5-pyrimidyl)-ureido]-p-hydroxybenzyl-penicillin sodium This penicillin is prepared analogous to Example 11, starting from 4.2 gm of amoxycillin trihydrate (0.01 mol) as well as the reaction product of 2.06 gm (0.01 mol) of 5-amino-2-cyclohexen-3-ylamino-4-hydroxy-pyrimidine with 1.0 gm of phosgene and 1.37 ml of triethylamine.

Yield: 3.95 gm of sodium salt (64%).

Rf: 0.64.

EXAMPLE 111

D-α-[3-(4-hydroxy-2-{4'-methyl-cyclohexylamino}-5-pyrimidyl)-ureido]-p-hydroxybenzyl-penicillin sodium This penicillin is prepared analogous to Example 11, starting from 2.1 gm of amoxycillin trihydrate (0.005 mol) as well as the reaction product of 1.11 gm of 5-amino-4-hydroxy-2-(4'-methyl-cyclohexylamino)-pyrimidine (0.005 mol) with 500 mg of phosgene and 0.67 ml of triethylamine.

Yield: 155 gm of sodium salt (47.5%).

Rf: 0.70.

IR spectrum: 1770, 1660, 1610, 1550 $cm^{-1}$.

NMR spectrum (DMSO+$CD_3OD$) signals at ppm: 1.0–2.3 (m,18H), 3.75 (1H), 4.1 (1H), 5.45 (3H), 6.85 (2H), 7.35 (2H), 8.15 (1H)

EXAMPLE 112

D-α-[3-(2-{N-cyclohexyl-N-methyl}-amino-4-hydroxy-5-pyrimidyl)-ureido]-p-hydroxybenzyl-penicillin sodium This penicillin is prepared analogously to Example 11, starting from 1.68 gm (0.004 mol) of amoxycillin trihydrate as well as the reaction product of 900 mgm (0.004 mol) of 5-amino-2-(N-cyclohexyl-N-methyl)-amino-4-hydroxy-pyrimidine with 400 mgm of phosgene and 0.54 ml of triethylamine.

Yield: 1.54 gm of sodium salt (62%). Rf: 0.76

IR spectrum: 1765, 1660, 1610, 1550 $cm^{-1}$.

NMR spectrum: (DMSO+$CD_3OD$) signals at ppm: 1.0–2.2 (m,16H), 3.1 (3H), 3.7 (1H), 4.05 (1H), 5.35 (q,2H), 5.45 (1H), 6.85 (2H), 7.35 (2H), 8.20 (1H).

EXAMPLE 113

D-α-[3-(2-cyclohexylmethylamino-4-hydroxy-5-pyrimidyl)-ureido]-p-hydroxybenzyl-penicillin sodium This penicillin is prepared analogously to Example 11, starting from 3.36 gm (0.008 mol) of amoxycillin trihydrate as well as the reaction product of 1.78 gm (0.008 mol) of 5-amino-2-cyclohexylmethylamino-4-hydroxy-pyrimidine with 800 mgm of phosgene and 1.1 ml of triethylamine.

Yield: 2.78 gm of sodium salt (55%). Rf: 0.69.

IR spectrum: 1770, 1665, 1620, 1545, 1510 $cm^{-1}$.

NMR spectrum (DMSO+$CD_3OD$) signals at ppm: 1.0–2.3 (m,17H), 3.4 (2H), 4.05 (1H), 5.45 (3H), 6.85 (2H), 7.35 (2H), 8.15 (1H).

EXAMPLE 114

D-α-[3-(2-cyclopropylmethylamine-4-hydroxy-5-pyrimidyl)-ureido]-p-hydroxybenzyl-penicillin sodium This penicillin is prepared analogously to Example 11, starting from 700 mgm of amoxycillin trihydrate (0.00167 mol) as well as the reaction product of 300 mgm (0.0017 mol) of 5-amino-2-cyclopropylmethylamino-4-hydroxy-pyrimidine with 170 mgm of phosgene and 0.23 ml of triethylamine.

Yield: 520 gm of sodium salt (52.5%). Rf: 0.62

IR spectrum: 1765, 1660, 1610, 1520 $cm^{-1}$.

NMR spectrum (DMSO+$CD_3OD$) signals at ppm: 0.4 (4H), 1.3 (1H), 1.55 (6H), 3.3 (2H), 4.1 (1H), 5.45 (3H), 6.85 (2H), 7.35 (2H), 8.15 (1H).

EXAMPLE 115

D-α-[3-(2-cyclopropylmethylamino-4-hydroxy-5-pyrimidyl)-ureido]-benzyl-penicillin sodium This penicillin is prepared analogously to Example 11, starting from 750 mgm (0.002 mol) of ampicillin sodium as well as the reaction product of 360 mgm (0.002 mol) of the pyrimidine of Example 114 with 200 mgm of phosgene and 0.27 ml of triethylamine. Yield: 690 mgm of sodium salt (69%). Rf: 0.60.

IR spectrum: 1770, 1660, 1610, 1545, 1510 cm−1.

NMR spectrum (DMSO+$CD_3OD$) signals at ppm: 0.5 (4H), 1.35 (1H), 1.55 (6H), 3.35 (2H), 4.05 (1H), 5.35 (2H), 5.45 (1H), 7.5 (5H), 8.15 (1H).

The following are synthezised analogously:

D-α-[3-(2-cyclopropylamino-4-hydroxy-5-pyrimidyl)-ureido]-m,p-dihydroxybenzyl-penicillin sodium.

D-α-[3-(2-cyclopropylamino-4-hydroxy-5-pyrimidyl)-ureido]-m-chloro-p-hydroxybenzyl-penicillin sodium.

D-α-[3-(2-cyclobutylamino-4-hydroxy-5-pyrimidyl)-ureido]-benzyl-penicillin sodium.

D-α-[3-(2-cyclopentylamino-4-hydroxy-5-pyrimidyl)-ureido]-cyclohexa-1,4-dien-1-yl-methyl-penicillin sodium.

D-α-[3-(2-cyclopentylamino-4-hydroxy-5-pyrimidyl)-ureido]-2-thienylmethyl-penicillin sodium.

D-α-[3-(2-cyclopentylamino-4-hydroxy-5-pyrimidyl)-ureido]-m,p-dihydroxy-benzyl-penicillin sodium.

D-α-[3-(2-cyclopentylamino-4-hydroxy-5-pyrimidyl)-ureido]-m-chloro-p-hydroxybenzyl-penicillin sodium.

D-α-[3-(2-cyclohexylamino-4-hydroxy-5-pyrimidyl)-ureido]-2-thienylmethyl-penicillin sodium.

D-α-[3-(2-cyclohexylamino-4-hydroxy-5-pyrimidyl)-ureido]-m,p-dihydroxy-benzyl-penicillin sodium.

D-α-[3-(2-cyclohexylamino-4-hydroxy-5-pyrimidyl)-ureido]-m-chloro-p-hydroxybenzyl-penicillin sodium.

D-α-[3-(2-cyclohexen-3'-ylamino-4-hydroxy-5-pyrimidyl)-ureido]-benzyl-penicillin sodium.

D-α-[3-(4-hydroxy-2-{4'-methyl-cyclohexylamino}-5-pyrimidyl)-ureido]-benzyl-penicillin sodium.

D-α-[3-(2-{N-cyclohexyl-N-methyl}-amino-4-hydroxy-5-pyrimidyl)-ureido]-benzyl-penicillin sodium.

D-α-[3-(2-{N-cyclopropyl-N-methyl}-amino-4-hydroxy-5-pyrimidyl)-ureido]-p-hydroxy-benzyl-penicillin sodium.

D-α-[3-(2-cycloheptylamino-4-hydroxy-5-pyrimidyl)-ureido]-benzyl-penicillin sodium.

D-α-[3-(2-cyclohexylmethylamino-4-hydroxy-5-pyrimidyl)-ureido]-benzyl-penicillin sodium.

D-α-[3-(2-{2'-cyclohexylethylamino}-4-hydroxy-5-pyrimidyl)-ureido]-p-hydroxybenzyl-penicillin sodium D-α-[3-(2-{N-cyclopropyl-N-methyl}-amino-4-hydroxy-5-pyrimidyl)-ureido]-benzyl-penicillin sodium.

EXAMPLE 116

D-α-[3-(4-hydroxy-2-pyrrolidino-5-pyrimidyl)-ureido]-p-hydroxybenzyl-penicillin sodium This penicillin is synthezised analogously to Example 11, starting from 4.2 gm of amoxycillin trihydrate (0.01 mol) as well as the reaction product of 1.8 gm of 5-amino-4-hydroxy-2-pyrrolidino-pyrimidine. Treatment is effected as follows: the aqueous phase is shaken once at pH 7.0 with ethyl acetate and subsequently mixed with cooling up to pH 2.5 with dilute hydrochloric acid. The precipitated product is extracted quickly and washed with a little water. To prepare the sodium salt, the product is suspended in a little water, mixed with N/10 sodium hydroxide solution dropwise up to pH 6.8 with cooling and freeze-dried.

Yield: 3.33 gm of sodium salt (55%).

Rf: 0.62.

IR spectrum: 1770, 1665, 1620, 1550 $cm^{-1}$.

NMR spectrum (DMSO+$CD_3OD$) signals at ppm: 1.5 (10H), 3.55 (4H), 4.0 (1H), 5.4 (q,2H), 5.5 (1H), 6.8 (2H), 7.35 (2H), 8.1 (1H).

EXAMPLE 117

D-α-[3-(4-hydroxy-2-pyrrolidino-5-pyrimidyl)-ureido]-benzyl-penicillin sodium

This penicillin is prepared analogously to Example 116, starting from 750 mgm (0.002 mol) of ampicillin sodium as well as the reaction product of 360 mgm of 5-amino-4-hydroxy-2-pyrrolidino-pyrimidine (0.002 mol) with 200 mgm of phosgene and 0.27 ml of triethylamine.

Yield: 710 mgm of sodium salt (61%).

Rf: 0.63.

IR spectrum: 1770, 1665, 1620, 1550 $cm^{-1}$.

NMR spectrum (DMSO+$CD_3OD$) signals at ppm: 1.55 (10H), 3.5 (4H), 4.05 (1H), 5.45 (3H), 7.5 (5H), 8.15 (1H).

EXAMPLE 118

D-α-[3-(4-hydroxy-2-piperidino-5-pyrimidyl)-ureido]-p-hydroxybenzyl-penicillin sodium This penicillin is prepared analogously to Example 11, starting from 840 mgm of amoxycillin trihydrate (0.002 mol) as well as the reaction product of 385 mgm of 5-amino-4-hydroxy-2-piperidino-pyrimidine with 200 mgm of phosgene and 0.27 ml of triethylamine.

Yield: 770 gm of sodium salt (63%).

Rf: 0.67.

IR spectrum: 1770, 1670, 1620, 1550 $cm^{-1}$.

NMR spectrum (DMSO+$CD_3OD$) signals at ppm: 1.55 (12H), 3.55 (4H), 4.05 (1H), 5.4 (3H), 6.8 (2H), 7.35 (2H), 8.1 (1H).

The following are prepared analogously:

D-α-[3-(2-{4'-benzyl-piperidino}-4-hydroxy-5-pyrimidyl)-ureido]-p-hydroxybenzyl-penicillin sodium.

D-α-[3-(4-hydroxy-2-indolino-5-pyrimidyl)-ureido]-p-hydroxy-benzyl-penicillin sodium.

EXAMPLE 119

D-α-[3-(2-hexahydroazepino-4-hydroxy-5-pyrimidyl)-ureidol]-p-hydroxybenzyl-penicillin sodium This penicillin is prepared analogously to Example 11, starting from 2.3 gm of amoxycillin trihydrate (0.0055 mol) as well as the reaction product of 1.14 gm (0.0055 mol) of 5-amino-2-hexahydroazepino-4-hydroxy-pyrimidine with 555 mgm of phosgene and 0.73 ml of triethylamine.

Yield: 2.44 gm of sodium salt (71%).

Rf: 0.70.

IR spectrum: 1770, 1670, 1620, 1550 $cm^{-1}$.

NMR spectrum (DMSO+$CD_3OD$) signals at ppm: 1.5 (14H), 3.5 (4H), 4.1 (1H), 5.35 (q,2H), 5.45 (1H), 6.85 (2H), 7.35 (2H), 8.15 (1H).

EXAMPLE 120

D-α-[3-(2-N-formylpiperazino-4-hydroxy-5-pyrimidyl)-ureido]-p-hydroxybenzyl-penicillin sodium This penicillin is prepared analogously to Example 2, starting from 840 mgm of amoxycillin trihydrate (0.002 mol) as well as 450 mgm of 5-amino-2-N-formyl-piperazino-4-hydroxy-pyrimidine (0.002 mol) which has been reacted after silylation with 200 mgm of phosgene and 0.27 ml of triethylamine.

Yield: 420 mgm of sodium salt (33%).

Rf: 0.58.

IR spectrum: 1770, 1670, 1630, 1620, 1550 $cm^{-1}$.

NMR spectrum (DMSO+$CD_3OD$) signals at ppm: 1.55 (6H), 3.7 (8H), 4.05 (1H), 5.45 (3H), 6.8 (2H), 7.3 (2H), 8.20 (1H), 8.25 (1H).

EXAMPLE 121

D-α-[3-(2-N-formylpiperazino-4-hydroxy-5-pyrimidyl)-ureido]-benzyl-penicillin sodium This penicillin is prepared analogously to Example 120, starting from 500 mgm of ampicillin sodium (0.00134 mol) as well as 300 mgm of amine of Example 120 which has been reacted after silylation with hexamethyl disiliazane with 140 mgm of phosgene and 0.18 ml of triethylamine.

Yield: 240 mgm of sodium salt (29%).

Rf: 0.54.

IR spectrum: 1770, 1660, 1610, 1550 $cm^{-1}$.

NMR spectrum: (DMSO+$CD_3OD$) signals at ppm: 1.55 (6H), 3.7 (8H), 4.05 (1H), 5.35 (2H), 5.45 (1H), 6.85 (2H), 7.35 (2H), 8.20 (1H), 8.30 (1H).

EXAMPLE 122

D-α-[3-(2-N-acetylpiperazino-4-hydroxy-5-pyrimidyl)-ureido]-p-hydroxybenzyl-penicillin sodium This penicillin is prepared analogously to Example 2, starting from 1.0 gm of amoxycillin trihydrate (0.00238 mol) as well as 570 mgm of 2-N-acetylpiperazino-5-amino-4-hydroxy-pyrimidine (0.0024 mol) which has been reacted after silylation with 240 mgm of phosgene and 0.33 ml of triethylamine.

Yield: 530 gm of sodium salt (34%).

Rf: 0.59.

IR spectrum: 1770, 1675, 1620, 1550 $cm^{-1}$.

NMR spectrum (DMSO+$CD_3OD$) signals at ppm: 1.55 (6H), 2.2 (3H), 3.7 (8H), 4.1 (1H), 5.35 (2H), 5.45 (1H), 6.8 (2H), 7.35 (2H), 8.25 (1H).

EXAMPLE 123

D-α-[3-(2-N-ethoxycarbonyl-piperazino-4-hydroxy-5-pyrimidyl)-ureido]-p-hydroxybenzyl-penicillin sodium This penicillin is prepared analogously to Example 11, starting from 2.1 gm (0.005 mol) of amoxycillin trihydrate as well as the reaction product of 1.34 gm (0.005 mol) of 5-amino-2-N-ethoxycarbonyl-piperazino-4-hydroxy-pyrimidine with 500 mgm of phosgene and 0.67 ml of triethylamine.

Yield: 1.8 gm of sodium salt (53%).

Rf: 0.64.

IR spectrum: 1770, 1680, 1650, 1600, 1550 $cm^{-1}$.

NMR spectrum (DMSO+$CD_3OD$) signals at ppm: 1.4 (3H), 1.55 (6H), 3.7 (8H), 4.05 (1H), 4.1 (2H), 5.35 (2H), 5.5 (1H), 6.85 (2H), 7.35 (2H), 8.2 (1H).

EXAMPLE 124

D-α-[3-(2-N-acetylpiperazino-4-hydroxy-5-pyrimidyl)-ureido]-benzyl-penicillin sodium This penicillin is prepared analogously to Example 11, starting from 3.70 gm (0.01 mol) of ampicillin sodium as well as the reaction product of 2.37 gm of 2-N-acetyl-piperazino-5-amino-4-hydroxy-pyrimidine (0.01 mol) with 1.0 gm of phosgene and 1.35 ml of triethylamine.

Yield: 2.04 gm of sodium salt (32%).

Rf: 0.61.

IR spectrum: 1770, 1670, 1660, 1600, 1550 $cm^{-1}$.

NMR spectrum (DMSO+$CD_3OD$) signals at ppm: 1.55 (6H), 2.25 (3H), 3.65 (8H), 4.05 (1H), 5.35 (2H), 5.45 (1H), 7.45 (5H), 8.20 (1H).

EXAMPLE 125

D-α-[3-(2-N-benzyloxycarbonylpiperazino-4-hydroxy-5-pyrimidyl)-ureido]-p-hydroxybenzyl-penicillin sodium This penicillin is prepared analogously to Example 11, starting from 2.1 gm (0.005 mol) of amoxycillin as well as the reaction product of 1.65 gm of 5-amino-2-N-benzyloxycarbonyl-piperazino-4-hydroxy-pyrimidine (0.005 mol) with 500 mgm of phosgene and 0.67 ml of triethylamine.

Yield: 2.14 gm of sodium salt (58%).

Rf: 0.71.

IR spectrum: 1770, 1690, 1660, 1550 $cm^{-1}$.

NMR spectrum (DMSO+$CD_3OD$) signals at ppm: 1.55 (6H), 3.7 (8H), 4.05 (1H), 5.2 (2H), 5.45 (3H), 6.8 (2H), 7.4 (7H), 8.3 (1H).

EXAMPLE 126

D-α-[3-(2-benzyloxy-carbonylpiperazino-4-hydroxy-5-pyrimidyl)-ureido]-benzyl-penicillin sodium This penicillin is prepared analogously to Example 11, starting from 1.85 gm (0.005 mol) of ampicillin sodium as well as the reaction product of 1.65 gm of 5-amino-2-N-benzyloxycarbonyl-piperazino-4-hydroxy-pyrimidine (0.005 mol) with 500 mgm of phosgene and 0.67 ml of triethylamine.

Yield: 2.02 gm of sodium salt (54%).

Rf: 0.73.

IR spectrum: 1770, 1700, 1660, 1600, 1550 $cm^{-1}$.

NMR spectrum (DMSO+$CD_3OD$) signals at ppm: 1.55 (6H), 3.75 (8H), 4.0 (1H), 5.25 (2H), 5.4 (2H), 5.5 (1H), 7.45 (10H), 8.25 (1H).

EXAMPLE 127

D-α-[3-(4-hydroxy-2-N-phenylpiperazino-4-pyrimidyl)-ureido]-p-hydroxybenzyl-penicillin This penicillin is prepared analogously to Example 11, starting from 1.0 gm of amoxycillin trihydrate (0.00237 mol) as well as the reaction product of 625 mgm (0.0024 mol) of 5-amino-4-hydroxy-2-N-phenyl-piperazino-pyrimidine with 240 mgm of phosgene and 0.32 ml of triethylamine.

Yield: 750 mgm of sodium salt (45.5%).

Rf: 0.76.

IR spectrum: 1770, 1660, 1600, 1550 $cm^{-1}$.

NMR spectrum (DMSO+$CD_3OD$) signals at ppm: 1.50 (6H), 3.6 (8H), 4.1 (1H), 5.35 (2H), 5.45 (1H), 6.85 (2H), 7.35 (7H), 8.15 (1H).

EXAMPLE 128

D-α-[3-(4-hydroxy-2-N-methylpiperazino-4-pyrimidyl)-ureido]-p-hydroxybenzyl-penicillin sodium This penicillin is prepared analogously to Example 11, starting from 1.5 gm of amoxycillin trihydrate (0.0036 mol) as well as the reaction product of 750 mgm (0.0036 mol) of 5-amino-4-hydroxy-2-N-methyl-piperazino-pyrimidine with 360 mgm of phosgene and 0.5 ml of triethylamine.

Yield: 1.18 gm of sodium salt (53%).

Rf: 0.66.

IR spectrum: 1770, 1650, 1600, 1545 $cm^{-1}$.

NMR spectrum (DMSO+$CD_3OD$) signals at ppm: 1.55 (6H), 3.15 (3H), 3.4 (8H), 4.05 (1H), 5.45 (3H), 6.85 (2H), 7.35 (2H), 8.20 (1H).

EXAMPLE 129

D-α-[3-(4-hydroxy-2-morpholiono-5-pyrimidyl)-ureido]-p-hydroxybenzyl-penicillin sodium This penicillin is prepared analogously to Example 11, starting from 4.2 gm of amoxycillin trihydrate (0.01 mol) as well as the reaction product of 1.96 gm (0.01 mol) of 5-amino-4-hydroxy-2-morpholino-pyrimidine with 1.0 gm of phosgene and 1.37 ml of triethylamine.

Yield: 3.72 gm of sodium salt (61%).

NMR spectrum: (DMSO+$CD_3OD$) signals at ppm: 1.50 (6H),3.5 (4H), 3.7 (4H), 4.0 (1H), 5.4 (q,2H), 5.5 (1H), 6.8 (2H), 7.3 (2H), 8.2 (1H).

EXAMPLE 130

D-α-[3-(4-hydroxy-2-morpholino-5-pyrimidyl)-ureido]-benzyl-penicillin sodium

This penicillin is prepared analogously to Example 11, starting from 2.0 gm (0.0054 mol) of ampicillin sodium as well as the reaction product of 1.06 gm (0.0054 mol) of 5-amino-4-hydroxy-2-morpholino-pyrimidine with 550 mgm of phosgene and 0.75 ml of triethylamine.

Yield: 1.62 gm of sodium salt (49%).

IR spectrum: 1770, 1655, 1605, 1530 $cm^{-1}$.

NMR spectrum (DMSO+$CD_3OD$) signals at ppm: 1.55 (6H), 3.45 (4H), 3.70 (4H), 4.05 (1H), 5.35 (q,2H), 5.45 (1H), 7.45 (5H), 8.15 (1H).

EXAMPLE 131

D-α-[3-(4-hydroxy-2-thiomorpholino-5-pyrimidyl)-ureido]-p-hydroxybenzyl-penicillin sodium This penicillin is prepared analogously to Example 11, starting from 420 mgm of amoxycillin trihydrate (0.001 mol) as well as the reaction product of 210 mgm (0.001 mol) of 5-amino-4-hydroxy-2-thiomorpholino-pyrimidine with 100 mgm of phosgene and 0.14 ml of triethylamine.

Yield: 355 mgm of sodium salt (55.5%).

Rf: 0.74.

IR spectrum: 1770, 1650, 1600, 1530 $cm^{-1}$.

NMR spectrum (DMSO+$CD_3OD$) signals at ppm: 1.5 (6H), 3.9 (8H), 4.05 (1H), 5.45 (3H), 6.75 (2H), 7.3 (2H), 8.2 (1H).

EXAMPLE 132

D-α-[3-(4-hydroxy-2-thiomorpholino-S-oxide-5-pyrimidyl)-ureido]-p-hydroxybenzyl-penicillin sodium This penicillin is prepared analogously to Example 75, starting from 800 mgm of amoxycillin trihydrate (0.0019 mol) as well as 440 mgm (0.0019 mol) of 5-amino-4-hydroxy-2-thiomorpholino-S-oxide-pyrimidine which has first been silylated with hexamethyl disilazane and reacted with 200 mgm of phosgene and 0.26 ml of triethylamine.

Yield: 340 mgm of sodium salt (29%).

Rf: 0.59.

IR spectrum: 1770, 1660, 1600, 1540 $cm^{-1}$.

NMR spectrum (DMSO+$CD_3OD$) signals at ppm: 1.5 (6H), 3.5–4.0 (m,8H), 4.05 (1H), 5.4 (q,2H), 5.5 (1H), 6.8 (2H), 7.3 (2H), 8.15 (1H).

EXAMPLE 133

D-α-[3-(4-hydroxy-2-thiomorpholino-S,S-dioxide-5-pyrimidyl)-ureido]-p-hydroxybenzyl-penicillin sodium This penicillin is prepared analogously to Example 75, starting from 2.1 gm of amoxycillin trihydrate (0.005 mol) as well as 1.22 gm (0.005 mol) of 5-amino-4-hydroxy-2-thiomorpholino-S,S-dioxide-pyrimidine which has been treated with hexamethyl disilazane and then reacted with 500 mgm of phosgene and 0.65 ml of triethylamine.

Yield: 1.29 gm of sodium salt (39%).

Rf: 0.55.

IR spectrum: 1770, 1650, 1600, 1550 $cm^{-1}$.

NMR spectrum (DMSO+$CD_3OD$) signals at ppm: 1.5 (6H), 3.6–4.0 (m,8H), 4.0 (1H), 5.5 (3H), 6.8 (2H), 7.35 (2H), 8.15 (1H).

The following are synthezised analogously:

D-α-[3-(4-hydroxy-2-piperidino-5-pyrimidyl)-ureido]-benzyl-penicillin sodium.

D-α-[3-(4-hydroxy-2N-phenylpiperazino-5-pyrimidyl)-ureido]-benzyl-penicillin sodium.

D-α-[3-(4-hydroxy-2-N-methylpiperazino-5-pyrimidyl)-ureido]-benzyl-penicillin sodium.

D-α-[3-(4-hydroxy-2-piperazino-5-pyrimidyl)-ureido]-benzyl-penicillin sodium.

D-α-[3-(4-hydroxy-2-piperazino-5-pyrimidyl)-ureido]-p-hydroxybenzyl-penicillin sodium.

D-α-[3-(4-hydroxy-2-thiomorpholino-S-oxide-5-pyrimidyl)-ureido]-benzyl-penicillin sodium.

D-α-[3-(4-hydroxy-2-thiomorpholino-S,S-dioxide-5-pyrimidyl)-ureido]-benzyl-penicillin sodium.

EXAMPLE 134

D-α-[3-(2-anilino-4-hydroxy-5-pyrimidyl)-ureido]-p-hydroxy-benzyl-penicillin sodium 600 mgm (0.003 mol) of 5-amino-2-anilino-4-hydroxy-pyrimidine are dissolved in heat in absolute tetrahydrofurane together with 300 mgm of triethylamine. This mixture is dropped with ice-cooling into a solution of 3.05 mgm of phosgene in 50 ml of absolute tetrahydrofurane. After the addition, the mixture is stirred for half an hour and subsequently evaporated in vacuo to approximately 50 ml. The mixture is dropped with ice-bath cooling into a solution prepared in the cold with triethylamine of 1.26 gm of amoxycillin trihydrate (0.003 mol) in 60 ml of 80% aqueous tetrahydrofurane. In so doing, the pH value is kept at approximately 7.5 with triethylamine. After addition, stirring is continued for 1 hour at 5° C. and 1 hour at room temperature. Tetrahydrofurane is then extracted in vacuo and the mixture is filled up with water to approximately 50 ml and extracted twice with ethyl acetate at pH 7.0. It is subsequently cooled with ice, covered with a layer of 200 ml of ethyl acetate and brought with dilute hydrochloric acid to pH 2.0 with vigorous stirring. The organic phase is separated, the aqueous phase is extracted once again with 50 ml of ethyl acetate, the organic phases are united and dried with sodium sulphate and the solvent is removed in vacuo. The remaining solid product is dissolved in a little ethanol and mixed with sodium hexanoate and the sodium salt is precipitated by the addition of absolute ether.

Yield: 1.46 gm (79%).

IR spectrum: 1775, 1660, 1610, 1540 $cm^{-1}$.

NMR spectrum (DMSO+$CD_3OD$) signals at ppm: 1.55 (6H), 4.1 (1H), 5.5 (3H), 6.8 (d,2H), 7.35 (m,7H), 8.35 (1H).

EXAMPLE 135

D-α-[3-(2-anilino-4-hydroxy-5-pyrimidyl)-ureido]-benzyl-penicillin sodium

Analogously to Example 134, starting from 2.0 gm (0.005 mol) of amipicillin trihydrate and the raction product of 1.0 gm (0.005 mol) of 5-amino-2-anilino-4-hydroxy-pyrimidine with 500 mgm of phosgene.

Yield: 2.25 gm (75%) of sodium salt.

IR spectrum: 1776, 1660, 1610, 1540 $cm^{-1}$.

NMR spectrum: 1.55 (6H), 4.05 (1H), 5.4 (q,2H), 5.6 (1H), 7.3 (m,10H), 8.40 (1H).

EXAMPLE 136

D-α-[3-(2-anilino-4-hydroxy-5-pyrimidyl)-ureido]-1,4-cyclohexa-dien-1-yl-methyl-penicillin sodium Analogously to Example 134, starting from 3.73 gm of epicillin sodium (0.01 mol) and the reaction product of 2.0 gm (0.01 mol) of 5-amino-2-anilino-4-hydroxy-pyrimidine with 1.0 gm of phosgene.

Yield: 4.56 gm of sodium salt (76%).

IR spectrum: 1.50 (6H), 2.50 (4H), 4.05 (1H), 4.90 (1H), 5.30 (2H), 5.65 (3H), 7.45 (5H), 8.35 (1H).

The following are synthezised analogously:

D-α-[3-(2-anilino-4-hydroxy-5-pyrimidyl)-ureido]-2-thienyl-methyl-penicillin sodium.

D-α-[3-(2-anilino-4-hydroxy-5-pyrimidyl)-ureido]-m,p-dihydroxybenzyl-penicillin sodium.

D-α-[3-(2-anilino-4-hydroxy-5-pyrimidyl)-ureido]-m-chloro-p-hydroxybenzyl-penicillin sodium.

EXAMPLE 137

D-α-[3-(2-p-chloroanilino-4-hydroxy-5-pyrimidyl)-ureido]-p-hydroxybenzyl-penicillin sodium Analogously to Example 134, starting from 1.68 gm (0.004 mol) of amoxycillin trihydrate and the reaction product of 940 mgm (0.004 mol) of 5-amino-2-p-chloro-anilino-4-hydroxypyrimidine with 410 mgm of phosgene and 400 mgm of triethylamine.

Yield: 2.1 gm (81%).

IR spectrum: 1770, 1660, 1610, 1540, 1515 $cm^{-1}$.

NMR spectrum: (DMSO+$CD_3OD$) signals at ppm: 1.55 (6H), 4.1 (1H), 5.5 (q,2H), 5.6 (1H), 6.85 (d,2H), 7.4 (m,4H), 7.9 (d,2H), 8.45 (1H).

EXAMPLE 138

D-α-[3-(2-p-chloroanilino-4-hydroxy-5-pyrimidyl)-ureido]-cyclohexa-1,4-dien-1-yl-methyl-penicillin sodium Analogously to Example 134, starting from 1.87 gm of epicillin sodium (0.005 mol) and 1.18 gm of the pyrimidine of Example 137 (0.005 mol) as well as 510 mgm of phosgene and 500 mgm of triethylamine. Yield: 2.29 gm (74%) of sodium salt.

IR spectrum: 1765, 1655, 1610, 1540, 1505 $cm^{-1}$.

NMR spectrum (DMSO+$CD_3OD$) signals at ppm: 1.55 (6H), 2.55 (4H), 4.05 (1H), 4.95 (1H), 5.35 (2H), 5.70 (3H), 7.35 (d,2H), 7.85 (d,2H), 8.40 (1H).

EXAMPLE 139

D-α-[3-(2-p-chloroanilino-4-hydroxy-5-pyrimidyl)-ureido]-benzyl-penicillin-sodium This penicillin is prepared analogously to Example 134, starting from 3.75 gm of ampicillin-sodium (0.01 mol) as well as the reaction product of 2.36 gm of the pyrimidine of Example 138 (0.01 mol) with 1.0 gm of phosgene and 1.35 ml of triethylamine.

Yield: 4.5 gm of sodium salt (69%).

IR spectrum: 1770, 1650, 1610, 1540 $cm^{-1}$.

NMR spectrum (DMSO+$CD_3OD$) signals at ppm: 1.55 (6H), 4.05 (1H), 5.5 (3H), 7.5 (7H), 7.9 (2H), 8.4 (1H).

EXAMPLE 140

D-α-[3-(2-p-fluoroanilino-4-hydroxy-5-pyrimidyl)-ureido]-p-hydroxybenzyl-penicillin sodium 2.19 gm (0.01 mol) of 5-amino-2-p-fluoroanilino-4-hydroxy-pyrimidine are reacted with 1.05 gm of phosgene and 1.0 gm of triethylamine, are as specified in Example 134. 4.2 gm (0.01 mol) of amoxycillin are dissolved carefully with ice-cooling in 80 ml of 8% aqueous tetrahydrofurane with 10 ml of 1 N sodium hydroxide solution. The solution prepared above is dropped with ice-cooling into the amoxycillin sodium salt obtained. The pH value is kept at 7 by the dropwise addition of N/10 sodium hydroxide solution. Treatment is effected analogously to Example 134.

Yield: 5.45 gm of sodium salt (86%).

IR spectrum: 1770, 1660, 1610, 1545, 1510 $cm^{-1}$.

NMR spectrum (DMSO+$CD_3OD$): signals at ppm: 1.55 (6H), 4.05 (1H), 5.50 (q,2H), 5.55 (1H), 6.85 (d,2H), 7.4 (m,4H), 7.85 (d,2H), 8.40 (1H).

EXAMPLE 141

D-α-[3-(2-p-fluoroanilino-4-hydroxy-5-pyrimidyl)-ureido]-benzyl-penicillin-sodium Analogously to Example 134, starting from 3.71 gm (0.01 mol) of ampicillin-sodium and the reaction product of 2.20 gm (0.01 mol) of 5-amino-2-p-fluoroanilino-4-hydroxypyrimidine with 1.05 gm of phosgene and 1.35 ml of triethylamine.

Yield: 5.24 gm (85%) of sodium salt.

IR spectrum: 1765, 1660, 1610, 1550, 1510 $cm^{-1}$.

NMR spectrum (DMSO+$CD_3OD$) signals at ppm: 1.55 (6H), 4.05 (1H), 5.45 (q,2H), 5.50 (1H), 6.90 (d,2H), 7.55 (m,7H), 8.35 (1H).

The following are synthezised analogously:

D-α-[3-(2-p-chloroanilino-4-hydroxy-5-pyrimidyl)-ureido]-2-thienylmethyl-penicillin sodium. D-α-[3-(2-p-chloroanilino-4-hydroxy-5-pyrimidyl)-ureido]-m,p-dihydroxy-benzyl-penicillin sodium.

D-α-[3-(2-p-chloroanilino-4-hydroxy-5-pyrimidyl)-ureido]-m-chloro-p-hydroxy-benzyl-penicillin sodium.

D-α-[3-(2-p-fluoroanilino-4-hydroxy-5-pyrimidyl)-ureido]-2-thienylmethyl-penicillin sodium.

D-α-[3-(2-fluoroanilino-4-hydroxy-5-pyrimidyl)-ureido]-m-chloro-p-hydroxy-benzyl-penicillin sodium.

EXAMPLE 142

D-α-[3-(2-m,p-dichloroanilino-4-hydroxy-5-pyrimidyl)-ureido]-p-hydroxybenzyl-penicillin sodium This penicillin is prepared analogously to Example 134, starting from 405 mgm of 5-amino-2-m,p-dichloroanilino-4-hydroxy-pyrimidine (0.0015 mol), 155 mgm of phosgene and 0.2 ml of triethylamine and reacting with 630 mgm of amoxycillin-trihydrate.

Yield: 710 mgm of sodium salt (69%).

IR spectrum: 1770, 1655, 1610, 1545, 1510 $cm^{-1}$.

NMR spectrum (DMSO+$CD_3OD$) signals at ppm: 1.55 (6H), 4.05 (1H), 5.50 (q,2H), 5.55 (1H), 6.85 (d,2H), 7.5 (m,5H), 8.5 (1H).

EXAMPLE 143

D-α-[3-(2-o-chloroanilino-4-hydroxy-5-pyrimidyl)-ureido]-p-hydroxybenzyl-penicillin-sodium Analogously to Example 134, starting from 710 mgm of 5-amino-2-o-chloroanilino-4-hydroxy-pyrimidine (0.003 mol), 310 mgm of phosgene, 300 mgm of triethylamine and 1.26 gm of amoxycillin-trihydrate (0.003 mol).

Yield: 1.79 gm of sodium salt (91%).

IR spectrum: 1770, 1660, 1610, 1540, 1515 $cm^{-1}$.

NMR spectrum (DMSO+$CD_3OD$) signals at ppm: 1.55 (6H), 4.10 (1H), 5.45 (q,2H), 5.55 (1H), 6.85 (d,2H), 7.4 (m,6H), 8.35 (1H).

EXAMPLE 144

D-α-[3-(2-o-chloroanilino-4-hydroxy-5-pyrimidyl)-ureido]-benzyl-penicillin-sodium Analogously to Example 143, but, instead of amoxycillin, 4.03 gm (0.01 mol) of ampicillin-trihydrate are reacted with 2.36 gm (0.01 mol) of the pyrimidine mentioned therein.

Yield: 5.35 gm of sodium salt (82%).

IR spectrum: 1770, 1655, 1610, 1535, 1510 $cm^{-1}$.

NMR spectrum (DMSO+$CD_3OD$) signals at ppm: 1.55 (6H), 4.05 (1H), 5.45 (q,2H), 5.55 (1H), 7.45 (m,9H), 8.35 (1H).

EXAMPLE 145

D-α-[3-(2-m-chloroanilino-4-hydroxy-5-pyrimidyl)-ureido]-p-hydroxybenzyl-penicillin-sodium This penicillin is obtained if 8.40 gm of amoxycillin-trihydrate (0.02 mol) and the reaction product of 4.75 gm of 5-amino-2-m-chloroanilino-4-hydroxy-pyrimidine (0.02 mol) with 2.05 gm of phosgene are allowed to react together in the way described in Example 134.

Yield: 9.8 gm of sodium salt (75%).

IR spectrum: 1770, 1660, 1615, 1545, 1515 $cm^{-1}$.

NMR spectrum: (DMSO+$CD_3OD$) signals at ppm: 1.55 (6H), 4.0 (1H), 5.45 (q,2H), 5.55 (1H), 6.85 (d,2H), 7.50 (m,6H), 8.40 (1H).

EXAMPLE 146

D-α-[3-(2-m-chloroanilino-4-hydroxy-5-pyrimidyl)-ureido]-benzyl-penicillin-sodium Analogously to Example 134, starting from 2.82 gm of ampicillin-trihydrate (0.007 mol), 1.65 gm (0.007 mol) of 5-amino-2-m-chloroanilino-4-hydroxy-pyrimidine and 700 mgm of phosgene.

Yield: 3.19 gm of sodium salt (72%).

IR spectrum: 1765, 1655, 1610, 1540, 1510 $cm^{-1}$.

NMR spectrum (DMSO+$CD_3OD$) signals at ppm: 1.55 (6H), 4.05 (1H), 5.50 (q,2H), 5.55 (1H), 7.50 (m,9H), 8.35 (1H).

EXAMPLE 147

D-α-[3-(4-hydroxy-2-p-trifluoromethylanilino-5-pyrimidyl)-ureido]-p-hydroxybenzyl-penicillin-sodium 2.70 gm (0.01 mol) of 5-amino-4-hydroxy-2-p-trifluoromethylanilino-pyridine are allowed to react with 1.05 gm of phosgene and 1.35 ml of triethylamine. 4.20 gm (0.01 mol) of amoxycillin are then reacted therewith analogously to Example 134.

Yield: 6.0 gm of sodium salt (88%).

IR spectrum: 1770, 1660, 1550, 1515 $cm^{-1}$.

NMR spectrum (DMSO+$CD_3OD$) signals at ppm: 1.55 (6H), 4.05 (1H), 5.45 (q,2H), 5.50 (1H), 6.85 (d,2H), 7.35 (m,2H), 7.55 (d,2H), 8.40 (1H).

EXAMPLE 148

D-α-[3-(4-hydroxy-2-p-trifluoromethylanilino-5-pyrimidyl)-ureido]-benzyl-penicillin-sodium Analogously to Example 134, starting from 3.71 gm of ampicillin-sodium (0.01 mol) and the reaction product of 2.70 gm of pyrimidine of Example 147 (0.01 mol) with 1.05 gm of phosgene.

Yield: 4.77 gm of sodium salt (71%).

IR spectrum: 1765, 1655, 1610, 1550, 1515 $cm^{-1}$.

NMR spectrum (DMSO+$CD_3OD$) signals at ppm: 1.55 (6H), 4.10 (1H), 5.50 (q,2H), 5.55 (1H), 7.55 (m,9H), 8.35 (1H).

EXAMPLE 149

D-α-[3-(4-hydroxy-2-p-methoxyanilino-5-pyrimidyl)-ureido]-p-hydroxybenzyl-penicillin-sodium This penicillin is synthezised analogously to Example 134, whereby 1.16 gm of 5-amino-4-hydroxy-2-p-methoxyanilino-pyrimidine (0.005 mol) are firstly reacted with 500 mgm of phosgene and 0.67 ml of triethylamine. The product obtained is then reacted analogously to Example 134 with 2.1 gm of amoxycillin-trihydrate (0.005 mol). Treatment is effected so that the penicillinic acid obtained precipitates from water at pH 2.0 and is extracted, washed with ether and dried. It is subsequently converted into the sodium salt in the conventional way.

Yield: 2.73 gm (83%).

IR spectrum: 1770, 1660, 1610, 1550, 1510 $cm^{-1}$.

NMR spectrum (DMSO+$CD_3OD$) signals at ppm: 1.55 (6H), 3.8 (3H), 4.1 (1H), 5.45 (q,2H), 5.55 (1H), 6.9 (m,4H), 7.4 (d,2H), 7.6 (d,2H), 8.3 (1H).

EXAMPLE 150

D-α-[3-(4-hydroxy-2-p-methoxyanilino-5-pyrimidyl)-ureido]-benzyl-penicillin-sodium This penicillin is prepared analogously to Example 149, starting from 2.0 gm of ampicillin-trihydrate (0.005 mol) as well as the reaction product of 1.16 gm of the pyrimidine of Example 149 (0.005 mol) with 0.5 gm of phosgene and 0.68 ml of triethylamine.

Yield: 2.37 gm of sodium salt (77%).

IR spectrum: 1770, 1660, 1605, 1540 $cm^{-1}$.

NMR spectrum (DMSO+$CD_3OD$) signals at ppm: 1.50 (6H), 3.75 (3H), 4.05 (1H), 5.40 (q,2H), 5.5 (1H), 7.0 (2H), 7.5 (7H), 8.25 (1H).

EXAMPLE 151

D-α-[3-(2-p-acetylaminoanilino-4-hydroxy-5-pyrimidyl)ureido]-p-hydroxybenzyl-penicillin-sodium Preparation starts from 780 mgm (0.003 mol) of 2-p-acetylamino-5-amino-4-hydroxy-pyrimidine, 300 gm of phosgene and 0.41 ml of triethylamine in absolute tetrahydrofurane. The product obtained is reacted with 1.26 gm (0.003 mol) of amoxycillin-trihydrate analogously to Example 134. After reaction is effected, tetrahydrofurane is removed in vacuo and the aqueous phase is diluted to 50 ml and extracted twice at pH 7.0 with ethylacetate. The aqueous phase is then brought with dilute hydrochloric acid to pH 2.0 with ice-cooling. The precipitated product is extracted, washed with ether and dried. The sodium salt is prepared in a conventional way.

Yield: 1.08 gm of sodium salt (54%).

IR spectrum: 1770, 1655, 1610, 1545, 1510 $cm^{-1}$.

NMR spectrum (DMSO+$CD_3OD$) signals at ppm: 1.55 (6H), 2.05 (3H), 4.0 (1H), 5.4 (q,2H), 5.5 (1H), 6.8 (d,2H), 7.3 (m,4H), 7.6 (2H), 8.3 (1H).

EXAMPLE 152

D-α-[3-(2-p-acetylaminoanilino-4-hydroxy-5-pyrimidyl)-ureido]-benzyl-penicillin-sodium This penicillin is prepared analogously to Example 151, starting from 1.2 gm of ampicillin-trihydrate (0.003 mol) as well as the reaction product of 780 mgm (0.003 mol) of the pyrimidine of Example 151 with 300 mgm of phosgene and 0.41 ml of triethylamine.

Yield: 950 mgm of sodium salt (51%).

IR spectrum: 1765, 1650, 1605, 1540, 1510 $cm^{-1}$.

NMR spectrum (DMSO+$CD_3OD$) signals at ppm: 1.5 (6H), 2.05 (3H), 4.05 (1H), 5.45 (3H), 7.5 (9H), 8.3 (1H).

EXAMPLE 153

D-α-[3-(2-o,p-dichloroanilino-4-hydroxy-5-pyrimidyl)-ureido]-p-hydroxybenzyl-penicillin-sodium Analogously to Example 134, starting from the reaction product of 810 mgm (0.003 mol) of 5-amino-2-o,p-dichloroanilino-4-hydroxy-pyrimidine with 300 mgm of phosgene and 0.4 ml of triethylamine as well as 1.26 gm of amoxycillin (0.003 mol).

Yield: 1.40 gm (68%) of sodium salt.

IR spectrum: 1770, 1660, 1615, 1555, 1520 $cm^{-1}$.

NMR spectrum (DMSO+$CD_3OD$) signals at ppm: 1.55 (6H), 4.05 (1H), 5.45 (m,3H), 6.85 (d,2H), 7.50 (m,5H), 8.40 (1H).

EXAMPLE 154

D-α-[3-(2-o,p-dichloroanilino-4-hydroxy-5-pyrimidyl)-ureido]-benzyl-penicillin-sodium Analogously to Example 134, starting from 4.03 gm of ampicillin-trihydrate (0.01 mol) and the reaction product of 2.71 gm (0.01 mol) of the pyrimidine of Example 153 with 1.05 gm of phosgene.

Yield: 5.15 gm of sodium salt (77%).

IR spectrum: 1770, 1660, 1615, 1555, 1320 $cm^{-1}$.

NMR spectrum (DMSO+$CD_3OD$) signals at ppm: 1.55 (6H), 4.05 (1H), 5.45 (q,2H), 5.55 (1H), 7.55 (m,8H), 8.35 (1H).

EXAMPLE 155

D-α-[3-(2-bromoanilino-4-hydroxy-5-pyrimidyl)-ureido]-p-hydroxy-penicillin-sodium This penicillin is prepared analogously to Example 134, starting from 2.1 gm of amoxycillin-trihydrate (0.005 mol) as well as the reaction product of 1.4 gm of 5-amino-2-p-bromoanilino-4-hydroxy-pyrimidine (0.005 mol) with 500 mgm of phosgene and 0.67 ml of triethylamine.

Yield: 4.4 gm of sodium salt (63%).

IR spectrum: 1770, 1660, 1610, 1550, 1520 $cm^{-1}$.

NMR spectrum (DMSO+$CD_3OD$) signals at ppm: 1.5 (6H), 4.0 (1H), 5.45 (3H), 6.8 (2H), 7.35 (4H), 7.8 (2H), 8.35 (1H).

EXAMPLE 156

D-α-[3-2-p-ethylanilino-4-hydroxy-pyrimidyl)-ureido]-p-hydroxy-benzyl-pencillin-sodium This penicillin is prepared analogously to Example 134, starting from 6.3 gm of amoxycillin-trihydrate (0.015 mol) as well as the reaction product of 3.45 gm of 5-amino-2-p-ethylanilino-4-hydroxy-pyrimidine with 1.5 gm of phosgene and 2.05 ml of triethylamine.

Yield: 7.15 gm of sodium salt (94%).

IR spectrum: 1770, 1660, 1610, 1550 $cm^{-1}$.

NMR spectrum (DMSO+$CD_3OD$) signals at ppm: 1.2 (3H), 1.55 (6H), 2.5 (2H), 4.05 (1H), 5.45 (3H), 6.75 (2H), 7.5 (6H), 8.2 (1H).

EXAMPLE 157

D-α-[3-(4-hydroxy-2-p-isopropylanilino-5-pyrimidyl)-ureido]-p-hydroxybenzyl-penicillin-sodium Analogously to Example 134, starting from 1.22 gm of 5-amino-4-hydroxy-2-p-isopropylanilino-pyrimidine (0.005 mol), which has firstly been reacted with 500 mgm of phosgene and 0.67 ml of triethylamine and then with 2.1 gm (0.005 mol) of amoxycillin. Yield 2.75 gm of sodium salt (83.5).

IR spectrum: 1765, 1665, 1615, 1550, 1520 $cm^{-1}$.

NMR spectrum ($D_2O$) signals at ppm: 1.25 (d,6H), 1.5 (d,6H), 2.8 (m,1H), 4.15 (1H), 5.45 (q,2H), 5.55 (1H), 6.9 (d,2H), 7.3 (m,4H), 7.7 (d,2H), 8.3 (1H).

EXAMPLE 158

D-α-[(2-p-dimethylaminoanilino-4-hydroxy-5-pyrimidyl)-ureido]-p-hydroxybenzyl-penicillin-sodium Analogously to Example 134, starting from 6.3 gm of amoxycillin-trihydrate (0.015 mol) and the reaction product of 3.65 gm of 5-amino2-p-dimethylaminoanilino-4-hydroxy-pyrimidin (0.015 mol) with 1.55 gm of phosgene and 2.05 mol of triethylamine.

Yield: 6.3 of sodium salt (64%).

IR spectrum: 1770, 1660, 1615, 1540, 1510 $cm^{-1}$.

NMR spectrum (DMSO+$CD_3OD$) signals at ppm: 1.55 (6H), 3.05 (6H), 4.05 (1H), 5.45 (q,2H), 5.50 (1H), 6.9 (d,2H), 7.25 (m,4H), 7.60 (d,2H), 8.35 (1H).

EXAMPLE 159

D-α-[3-(2-dimethylaminoanilino-4-hydroxy-5-pyrimidyl)-ureido]-benzyl-penicillin-sodium This penicillin is prepared analogously to Example 134, starting from 1.92 gm (0,00475 mol) of ampicillin-trihydrate as well as the reaction product of 1.16 gm (0.00475 mol) of the pyrimidine of Example 158 with 500 mgm of phosgene and 0.63 ml of triethylamine.

Yield: 2.05 gm of sodium salt (68%).

IR spectrum: 1770, 1660, 1615, 1540, 1520 $cm^{-1}$.

NMR spectrum (DMSO+$CD_3OD$) signals at ppm: 1.55 (6H), 3.1 (6H), 4.05 (1H), 5.35 (q,2H), 5.45 (1H), 7.45 (6H), 7.6 (2H), 8.3 (1H).

EXAMPLE 160

D-α-[3-(2-p-aminoanilino-4-hydroxy-5-pyrimidyl)-ureido]-p-hydroxy-benzyl-penicillin-sodium This penicillin is prepared analogously to Example 134, starting from 1.0 gm (0.00237 mol) of amoxicillin-trihydrate as well as the reaction product of 515 mgm (0.00237 mol) of 5-amino-2-p-aminoanilino-4-hydroxy-pyrimidine with 240 mgm of phosgene and 0.31 ml of triethylamine.

Yield: 670 mgm of sodium salt (43.5).

IR spectrum: 1770, 1650, 1600, 1550 $cm^{-1}$.

NMR spectrum (DMSO+$CD_3OD$) signals at ppm: 1.55 (6H), 4.05 (1H), 5.35 (2H), 5.45 (1H), 6.85 (2H), 2.75 (4H), 7.60 (2H), 8.35 (1H).

EXAMPLE 161

D-α-[3-(4-hydroxy-2-p-methylanilino-5-pyrimidyl)-ureido]-p-hydroxybenzyl-pencillin-sodium This penicillin is prepared by starting from 1.68 gm (0.004 mol) of amoxycillin-trihydrate and the reaction product of 860 mgm (0.004 mol) of 5-amino-4-hydroxy-2-p-methylanilino-pyrimidin with 405 mgm of phosgene and 0.54 ml of triethylamine. Treatment is effected in that the aqueous phase is firstly shaken twice with ethylacetate at pH 7.0, then covered with a layer of ethylacetate (100 ml) and brought with dilute hydrochloric acid to pH 2.0 with cooling. The precipitated product is filtered, washed with ether and dried. The organic phase is separated, the aqueous phase is shaken twice with ethylacetate, the organic phases are united and dried and the solvent is removed in vacuo. The product obtained is identical to the initially precipitated product according to DC (n-butanol-$CH_3$ COOH-$H_2O$=60:15:25). Both fractions are converted together into the sodium salt.

Yield: 1.89 gm (74.5%).

IR spectrum: 1770, 1665, 1605, 1550, 1510 $cm^{-1}$.

NMR spectrum (DMSO+$CD_3OD$) signals at ppm: 1.55 (6H), 4.05 (1H), 5.5 (m,3H), 6.85 (d,2H), 7.3 (m,4H), 7.7 (d,2H), 8.3 (1H).

EXAMPLE 162

D-α-[3-(4-hydroxy-2-p-methylanilino-5-pyrimidyl)-ureido]-benzyl-penicillin-sodium Preparation analogous to Example 134, starting from 3.71 gm (0.01 mol) of ampicillin-sodium as well as the reaction product of 2.15 gm (0.01 mol) of the pyrimidine of Example 161 with 1.05 gm of phosgene. During treatment the penicillin obtained is precipitated from water at pH 2.0, filtered off, washed with water and ether and dried.

Yield: 4.3 gm of sodium salt (69%).

IR spectrum: 1765, 1655, 1610, 1550, 1510 cm−1.

NMR spectrum (DMSO+$CD_3OD$) signals at ppm: 1.55 (6H), 2.3 (3H), 4.05 (1H), 5.45 (q,2H), 5.55 (1H), 7.35 (m,7H), 7.7 (d,2H), 8.35 (1H).

EXAMPLE 163

D-α-[3-(2-p-chloro-m-trifluoromethylanilino-4-hydroxy-5-pyrimidyl)-ureido-p-hydroxybenzyl-penicillin-sodium Preparation analogous to Example 134, starting from 2.1 gm of amoxycillin-trihydrate (0.005 mol) and the reaction product of 1.52 gm (0.005 mol) of 5-amino-2-(p-chloro-m-trifluoromethylanilino)-4-hydroxy-pyrimidine with 505 mgm of phosgene and 0.67 ml of triethylamine.

Yield: 2.74 gm of sodium salt (76%).

IR spectrum: 1765, 1650, 1610, 1545, 1501 $cm^{-1}$.

NMR spectrum (DMSO+$CD_3OD$) signals at ppm: 1.55 (6H), 4.05 (1H), 5.45 (q,2H), 5.55 (1H), 6.85 (d,2H), 7.5 (m,5H), 8.40 (1H).

EXAMPLE 164

D-α-[3-(4-hydroxy-2-p-nitroanilino-5-pyrimidyl)-ureido]-p-hydroxybenzyl-penicillin-sodium This penicillin is prepared by starting from 630 mgm of amoxicillin-trihydrate (0.0015 mol) and the reaction product of 365 mgm of 5-amino-4-hydroxy-2-nitroanilino-pyrimidine (0.0015 mol) with 150 mgm of phosgene and 0.20 ml of triethylamine (in 1 liter of absolute tetrahydrofurane).

Yield: 440 mgm of sodium salt (45%).

IR spectrum: 1770, 1660, 1615, 1550, 1510 $cm^{-1}$.

NMR spectrum (DMSO+$CD_3OD$) signals at ppm: 1.55 (6H), 4.10 (1H), 5.50 (q,2H), 5.60 (1H), 6.90 (d,2H), 7.3 (d,2H), 7.6 (d,2H), 7.90 (d,2H), 8.45 (1H).

EXAMPLE 165

D-α-[3-(2-p-amino-m,m-dichloroanilino-4-hydroxy-5-pyrimidyl)-ureido]-p-hydroxybenzyl-penicillin-sodium Preparation analogous to Example 134, starting from 1.26 gm of amoxycillin-trihydrate (0.003 mol) and the reaction product of 860 mgm (0.003 mol) of 5-amino-2-(p-amino-m,m-dichloroanilino)-4-hydroxy-pyrimidine with 300 mgm of phosgene and 0.41 of triethylamine.

Yield: 1.22 gm of sodium salt (58%).

IR spectrum: 1765, 1660, 1610, 1550, 1510 $cm^{-1}$.

NMR spectrum (DMSO+$CD_3OD$) signals at ppm: 1.55 (6H), 4.0 (1H), [5.4 (g,2H] 5.4 (q,2H), 5.5 (1H), 6.85 (d,2H), 7.4 (d,2H), 8.35 (1H).

EXAMPLE 166

D-α-[3(2-p-hydroxyanilino-4-hydroxy-5-pyrimidyl)-ureido]-p-hydroxybenzyl-penicillin-sodium This penicillin is snythezised analogously to Example 134, starting from 840 mgm (0.002 mol) of amoxycillin-trihydrate as well as the reaction product of 440 mgm of 5-amino-2-p-hydroxyanilino-4-hydroxy-pyrimidine (0.002 mol) with 205 mgm of phosgene and 0.27 ml of triethylamine.

Yield: 755 mgm (60%).

IR spectrum: 1765, 1660, 1610, 1550, 1510 $cm^{-1}$.

NMR spectrum (DMSO+$CD_3OD$) signals at ppm: 1.55 (6H), 4.0 (1H), 5.4 (q,2H), 5.5 (1H), 6.85 (m,4H), 7.4 (m,4H), 8.25 (1H).

EXAMPLE 167

D-α-[3-(2-p-hydroxyanilino-4-hydroxy-5-pyrimidyl)-ureido]-benzyl-penicillin-sodium Preparation analogous to Example 134, starting from 2.0 gm (0.0005 mol) of ampicillin-trihydrate and the reaction product of 1.08 gm (0.005 mol) of the pyrimidine of Example 166 with 505 mgm of phosgene and 0.67 ml of triethylamine.

Yield: 1.48 gm of sodium salt (48%).

IR spectrum: 1765, 1660, 1610, 1550, 1510 $cm^{-1}$.

NMR spectrum (DMSO+$CD_3OD$) signals at ppm: 1.55 (6H), 4.05 (1H), 5.45 (q,2H), 5.55 (1H), 6.85 (d,2H), 7.5 (m,7H), 3.30 (1H).

EXAMPLE 168

D-α-[3-(2-hydroxy-2-p-methylaminoanilino-5-pyrimidyl)-ureido]-p-hydroxybenzyl-penicillin-sodium This penicillin is prepared analogously to Example 134, starting from 1.5 gm of amoxicillin-trihydrate (0.00357mol) as well as the reaction product of 830 mgm of 5-amino-4-hydroxy-2-methylaminoanilino-pyrimidine with 370 mgm of phosgene and 0.5 ml of triethylamine.

Yield: 1.14 gm of sodium salt (51%).

IR spectrum: 1770, 1660, 1615, 1550 $cm^{-1}$.

NMR spectrum (DMSO+$CD_3OD$) signals at ppm: 1.55 (6H), 3.1 (3H), 4.05 (1H), 5.45 (3H), 6.85 (2H), 7.45 (4H), 7.6 (2H), 8.3 (1H).

EXAMPLE 169

D-α-[3-(4-hydroxy-2-p-methylsulfonylanilino-pyrimidyl)-ureido]-p-hydroxybenzyl-penicillin sodium This penicillin is prepared analogously to Example 134, starting from 3.5 gm of amoxicillin-trihydrate (0.0083 mol) as well as the reaction product of 2.35 (0.0085 mol) of 5-amino-4-hydroxy-2-methylsulfonyl-pyrimidine with 850 mgm of phosgene and 1.16 ml of triethylamine.

Yield: 3.95 gm of sodium salt (69.5%).

IR spectrum: 1770, 1650, 1600, 1535 $cm^{-1}$.

NMR spectrum (DMSO+$CD_3OD$) signals at ppm: 1.55 (6H), 2.9 (3H), 4.05 (1H), 5.45 (3H), 6.75 (2H), 7.35 (4H), 7.65 (2H), 8.30 (1H).

EXAMPLE 170

D-α-[3-(2-p-acetylanilino-4-hydroxy-5-pyrimidyl)-ureido]-p-hydroxybenzyl-penicillin-sodium This penicillin is prepared analogously to Example 134, starting from 4.2 gm (0.01 mol) of amoxicillin-trihydrate as well as the reaction product of 2.44 gm (0.01 mol) of 2-p-acetylanilino-5-amino-4-hydroxy-pyrimidine with 1.0 gm of phosgene and 1.37 ml of triethylamine.

Yield: 3.83 gm of sodium salt (58%).

IR spectrum: 1770, 1660, 1610, 1540 $cm^{-1}$.

NMR spectrum (DMSO+$CD_3OD$) signals at ppm: 1.55 (6H), 2.1 (3H), 4.05 (1H), 5.30 (g,2H), 5.45 (1H), 6.8 (2H), 7.35 (4H), 7.6 (2H), 3.35 (1H).

EXAMPLE 171

D-α-[3-(2-p-aminocarbonylanilino-4-hydroxy-5-pyrimidyl)-ureido]-p-hydroxybenzyl-penicillin-sodium This penicillin is prepared analogously to Example 129, starting from 2.1 gm of amoxicillin-trihydrate )0.005 mol) as well as the reaction product of 1.23 gm (0.005 mol) of 5-amino-2-p-aminocarbonylanilino-4-hydroxy-pyrimidine with 500 mgm of phosgene and 0.67 ml of triethylamine.

Yield: 2.45 gm of sodium salt (74%).

IR spectrum: 1770, 1650, 1600, 1530 $cm^{-1}$.

NMR spectrum (DMSO+$CD_3OD$) signals at ppm: 1.55 (6H), 4.1 (1H), 5.3 (q,2H), 5.4 (1H), 6.8 (2H), 7.3 (4H) 7.55 (2H), 8.25 (1H).

EXAMPLE 172

D-α-[3-(4-hydroxy-2-p-3'-methylureido-anilino:5-pyrimidyl)-ureido]-p-hydroxybenzyl-penicillin-sodium This penicillin is prepared analogously with Example 129, starting from 3.36 gm (0.008 mol) of amoxicillin-trihydrate as well as the reaction product of 2.2 gm (0.008 mol) of 5-amino-4-hydroxy-2-(-3'-methylureidoanilino)-pyrimidin with 800 mgm of phosgene and 1.1 ml of triethylamine.

Yield: 2.55 gm of sodium salt (46%).

IR spectrum: 1770, 1660, 1630, 1600, 1540 $cm^{-1}$.

NMR spectrum (DMSO+$CD_3OD$) signals at ppm: 1.55 (6H), 2.8 (3H), 4.05 (1H), 5.35 (q,2H), 5.45 (1H), 6.85 (2H), 7.35 (4H), 7.65 (2H), 8.35 (1H).

EXAMPLE 173

D-α-[3-(2-p-cyanoanilino-4-hydroxy-5-pyrimidyl)-ureido]-p-hydroxybenzyl-penicillin-sodium This penicillin is prepared analogously to Example 134, starting from 600 mgm of amoxicillin-trihydrate (0.00158 mol) as well as the reaction product of 350 mgm (0.0016 mol) of 5-amino-2-p-cyanoanilino-4-hydroxy-pyrimidine with 160 mgm of phosgene and 0.22 ml of triethylamine.

Yield: 490 mgm of sodium salt (50%).

IR spectrum: 2215, 1770, 1650, 1600, 1550 $cm^{-1}$.

NMR spectrum (DMSO+$CD_3OD$) signals at ppm: 1.50 (6H), 4.0 (1H), 5.35 (2H), 5.45 (1H), 6.85 (2H), 7.4 (4H), 7.75 (2H), 8.40 (1H).

EXAMPLE 174

D-α-[3-(4-hydroxy-2-m,p-dimethoxyanilino-5-pyrimidyl)-ureido]-p-hydroxybenzyl-penicillin sodium This penicillin is prepared analogously to Example 134, starting from 4.2 gm of amoxicillin-trihydrate (0.01 mol) as well as the reaction product of 2.62 gm of 5-amino-4-hydroxy-2-m,p-dimethoxyanilino-pyrimidine with 1.0 gm of phosgene and 1.37 ml of triethylamine.

Yield: 5.45 gm of sodium salt (81%).

IR spectrum: 1770, 1650, 1610, 1535 $cm^{-1}$.

NMR spectrum (DMSO+$CD_3OD$) signals at ppm: 1.55 (6H), 3.8 (3H), 3.85 (3H), 4.05 (1H), 5.5 (3H), 6.8–7.7 (7H), 8.3 (1H).

EXAMPLE 175

D-α-[3-(2-m,m-dichloroanilino-4-hydroxy-5-pyrimidyl)-ureido]-p-hydroxybenzyl-penicillin sodium This penicillin is prepared analogously to Example 134, starting from 1.0 gm of amoxicillin-trihydrate (0.00237 mol) as well as the reaction product of 670 mgm of 5-amino-2-m,m-dichloroanilino-4-hydroxy-pyrimidine (0.0024 mol) with 240 mgm of phosgene and 0.34 ml of triethylamine.

Yield: 1.55 gm of sodium salt (78.5%).

IR spectrum: 1770, 1660, 1610, 1600, 1540 $cm^{-1}$.

NMR spectrum (DMSO+$CD_3OD$) signals at ppm: 1.55 (6H), 4.1 (1H), 5.55 (3H), 6.9 (2H), 7.1 (1H), 7.4 (2H), 8.0 (2H), 8.5 (1H).

EXAMPLE 176

D-α-3-(2-m,m-dichloroanilino-4-hydroxy-5-pyrimidyl)-ureido]-benzyl-penicillin sodium This penicillin is prepared analogously to Example 134, starting from 1.34 gm (0.0036 mol) of ampicillin sodium as well as the reaction product of 1.02 gm (0.0036 mol) of the amine of Example 175 with 360 mgm of phosgene and 0.5 ml of triethylamine. Yield: 1.23 gm of sodium salt (59%).

IR spectrum: 1770, 1660, 1610, 1530 $cm^{-1}$.

NMR spectrum (DMSO+$CD_3OD$) signals at ppm: 1.55 (6H), 4.05 (1H), 5.4 (2H), 5.55 (1H), 7.1 (5H), 7.4 (5H), 7.9 (2H), 8.45 (1H).

EXAMPLE 177

D-α-[3-(2-m,p-dihydroxyanilino-4-hydroxy-5-pyrimidyl)-ureido]-p-hydroxybenzyl-penicillin sodium This penicillin is prepared analogously to Example 134, starting from 840 mgm (0.002 mol) of amoxicillin-trihydrate as well as the reaction product of 460 mgm (0.002 mol) of 5-amino-2-m,p-dihydroxyanilino-4-hydroxy-pyrimidine with 200 mgm of phosgene and 0.27 ml of triethylamine.

Yield: 790 mgm of sodium salt (60%).

IR spectrum: 1765, 1660, 1610, 1545 $cm^{-1}$.

NMR spectrum (DMSO+$CD_3OD$) signals at ppm: 1.55 (6H), 4.05 (1H), 5.4 (q,2H), 5.5 (1H), 6.85–7.5 (m,7H), 8.25 (1H).

EXAMPLE 178

D-α-[3-(2-m,p-dihydroxyanilino-4-hydroxy-5-pyrimidyl)-ureido]-benzyl-penicillin sodium This penicillin is prepared analogously to Example 177, starting fom 2.0 gm of ampicillin sodium (0.005 mol) as well as the reaction product of 1.15 gm (0.005 mol) of the pyrimidine of Example 177 with 0.5 gm of phosgene and 0.68 ml of triethylamine.

Yield: 1.59 gm of sodium salt (52%).

IR spectrum: 1765, 1650, 1600, 1545 $cm^{-1}$.

NMR spectrum (DMSO+$CD_3OD$) signals at ppm: 1.5 (6H), 4.0 (1H), 5.4 (q,2H), 5.5 (1H), 6.85–7.6 (m,8H), 8.2 (1H).

EXAMPLE 179

D-α-[3-(4-hydroxy-2-p-methylsulfinylanilino-5-pyrimidyl)-ureido]-p-hydroxybenzyl-penicillin sodium This penicillin is prepared analogously to Example 134, starting from 2.1 gm of amoxycillin-trihydrate (0.005 mol) as well as the reaction product of 1.32 gm of 5-amino-4-hydroxy-2-p-methylsulfinylanilino-pyrimidine with 500 mgm of phosgene and 0.68 ml of triethylamine.

Yield: 2.1 gm of sodium salt (65%).

IR spectrum: 1770, 1655, 1610, 1545 $cm^{-1}$.

NMR spectrum (DMSO+$CD_3OD$) signals at ppm: 1.55 (6H), 2.75 (3H), 4.05 (1H), 5.5 (3H), 6.8–7.9 (m,8H), 8.25 (1H).

The following are synthezised analogously to Example 134.

D-α-[3-(2-m,p-dichloroanilino-4-hydroxy-5-pyrimidyl)-ureido]-cyclohexa-1,4-diene-1-ylmethyl-penicillin sodium. D-α-[3-(2-m,p-dichloroanilino-4-hydroxy-5-pyrimidyl)-ureido]-m,p-dihydroxy-benzyl-penicillin sodium. D-α-[3-(2-m-chloroanilino-4-hydroxy-5-pyrimidyl)-ureido]-2-thienylmethyl-penicillin sodium.

[D-α[3-(2-m-chloroanilino-4-hydroxy-5-pyrimidyl)-[ureiod]-m,p-dihydroxybenzyl-pencillin sodium.]

*D-α-[3-(2-m-chloroanilino-4-hydroxy-5-pyrimidyl)-[ureido]-m,p-dihydroxybenzyl-penicillin sodium.*

[D-α-[3-(4-hydroxy-2-p-trifluoromethylanilino-5-pyrimidyl)-ureido]-cycloheza-1,4-diene-1-ylmethyl-penicillin sodium.]

*D-α-[3-(4-hydroxy-2-p-trifluoromethylanilino-5-pyrimidyl)-ureido]-cyclohexa-1,4-diene-1-ylmethyl-penicillin sodium.*

[D-α-[2-p-dimethylaminoanilino-4-hydroxy-5-pyrimidyl)-ureido]-cycloheza-1,4-diene-lylmethyl-pencillin sodium.]

*D-α-[3-(2-p-dimethylaminoanilino-*4-hydroxy-5-pyrimidyl)-ureido]-cyclohexa-1,4-diene-1-ylmethyl-penicillin sodium.

D-α-[3-(2-p-dimethylaminoanilino-4-hydroxy-5-pyrimidyl)-ureido]-2-thienylmethyl-pencillin sodium.

D-α-[3-(2-p-dimethylaminoanilino-4-hydroxy-5-pyrimidyl)-ureido]m,p-dihydroxybenzyl-penicillin sodium.

[D-α-[3-(4-hydroxy-2-p-methylanilino-5-pyrimidyl)-ureido]-cycloheza-1,4-diene-1-ylmethyl-penicillin sodium.]

*D-α-[3-(4-hydroxy-2-p-methylanilino-5-pyrimidyl)-ureido]-cyclohexa-1,4-diene-1-ylmethyl-penicillin sodium.*

D-α-[3-(4-hydroxy-2-p-methylanilino-5-pyrimidyl)-ureido]-n-chloro-p-hydroxybenzyl-penicillin sodium.

D-α-[3-(4-hydroxy-2-methylaminocarbonyl-5-pyrimidyl)-ureido]-m,p-dihydroxybenzyl-penicillin sodium.

[D-α-[3-(4-hydroxy-2-p-hydroxyanilino-5-pyrimidyl)-ureido]-cycloheza-1,4-diene-1-ylmethyl-penicillin sodium.]

*D-α-[3-(4-hydroxy-2-p-hydroxyanilino-5-pyrimidyl)-ureido]-cyclohexa-1,4-diene-1-ylmethyl-penicillin sodium.*

D-α-[3-(4-hydroxy-2-p-hydroxyanilino-5-pyrimidyl)-ureido]-benzyl-penicillin sodium.

D-α-[3-(4-hydroxy-2-p-methylaminoanilino-5-pyrimidyl)-ureido]-benzyl-penicillin sodium.

D-α-[-(2-m,m-dichloroanilino-4-hydroxy-5-pyrimidyl)-ureido]-cyclohexa-1,4-diene-1-yl-methyl-penicillin sodium.

D-α-[3-(4-hydroxy-2-methoxycarbonyl-5-pyrimidyl)-ureido]-m,p-dihydroxybenzyl-penicillin sodium.

D-α-[3-(4-hydroxy-2-methylcarbonyloxy-5-pyrimidyl)-ureido]-m,p-dihydroxybenzyl-penicillin sodium.

EXAMPLE 180

D-α-[3-(2-p-aminosulfonylanilino-4-hydroxy-5-pyrimidyl)-ureido]-p-hydroxybenzyl-penicillin sodium This penicillin is prepared analogously to Example 134, starting from 4.2 gm of amoxycillin-trihydrate as well as the reaction product of 2.8 gm (0.01 mol) of 5-amino-2-p-amino-sulfonylanilino-4-hydroxy-pyrimidine with 1.0 gm of phosgene and 1.35 ml of triethylamine.

Yield: 4.25 gm of sodium salt (62%)

IR spectrum: 1765, 1660, 1610, 1540 $cm^{-1}$.

NMR spectrum (DMSO+$CD_3OD$) signals at ppm: 1.55 (6H), 4.05 (1H), 5.4 (q,2H), 5.5 (1H), 6.8 (2H), 7.3 [(4H)] *(2H)*, 7.6 (2H), *7.95 (2H)*, 8.3 (1H).

EXAMPLE 181

D-α-[3-(2-benzylamino-4-hydroxy-5-pyrimidyl)-ureido]-p-hydroxybenzyl-penicillin sodium This penicillin is prepared analogously to Example 134, starting from 2.1 gm of amoxycillin-trihydrate (0.005 mol) as well as the reaction product of 1.08 gm (0.005 mol) of 5-amino-2-benzylamino-4-hydroxy-pyrimidine with 550 mgm of phosgene and 0.67 ml of triethylamine.

Yield: 2.03 gm of sodium salt (63.5%)

IR spectrum: 1770, 1670, 1600, 1530 $cm^{-1}$.

NMR spectrum (DMSO+$CD_3OD$) signals at ppm: 1.5 (6H), 4.0 (1H), 4.3 (2H), 5.5 (3H), 6.3 (2H), 7.4 (7H), 8.2 (1H),

EXAMPLE 182

D-α-[3-(2-p-chlorobenzylamino-4-hydroxy-5-pyrimidyl)-ureido]-p-hydroxybenzyl-penicillin sodium This penicillin is prepared analogously to Example 134, starting from 4.2 gm of amoxycillin-trihydrate (0.01 mol) as well as the reaction product of 2.51 gm (0.01 mol) of 5-amino-2-p-chlorobenzylamino-4-hydroxypyrimidine with 1.0 gm of phosgene ad 1.37 ml of triethylamine.

Yield: 5.52 gm sodium salt (82%).

IR spectrum: 1770, 1650, 1610, 1530 $cm^{-1}$. NRM spectrum (DMSO) signals at ppm: 1.55 (6H), 4.0 (1H), 4.4 (2H), 5.4 (q,2H), 5.5 (1H), 6.8 (2H), 7.4 (4H), 7.6 (2H), 8.2 (1H).

EXAMPLE 183

D-α-[3-(4-hydroxy-2-{N-methylanilino}-5-pyrimidyl-ureido]-p-hydroxybenzyl-penicillin sodium This penicillin is prepared analogously to Example 134, starting from 1.75 gm of amoxicillin-trihydrate (0.0042 mol) as well as the reaction product of 950 mgm (0.0042 mol) of 5-amino-4-hydroxy-2-(N-methylanilino)-pyrimidine with 420 mgm of phosgene and 0.57 ml of triethylamine.

Yield: 1.72 gm of sodium salt (64%).

IR spectrum: 1770, 1660, 1610, 1530 $cm^{-1}$.

NMR spectrum (DMSO+$CD_3OD$) signals at ppm: 1.55 (6H), 3.3 (3H), 4.0 (1H), 5.5 (3H), 6.8 (2H), 7.4 (7H), 8.1 (1H).

EXAMPLE 184

D-α-[3-(4-hydroxy-2-{2'-phenylethylamino}-5-pyrimidyl)-ureido]-p-hydroxybenzyl-penicillin sodium This penicillin is prepared analogously to Example 134, starting from 1.05 gm of amoxicillin-trihydrate (0.0025 mol) as well as the reaction product of 540 mgm of 5-amino-4-hydroxy-2-(2'-phenylethylamino)-pyrimidine (0.0025 mol) with 250 mgm of phosgene and 0.34 ml of triethylamine.

Yield: 1.04 gm of sodium salt (66%).

IR spectrum-1770, 1660, 1605, 1530 $cm^{-1}$. NMR spectrum (DMSO+$CD_3OD$) signals at ppm: 1.55 (6H), 2.8 (2H), 3.65 (2H), 4.0 (1H), 5.5 (3H), 6.8 (2H), 7.4 (7H), 8.1 (1H).

EXAMPLE 185

D-α-[3-(4-hydroxy-2-{1'-phenyl-ethylamino}-pyrimidyl)-ureido]-p-hydroxybenzyl-penicillin sodium This penicillin was prepared analogously to Example 128. One starts from 2.1 gm amoxicillin-trihydrate (0.005 mol) and the reaction product of 1.08 gm of 5-amino-4-hydroxy-2-(1'-phenyl-ethylamino)-pyrimidine (0.005 mol) with 500 mgm phosgene and 0.67 ml triethylamine.

Yield: 1.94 gm of sodium salt (61.5%).

IR spectrum: 1770, 1660, 1610, 1610, 1540 $cm^{-1}$.

NMR spectrum (DMSO+$CD_3OD$) signals at ppm: 1.5 (m,9H), 4.1 (1H), 5.4 (2H), 5.5 (1H), 6.8 (2H), 7.4 (7H), 8.05 (1H).

Analogously were prepared:

D-α-[3-(2-benzylamino-4-hydroxy-5-pyrimidyl)-ureido]-m,p-dihydroxybenzyl-penicillin sodium.

D-α-[3-(2-p-chlorobenzylamino-4-hydroxy-5-pyrimidyl)-ureido]-m,p-dihydroxybenzyl-penicillian sodium.

D-α-[3-(4-hydroxy-2-{N-methyl-anilino}-5-pyrimidyl)-ureido]-benzyl-penicillin sodium.

D-α-[3-(4-hydroxy-2-{2'-phenyl-ethylamino}-5-pyrimidyl)-ureido]-m,p-dihydroxybenzyl-penicillin sodium.

D-α-{3-(4-hydroxy-2-{2'-phenyl-ethylamino}-5-pyrimidyl)-ureido]-2-thienylmethyl-penicillin sodium.

D-α-[3-(4-hydroxy-2-p-hydroxybenzylamino-5-pyrimidyl)-ureido]-m,p-dihydroxybenzyl-penicillin sodium.

D-α-[3-(2-m,p-dihydroxy-benzylamino-4-hydroxy-5-pyrimidyl)-ureido]-m,p-dihydroxybenzyl-penicillin sodium.

D-α-[3-(4-hydroxy-2-p-hydroxy-m-methoxy-benzylamino-5-pyrimidyl)-ureido]-p-hydroxybenzyl-penicillin sodium.

D-α-[3-(2-amino-m,m-dichloro-benzylamino-4-hydroxy-5-pyrimidyl)-ureido]-p-hydroxybenzyl-penicillin sodium.

D-α-[3-(2-{2'-p-chlorophenyl-ethylamino}-4-hydroxy-5-pyrimidyl)-ureido]-p-hydroxybenzyl-penicillin sodium D-α-[3(4-hydroxy-2-{2'-m,p-dihydroxyphenyl-ethylamino}-5-pyrimidyl)-ureido]-cyclohexa-1,4-dien-1-ylmethyl-penicillin sodium.

D-α-[3-(4-hydroxy-2-{2'-m,m,p-trimethoxyphenyl-ethylamino}-5-pyrimidyl)-ureido]-cyclohexa-1,4-diene-1-ylmethyl-penicillin sodium.

D-α-[3-(2-{1'-p-chlorophenyl-ethylamino}-4-hydroxy-5-pyrimidyl)-ureido]-p-hydroxybenzyl-penicillin sodium.

D-α-[3-(2-{1'-m,p-dimethoxyphenyl-ethylamino}-4-hydroxy-5-pyrimidyl)-ureido]-p-hydroxybenzyl-penicillin sodium.

EXAMPLE 186

D-α-[3-(2-p-chloroanilino-4-hydroxy-5-pyrimidyl)-ureido]-benzyl-penicillin sodium To a suspension of 2.3 gm (0.005 mol) D-α-[(2-p-chloroanilino-4-hydroxy-5-pyrimidyl)-ureido]-phenylglycinesodium salt in 25 ml anhydrous acetone is added 10 mgm N-methylmorphine. One cools to −20° to −15° C. and adds dropwise at this temperature to a solution of 550 mgm ethyl chloroformate (0.005 mol) in 10 ml anhydrous acetone. One stirs at −20° C. for one hour. Subsequently a solution of 1.6 gm of the triethylammonium salt of 6-amino-penicillanic acid in 10 ml anhydrous methylene chloride is added thereto at this temperature. One stirs for one hour at −20° C., for one hour at 0° C. and for one hour at room temperature. The organic solvent is removed under vacuum and the residue is dissolved in a mixture of 40 ml water and 60 ml ethyl acetate at pH 7.0. The aqueous phase is separated, extracted with 100 ml ethyl acetate and with cooling brought to pH 2.0 with dilute hydrochloric acid. The organic phase is separated, dried and the solvent is removed under vacuum. The sodium salt is obtained with sodium ethylhexanoate.

Yield: 2.05 gm (61%)

IR spectrum: 1770, 1660, 1610, 1545, 1515 $cm^{-1}$.

NMR spectrum (DMSO+$CD_3OD$) signals at ppm; 1.55 (6H), 4.1 (1H), 5.5 (q,2H), 5.55 (1H), 7.5 (m,5H), 7.9 (d,2H), 8.45 (1H).

Analogously were prepared:

D-α-[3-(4-hydroxy-2-o-methylanilino-5-pyrimidyl)-ureido]-benzyl-penicillin sodium.

D-α-[3-(2-(p-chloro-m-trifluoromethylanilino)-4-hydroxy-5-pyrimidyl)-ureido]-benzyl-penicillin sodium.

D-α-[3-(2-p-bromoanilino-4-hydroxy-5-pyrimidyl)-ureido]-benzyl-penicillin sodium.

EXAMPLE 187

D-α-[3-(2-p-acetylaminoanilino-4-hydroxy-5-pyrimidyl)ureido]-m,p-dihydroxybenzyl-penicillin sodium 2.16 gm (0.01 mol) of anhydrous 6-amino-pencillanic acid were silylated with 2.5 ml N,O-(bristrimethylsilyl-)acetamide in dry dimethylformamide at room temperature. The solution obtained was added dropwise at −10° C. to a solution prepared at −20° C. (see Example 186) from 4.9 gm (0.01 mol) D-α-[3-(2-p-acetylaminoanilino-4-hydroxy-5-pyrimidyl)-ureido]-m,p-dihydroxy-phenylglycine, 1.1 gm ethyl chloroformate and 1.05 gm N-methylmorpholine. For further reaction and workup see Example 186.

Yield: 3.54 gm sodium salt (49%).

IR spectrum: 1770, 1650, 1610, 1545, 1510 $cm^{-1}$.

NMR spectrum (DMSO+$CD_3OD$) signals at ppm: 1.55 (6H), 2.10 (3H), 4.05 (1H), 5.45 (q,2H), 5.55 (1H), 7.3 (m,5H), 7.6 (d,2H), 8.30 (1H).

EXAMPLE 188

D-α-[3-(2-acetylamino-4-hydroxy-5-pyrimidyl)-ureido]-benzylpenicillin sodium 2.0 gm (0.00125 mol) 5-amino-4-hydroxy-2-acetylaminopyrimidine (prepared by catalytic hydrogenation of the corresponding nitro compound as described in JACS 1964, p. 5668) was dissolved in absolute tetrahydrofuran. At 0° C. 1.2 gm triethylamine were added and the mixture obtained was added dropwise to 1.3 gm phosgene dissolved in tetrahydrofuran. It was stirred for 30 minutes at 0° C. Excess phosgene was removed with nitrogen and the mixture was concentrated to 50 ml. Triethylamine was removed from the mixture by filtration. 2.5 gm ampicillin-trihydrate (6 millimols) were suspended in 50 ml 80% aqueous tetrahydrofuran. Triethylamine was dissolved with cooling and stirring until the ampicillin had a pH of about 8. To this solution was added dropwise the above mixture whereby the pH of the mixture due to addition of triethylamine became about 7.5. Stirring was continued until maintenance of this pH value did not require the addition of base. Then the mixture was diluted with 50 ml water, the pH altered to 7.0 and the tetrahydrofuran was removed on a rotary evaporator. The remaining aqueous solution was adjusted to pH 7.0 and extracted with acetate ester, then distributed in approximately 200 ml acetate ester and, with stirring and cooling, was carefully brought to pH 2.0 with 2 N hydrochloric acid. The organic phase was separated off, any undissolved product was filtered off and the aqueous phase was again extracted with acetic ester. The combined acetic ester extracts were washed with a saturated salt solution and dried over sodium sulphate.

After removal of the solvent a colorless residue remained which was dissolved in 30 ml absolute methanol and diluted with 100 ml absolute ether. By addition of a solution of sodium 2-ethylhexanoate in ether the sodium salt precipitated out.

Yield: 1.2 gm (34%).

Rf: 0.57

IR spectrum: 1770, 1660, 1610, 1525 $cm^{-1}$.

NMR spectrum: ($D_2O$) signals at ppm: 1.4 (3H), 1.5(3H), 2.3 (3H), 4.2 (1H), 5.3–5.6 (3H), 7.5 (5H), 8.2 (1H).

EXAMPLE 189

D-α-[3-(acetylamino-4-hydroxy-pyrimidyl)-ureido]-p-hydroxybenzyl-penicillin sodium 3.36 gm 2-Acetylamino-5-amino-4-hydroxy-pyrimidine (0.02 mol) were heated for one hour to 80° C. with 10 ml hexamethyldisilazane. The solid product remaining after removal of excess silylating agent was dissolved in 20 ml absolute tetrahydrofuran, mixed with 2.0 gm triethylamine and, with ice cooling, added dropwise to a solution of 2.1 gm phosgene in 30 ml absolute tetrahydrofuran. The triethylamine hydrochloride thus formed was removed under nitrogen.

This solution was added dropwise at 0° C. to a solution prepared from 8.4 gm amoxycillin-trihydrate (0.02 mol) in 80% tetrahydrofuran containing triethylamine at pH 7.8. By addition of triethylamine the pH was maintained at about pH 7.5. The product was obtained as described in previous Example.

Yield: 5.7 gm (48%) sodium salt.

Rf: 0.54

IR spectrum: 1760, 1650, 1600, 1510 $cm^{-1}$.

NMR spectrum: ($D_2O$) in ppm: 1.45 (3H), 1.55 (3H), 2.3 (3H), 4.25 (1H), 5.3 (1H), 5.5 (2H), 7.2 (4H), 8.3 (1H).

EXAMPLE 190

D-α-[3-(4-hydroxy-2-propionylamino-5-pyrimidyl)-ureido]-benzyl-penicillin sodium From 2.4 gm ampicillin-trihydrate (0.006 mol) and the reaction product of 1.1 gm 5-amino-4-hydroxy-2-propionylamino-pyrimidine (0.006 mol), 600 mgm phosgene and 600 mgm triethylamine in tetrahydrofuran.

Yield: 2.55 gm (75%).

Rf: 0.66

IR spectrum: 1770, 1660, 1610, 1520 $cm^{-1}$.

NMR signal ($CD_3OD$) in ppm: 1.2–1.5 (t,3H), 1.5 (3H), 1.6 (3H), 2.5 (q,2H), 4.2 (1H), 5.6 (m,3H), 7.5 (5H), 8.4 (1H).

EXAMPLE 191

D-α-[3-(4-hydroxy-2-propionylamino-5-pyrimidyl)-ureido]-p-hydroxybenzyl-penicillin sodium 2.52 gm amoxycillin-trihydrate (0.006 mol) were suspended in 50 ml 80% aqueous tetrahydrofuran. Sufficient triethylamine was then dissolved therein with cooling and stirring such that the pH of the amoxycillin was about pH 8.5.

1.15 gm 5-amino-4-hydroxy-2-propionylamino-pyrimidine (0.006 mol) were treated in tetrahydrofuran with ice cooling with 0.6 gm phosgene and 0.6 gm triethylamine. The obtained mixture was concentrated to 40 ml and with ice cooling added dropwise to the above solution. By addition of triethylamine the pH was maintained fixed at 7.5. Stirring was continued until the pH became constant.

The product was obtained analogously to Example 188.

Yield: 1.7 gm (46%).

Rf: 0.67.

IR spectrum: 1765, 1650, 1610, 1510 $cm^{-1}$.

NMR signal ($D_2O$) in ppm: 1.1–1.3 (t,3H), 1.4 (1H), 1.5 (1H), 2.5 (2H), 4.2 (1H), 5.2 (1H), 5.5 (2H), 7.1 (4H), 8.2 (1H).

EXAMPLE 192

D-α-[3-(4-hydroxy-2-isobutyrylamino-5-pyrimidyl)-ureido]-benzyl-penicillin sodium From 2.4 gm ampicillin-trihydrate and the reaction product of 1.17 gm 5-amino-4-hydroxy-2-isobutyrylaminopyrimidine and phosgene.

Yield: 58%.

Rf: 0.77

IR spectrum: 1765, 1660, 1600, 1525 $cm^{-1}$.

NMR signal ($D_2O$) at ppm: 1.2 (m,6H), 1.4 (3H), 1.5 (3H), 2.7 (m,1H), 4.2 (s,1H), 5.5 (m,3H), 7.5 (5H), 8.2 (1H).

EXAMPLE 193

D-α-[3-(4-hydroxy-2-isobutyrylamino-5-pyrimidyl)-ureido]-p-hydroxy-benzyl-penicillin sodium This penicillin was prepared analogously to Example 189. One starts from 2.1 gm amoxycillin-trihydrate (0.005 mol) and the reaction product of 980 mgm (0.005 mol) 5-amino-4-hydroxy-2-isobutyrylamino-pyrimidine with 500 mgm phosgene and 0.67 ml triethylamine.

Yield: 2.05 gm sodium salt (66%).

IR spectrum: 1770, 1660, 1610, 1520 $cm^{-1}$.

EXAMPLE 194

D-α-[3-(4-hydroxy-2-valeroylamino-5-pyrimidyl)-ureido]-p-hydroxybenzyl-penicillin sodium This penicillin was prepared analogously to Example 188. One starts from 4.2 gm amoxycillin-trihydrate (0.01 mol) and the reaction product of 2.1 gm 5-amino-4-hydroxy-2-valeroylamino-pyrimidine (0.01 mol) with 1.0 gm phosgene and 1.37 ml triethylamine.

Yield: 3.64 gm sodium salt (58%).

IR spectrum: 1770, 1660, 1615, 1525 $cm^{-1}$.

NMR spectrum: (DMSO+$CD_3OD$) signals at ppm: 1.1 (3H), 1.55 (6H), 2.1 (4H), 2.5 (2H), 4.05 (1H), 5.35 (2H), 5.45 (1H), 6.85 (2H), 7.4 (2H), 8.4 (1H).

EXAMPLE 195

D-α-[3-(2-cyclopropionylamino-4-hydroxy-5-pyrimidyl)-ureido]-p-hydroxybenzyl-penicillin sodium This penicillin was prepared analogously to Example 188. One starts from 2.1 gm (0.005 mol) amoxycillin-trihydrate and the reaction product of 970 mgm 5-amino-2-cyclopropionylamino-4-hydroxy-pyrimidine. (0.005 mol) with 500 mgm phosgene and 0.76 ml triethylamine.

Yield: 2.13 gm sodium salt (68.5%).

IR spectrum: 1770, 1665, 1610, 1540 $cm^{-}$.

NMR spectrum (DMSO+$CD_3OD$) signals at ppm: 0.9 (4H), 1.55 (6H), 2.1 (1H), 4.05 (1H), 5.45 (3H), 6.9 (2H), 7.4 (2H), 8.5 (1H).

EXAMPLE 196

D-α-[3-(2-cyclopropionylamino-4-hydroxy-5-pyrimidyl)-ureido]-benzyl-penicillin sodium This penicillin was prepared analogously to Example 188. One starts from 3.71 gm ampicillin-sodium (0.01 mol) and the reaction product of 1.94 gm (0.01 mol) of the amine of Example 182 with 1.0 gm phosgene and 1.37 ml triethylamine.

Yield: 3.55 gm sodium salt (69%).

IR spectrum: 1770, 1660, 1605, 1525 $cm^{-1}$.

NME spectrum (DMSO+$CD_3OD$) signals at ppm: 0.9 (4H), 1.55 (6H), 2.05 (1H), 4.0 (1H), 5.45 (3H), 7.45 (5H), 8.45 (1H).

EXAMPLE 197

D-α-[3-(2-cyclohexanoylamino-4-hydroxy-5-pyrimidyl)-ureido]-p-hydroxybenzyl-penicillin sodium This penicillin was prepared analogously to Example 188. One starts from 420 mgm amoxycillin-trihydrate (0.001 mol) and the reaction product of 240 mgm (0.001 mol) 5-amino-2-cyclohexanoylamino-4-hydroxy-pyridine with 100 mgm phosgene and 0.14 ml triethylamine.

Yield: 290 mgm sodium salt (44.5%).

IR spectrum: 1770, 1665, 1610, 1535 $cm^{-1}$.

NMR spectrum (DMSO+$CD_3OD$) signals at ppm: 0.8-1.3 (10H), 2.3 (1H), 4.05 (1H), 5.40 (3H), 6.8 (2H), 7.35 (2H), 8.40 (1H).

EXAMPLE 198

D-α-[3-(2-formylamino-4-hydroxy-5-pyrimidyl)-ureido]-p-hydroxybenzyl-penicillin sodium This penicillin was prepared analogously to Example 189, one starts from 2.34 gm amoxycillin-trihydrate (0.0056 mol) and the reaction product of 860 mgm (0.0056 mol) 5-amino-2-formylamino-4-hydroxypyrimidine with 560 mgm phosgene and 0.77 ml triethylamine.

Yield: 1.88 gm sodium salt (33%).

IR spectrum: 1770, 1660, 1640, 1610, 1525 $cm^{-1}$,

NMR spectrum (DMSO+$CD_3OD$) signals at ppm: 1.55 (6H), 4.1 (1H), 5.35 (2H), 5.45 (1H), 6.85 (2H), 7.45 (2H), 8.20 (1H), 8.45 (1H).

EXAMPLE 199

D-α-[3-(2-formylamino-4-hydroxy-5-pyrimidyl)-ureido]-benzylpenicillin sodium

This penicillin was prepared analogously to Example 198. One starts from 1.0 gm ampicillin-sodium (0.0027 mol) and the reaction product of 415 mgm of the amine of Example 198 (0.0027 mol) with 270 mgm phosgene and 0.37 ml triethylamine.

Yield: 355 mgm sodium salt (26%).

IR spectrum: 1770, 1660, 1635, 1605, 1520 $cm^{-1}$.

NMR spectrum (DMSO+$CD_3OD$) signals at ppm: 1.55 (6H), 4.0 (1H), 5.35 (2H), 5.45 (1H), 7.45 (5H), 8.15 (1H), 8.45 (1H).

EXAMPLE 200

D-α-[3-(2-benzoylamino-4-hydroxy-5-pyrimidyl)-ureido]-p-hydroxybenzyl-penicillin sodium This penicillin was prepared analogously to Example 188. One starts from 201 gm amoxycillin-trihydrate (0.005 mol) and the reaction product of 1.1 gm (0.005 mol) 5-amino-benzoylamino-4-hydroxy-pyrimidine with 500 mgm phosgene and 0.67 triethylamine.

Yield: 2.0 sodium salt (65%).

IR spectrum: 1770, 1660, 1605, 1550 $cm^{-1}$.

NMR spectrum (DMSO+$CD_3OD$) signals at ppm: 1.55 (6H), 4.05 (1H), 5.45 (q,2H), 5.50 (1H), 6.8 (2H), 7.3 (2H), 7.6 (3H), 8.1 (2H), 8.5 (1H).

EXAMPLE 201

D-α-[3-(4-hydroxy-2-trifluoroacetylamino-5-pyrimidyl)-ureido]-benzyl-penicillin sodium From 1.2 gm ampicillin-trihydrate (0.00295 mol) and the reaction product of 660 mgm 5-amino-4-hydroxy-2-trifluoroacetylamino-pyrimidine (0.003 mol), 230 mgm phosgene and 0.4 ml triethylamine as in Example 188.

Yield: 340 mgm (36.5%).

NMR signals ($D_2O$) at ppm: 1.4 (3H), 1.5 (3H), 4.2 (1H), 5.3-5.6 (dd,2H), 5.3 (1H), 7.5 (5H), 8.4 (1H).

EXAMPLE 202

D-α-[3-(4-hydroxy-2-trifluoroacetylamino-5-pyrimidyl)-ureido]-p-hydroxybenzyl-penicillin sodium This penicillin was prepared analogously to Example 188. One starts from 2.1 gm amoxicillin-trihydrate (0.005 mol) and the reaction product of 1.11 gm (0.005 mol) of the amine of Example 201 with 500 mgm phosgene and 0.67 ml triethylamine.

Yield: 1.24 gm sodium salt (39%).

IR spectrum: 1770, 1665, 1610, 1535 $cm^{-1}$.

NMR spectrum (DMSO+$CD_3OD$) signals at ppm: 1.55 (6H), 4.05 (1H), 5.45 (2H), 5.50 (1H), 6.8 (2H), 7.4 (2H), 8.45 (1H).

EXAMPLE 203

D-α-[3-(4-hydroxy-2-pentafluoropropionylaminopyrimidyl)-ureido]-p-hydroxybenzyl-penicillin sodium This penicillin was prepared analogously to Example 188. One starts from 1.0 gm amoxicillin-trihydrate (0.00237 mol) and the reaction product of 650 mgm 5-amino-4-hydroxy-2-pentafluoropropionyl-pyrimidine (0.0024 mol) with 140 mgm phosgene and 0.33 ml. triethylamine.

Yield: 655 mgm sodium salt (40.5%).

IR spectrum: 1770, 1660, 1610, 1525 $cm^{-1}$.

NMR spectrum: (DMSO+$CD_3OD$) signals at ppm: 1.55 (6H), 4.05 (1H), 5.35 (1H), 5.40 (2H), 6.85 (2H), 7.45 (2H), 8.45 (1H).

EXAMPLE 204

D-α-[3-(4-hydroxy-2-perfluorobutyryl-5-pyrimidyl-)ureido]-p-hydroxybenzyl-penicillin sodium This penicillin was prepared analogously to Example 188. One starts from 2.1 gm amoxycillin-trihydrate (0.005 mol) and the reaction product of 1.61 gm (0.005 mol) 5-amino-2-heptafluoropropionyl-4-hydroxypyrimidine with 500 mgm phosgene and 0.67 ml triethylamine.

Yield: 1.48 gm sodium salt (37%).

IR spectrum: 1770, 1665, 1600, 1525 $cm^{-1}$.

NMR spectrum (DMSO+$CD_3OD$) signals at ppm: 1.55 (6H), 4.0 (1H), 5.35 (1H), 5.40 (2H), 6.85 (2H), 7.45 (2H), 8.50 (1H).

EXAMPLE 205

D-α-[3-(2-ethoxycarbonylamino-4-hydroxy-5-pyrimidyl)ureido]-p-hydroxybenzyl-penicillin sodium This penicillin was prepared analogously to Example 183. One starts from 800 mgm amoxycillin-trihydrate (0.0019 mol) and the reaction product of 380 mgm 5-amino-2-ethoxycarbonylamino-4-hydroxy-pyrimidine (0.0019 mol) with 200 mgm phosgene and 0.32 ml triethylamine.

Yield: 800 mgm sodium salt (74%).

IR spectrum: 1770, 1690, 1660, 1610, 1550 $cm^{-1}$,

NMR spectrum (DMSO+$CD_3OD$) signals at ppm: 1.3 (3H), 1.55 (6H), 4.05 (1H), 4.2 (2H), 5.45 (3H), 6.85 (2H), 7.35 (2H), 8.40 (1H).

EXAMPLE 206

D-α-3-(2-{3'-dimethyl-ureido}-4-hydroxy-5-pyrimidiyl)-ureido]p-hydroxybenzyl-penicillin sodium This penicillin was prepared analogously to Example 189. One starts from 840 mgm amoxicillin-trihydrate (0.002 mol) and the reaction product of 395 mgm (0.002 mol) 5-amino-2-(3'-dimethyl-ureido)-4-hydroxy-pyrimidine with 200 gm phosgene and 0.33 ml triethylamine.

Yield: 550 mgm sodium salt (45%).

IR spectrum: 1770, 1670, 1610, 1525 $cm^{-1}$.

NMR spectrum (DMSO+$CD_3OD$) signals at ppm: 1.55 (6H), 2.75 (6H), 4.1 (1H), 5.45 (3H), 6.85 (2H), 7.35 (2H), 8.40 (1H).

EXAMPLE 207

D-α-[3-(4-hydroxy-2-{3'-methyl-ureido}-5-pyrimidyl)-ureido]-p-hydroxybenzyl-penicillin sodium This penicillin was prepared analogously to Example 189. One starts from 2.1 gm amoxycillin-trihydrate (0.005 mol) and the reaction product of 900 mgm 5-amino-4-hydroxy-2-(3'-methyl-ureido)-pyrimidine (0.005 mol) with 500 mgm phosgene and 0.67 ml triethylamine.

Yield: 126 gm sodium salt (41%).

IR spectrum: 1770, 1660, 1610, 1540 $cm^{-1}$.

NMR spectrum (DMSO+$CD_3OD$) signals at ppm: 1.55 (6H), 2.7 (3H), 4.05 (1H), 5.4 (2H), 5.45 (1H), 6.85 (2H), 7.35 (2H), 8.45 (1H).

EXAMPLE 208

D-α-[3-(4-hydroxy-2-ureido-5-pyrimidyl)-ureido]-p-hydroxybenzyl-penicillin sodium This penicillin was prepared ananlogously to Example 189. One starts from 2.1 gm amoxycillin-trihydrate (0.005 mol) and the reaction product of 850 mgm 5-amino-4-hydroxy-2-ureido-pyrimidine (0.005 mol) with 500 mgm phosgene and 0.67 ml triethylamine.

Yield: 650 mgm sodium salt (23%).

IR spectrum: 1770, 1665, 1615, 1530 $cm^{-1}$.

NMR spectrum (DMSO+$CD_3OD$) signals at ppm: 1.55 (6H), 4.0 (1H),(5.35 (1H), 5.45 (2H), 6.85 (2H), 7.45 (2H), 8.5 (1H).

EXAMPLE 209

D-α-[3-(2-{3-cyclopropyl-ureido}-4-hydroxy-5-pyrimidyl)-ureido]-p-hydroxybenzyl-penicillin sodium This penicillin was prepared analogously to Example 188. One starts from 420 mgm amoxycillin-trihydrate (0.005 mol) and the reaction product of 200 mgm (0.005 mol) 5-amino-2-(3'-cyclopropyl-ureido)-4-hydroxypyrimidine with 500 mgm phosgene and 0.67 ml triethylamine.

Yield: 162 gm sodium salt (52%).

IR spectrum: 1770, 1660, 1610, 1520 $cm^{-1}$.

NMR spectrum (CMSO+$CD_3OD$) signals at ppm: 1.1 (4H), 1.55 (6H), 2.3 (1H), 4.05 (1H), 5.45 (3H), 6.85 (2H), 2.40 (2H), 8.45 (1H).

EXAMPLE 210

D-α-[3-(4-hydroxy-2-(3'-phenyl)-ureido-5-pyrimidyl)-ureido]-p-hydroxybenzyl-penicillin sodium This penicillin is prepared analogously to Example 188. One starts from 4.2 gm amoxycillin-trihydrate (0.01 mol) and the reaction product of 1.17 gm (0.005 mol) 5-amino-4-hydroxy-2-(3'-phenyl)-ureido-pyrimidine with 1.0 gm phosgene and 1.37 ml triethylamine.

Yield: 4.23 gm sodium salt (64.5%).

IR spectrum: 1770, 1670, 1615, 1545, 1510 $cm^{-1}$.

NMR spectrum (DMSO+$CD_3OD$) signals at ppm: 1.55 (6H), 4.0 (1H), 5.45 (3H), 6.9 (2H), 7.5 (7H), 8.40 (1H).

EXAMPLE 211

D-α-[3-(4-hydroxy-2-pyrrolidino-carbonyl-amino-5-pyrimidyl)-ureido]-p-hydroxybenzyl-penicillin sodium This penicillin was prepared analogously to Example 188. One starts from 840 mgm amoxycillin-trihydrate (0.002 mol) and the reaction product of 450 mgm (0.002 mol) 5-amino-4-hydroxy-2-(pyrrolidino-carbonyl)- amino-pyrimidine with 200 mgm phosgene and 0.27 ml triethylamine.

Yield: 625 mgm sodium salt (48%).

IR spectrum: 1770, 1660, 1620, 1530 $cm^{-1}$.

NMR spectrum (DMSO+$CD_3OD$) signals at ppm: 1.55 (5H), 2.0 (4H), 3.4 (4H), 4.05 (1H), 5.35 (1H), 5.40 (2H), 6.85 (2H), 7.40 (2H), 8.35 (1H).

Analogously were prepared:

D-α-[3-(2-formylamino-4-hydroxy-5-pyrimidyl)-ureido]-m-chloro-p-hydroxybenzyl-penicillin.

D-α-[3-(2-formylamino-4-hydroxy-5-pyrimidyl)-ureido]-cyclohexa-1,4-dien-1-yl-methyl-penicillin sodium.

D-α-[3-(2-formylamino-4-hydroxy-5-pyrimidyl)-ureido]-2-thienyl-methyl-penicillin sodium.

D-α-[3-(2-formylamino-4-hydroxy-5-pyrimidyl)-ureido]-m,p-dihydroxybenzyl-penicillin sodium.

D-α-[3-(2-acetylamino-4-hydroxy-5-pyrimidyl)-ureido]-cyclohexa-1,4-dien-1-yl-methyl-penicillin sodium.

D-α-[3-(2-acetylamino-4-hydroxy-5-pyrimidyl)-ureido-2-thienyl-methyl-penicillin sodium.

D-α-[3-(2-acetylamino-4-hydroxy-5-pyrimidyl-ureido]-m,p-dihydroxybenzyl-penicillin sodium.

D-α-[3-(2-acetylamino-4-hydroxy-5-pyrimidyl)-ureido]-m-chloro-p-hydroxybenzyl-penicillin sodium.

D-α-[3-(4-hydroxy-2-propionylamino-5-pyrimidyl)-ureido]-cyclohexa-1,4-dien-1-yl-methyl-penicillin sodium.

D-α-[3-(4-hydroxy-2-pripionylamino-5-pyrimidyl-)ureido]-2-thienylmethyl-penicillin sodium.

D-α-[3-(2-butyrylamino-4-hydroxy-5-pyrimidyl)-ureido]-p-hydroxybenzyl-penicillin sodium.

D-α-[3-(2-butyrylamino-4-hydroxy-5-pyrimidyl)-ureido]-benzyl-penicillin sodium.

D-α-[3-(2-crotonylamino-4-hydroxy-5-pyrimidyl)-ureido]-p-hydroxybenzyl-penicillin sodium.

D-α-[3-(4-hydroxy-2-trifluoroacetylamino-5-pyrimidyl)-ureido]-cyclohexa-1,4-dien-1-yl-methyl-penicillin sodium.

D-α-[3-(4-hydroxy-2-trifluoroacetylamine-5-pyrimidyl)-ureido]-m,p-dihydroxybenzyl-penicillin sodium.

D-α-[3-(4-hydroxy-2-pentafluoropropionylamino-5-pyrimidyl)-ureido]-cyclohexa-1,4-dien-1-yl-methyl-penicillin sodium.

D-α-[3-(2-ethoxycarbonylamino-4-hydroxy-5-pyrimidyl)-ureido]-benzylpenicillin sodium.

D-α-[3-(2-{3'-dimethyl-ureido}-4-hydroxy-5-pyrimidyl)-ureido]-benzyl-penicillin sodium.

D-α-[3-(4-hydroxy-2-{3'-methyl-ureido}-5-pyrimidyl)-ureido[-benzyl-penicillin sodium.

D-α-[3-(4-hydroxy-2-ureido-5-pyrimidyl)-ureido]-benzyl-penicillin sodium.

D-α-[3-(2-{3'-cyclopropyl-ureido}-4-hydroxy-5-pyrimidyl)-ureido]-benzyl-penicillin sodium.

D-α-[3-(4-hydroxy-2-{3'-phenyl-ureido}-5-pyrimidyl)-ureido]-benzyl-penicillin sodium.

D-α-[3-(2-{3'-butyl-ureido}-4-hydroxy-5-pyrimidiyl)-ureido]-p-hydroxybenzyl-penicillin sodium.

D-α-[3-(2-{3'-dibutyl-ureido}-4-hydroxy-5-pyrimidyl)-ureido]p-hydroxybenzyl-penicillin sodium.

D-α-[3-(2-{3'-cyclohexyl-ureido}-4-hydroxy-5-pyrimidyl)-ureido]-p-hydroxybenzyl-penicillin sodium.

D-α-[3-(4-hydroxy-2-{3'-p-chlorophenyl-ureido}-5-pyrimidyl)-ureido]-p-hydroxybenzyl-penicillin sodium.

EXAMPLE 212

D-α-[3-(4-hydroxy-2-methylsulfonylamino-5-pyrimidyl)-ureido]-p-hydroxybenzyl-penicillin sodium This penicillin was prepared analogously to Example 189. One starts from 420 mgm amoxycillin-trihydrate (0.001 mol) and the reaction product of 255 mgm 5-amino-4-hydroxy-2-methylsulfonyl-amino-pyrimidine with 100 mgm phosgene and 0.14 ml triethylamine.

Yield: 245 mgm sodium salt (40%).

IR spectrum: 1770, 1660, 1615, 1525 $cm^{-1}$.

NMR spectrum (DMSO+$CD_3OD$) signals at ppm: 1.55 (6H), 2.9 (3H), 4.05 (1H), 5.45 (3H), 6.85 (2H), 7.35 (2H), 8.45 (1H).

EXAMPLE 213

D-α-[3-(4-hydroxy-2-methylsulfonylamino-5-pyrimidyl)-ureido]-benzyl-penicillin sodium This penicillin was prepared analogously to Example 189. One starts from 615 mgm ampicillin-sodium (0.002 mol) and the reaction product of 410 mgm 5-amino-4-hydroxy-2-methylsulfonylamino-pyrimidine (0.002 mol) with 200 mgm phosgene and 0.27 ml triethylamine.

Yield: 450 mgm sodium salt (43%).

IR spectrum: 1770, 1650, 1600, 1520 $cm^{-1}$.

NMR spectrum (DMSO+$CD_3OD$) signals at ppm: 1.55 (6H), 2.85 (3H), 4.0 (1H), 5.45 (3H), 7.5 (5H), 8.40 (1H).

EXAMPLE 214

D-α-[3-(2-ethylsulfonylamino-4-hydroxy-5-pyrimidyl)-ureido]-p-hydroxybenzyl-penicillin sodium This penicillin was prepared analogously to Example 189. One starts from 2.1 gm amoxycillin-trihydrate (0.005 mol) and the reaction product of 1.14 gm (0.005 mol) 5-amino-2-ethylsulfonylamino-4-hydroxy-pyrimidine with 500 mgm phosgene and 0.67 ml triethylamine.

Yield: 1.51 gm sodium salt (42%).

IR spectrum: 1770, 1650, 1610, 5130 $cm^{-1}$.

NMR spectrum (DMSO+$CD_3OD$) signals at ppm: 1.4 (3H), 1.55 (6H), 3.3 (2H), 4.05 (1H), 5.40 (3H), 6.8 (2H), 7.3 (2H), 8.45 (1H).

EXAMPLE 215

D-α-[3-(4-hydroxy-2-toluenesulfonylamino-5-pyrimidyl)-ureido]-p-hydroxybenzyl-penicillin sodium This penicillin was prepared analogously to Example 188. One starts from 840 mgm amoxycillin-trihydrate (0.002 mol) and the reaction product of 580 mgm (0.002 mol) 5-amino-4-hydroxy-2-toluenesulfonylamino-pyrimidine with 200 mgm phosgene and 0.27 ml triethylamine.

Yield: 820 mgm sodium salt (59%).

IR spectrum: 1770, 1650, 1600, 1550 $cm^{-1}$.

NMR spectrum (DMSO+$CD_3OD$) signals at ppm: 1.55 (6H), 2.25 (3H), 4.05 (1H), 5.45 (3H), 6.8 (2H), 7.5 (4H), 8.1 (2H), 8.45 (1H).

Analogously was prepared:

D-α-[3-(4-hydroxy-2-toluenesulfonylamino-5-pyrimidyl)-ureido]-benzyl-penicillin sodium.

The compounds of the formula I and their non-toxic, pharmacological acceptable salts have useful pharmacodynamic properties and are very compatible. They can, therefore, be used for the prophylaxis and chemotherapy of local and systemic infections in the human or veterinary medicine. The diseases which can be prevented or cured with the compounds according to the invention, include, for example, diseases of the respiratory tract, of the pharingeal cavity or of the urinary tract; the compounds are particularly effective against pharyngitis, pneumonia, peritonitis, pyelonephritis, otitis, cystitis, endocarditis, bronchitis, arthritis and general systemic infections. Furthermore, these compounds can be used as active ingredients for preserving inorganic or organic materials, especially organic materials such as polymeres, lubricants, dyes, fibres, leather, paper and wood, as well as food.

These utilities are made possible by the fact that the compounds of the formula 1 and their salts possess a very strong activity in vitro as well as in vivo against harmful microorganisms, particularly against grampositive and gramnegative bacteria and against microorganisms similar to bacteria wherefor they have an especially broad spectrum of activity. Moreover, the compounds of the formula I and their salts show after parenteral administration high levels in the tissue, serum, organis, and urine.

Surprisingly, a number of penicillins according to the present invention also show, after oral administration in the rat, high serum and tissue levels as well as high urine levels. Based on the prevailing experience with acyl derivatives of α-aminobenzyl-penicillins, this could not be expected.

In the following table typical especially effective penicillins according to the invention are listed. The indicated penicillins can be prepared according to method A or B.

The compounds of the formula I in question are those where A and R have the following meanings:

| A | R |
|---|---|
| phenyl | hydrogen |
| p-hydroxy-phenyl | hydrogen |
| cyclohexa-1,4-dien-1-yl | hydrogen |
| 2-thienyl | hydrogen |
| p-hydroxy-m-chloro-phenyl | hydrogen |
| m,p-dihydroxy-phenyl | hydrogen |
| phenyl | methyl |
| p-hydroxy-phenyl | methyl |
| cyclohexa-1,4-dien-1-yl | methyl |
| 2-thienyl | methyl |
| p-hydroxy-m-chloro-phenyl | methyl |
| m,p-dihydroxy-phenyl | methyl |
| phenyl | ethyl |
| p-hydroxy-phenyl | ethyl |
| cyclohexa-1,4-dien-1-yl | ethyl |
| phenyl | cyclopropyl |
| p-hydroxy-phenyl | cyclopropyl |
| cyclohexa-1,4-dien-1-yl | cyclopropyl |
| 2-thienyl | cyclopropyl |
| p-hydroxy-m-chloro-phenyl | cyclopropyl |
| m,p-dihydroxy-phenyl | cyclopropyl |
| phenyl | 2-methyl-cyclopropyl |
| p-hydroxy-phenyl | 2-methyl-cyclopropyl |
| cyclohexa-1,4-dien-1-yl | 2-methyl-cyclopropyl |
| phenyl | cyclopropyl-methyl |
| p-hydroxy-phenyl | cyclopropyl-methyl |
| phenyl | allyl |
| p-hydroxy-phenyl | allyl |
| cyclohexa-1,4-dien-1-yl | allyl |
| phenyl | propargyl |
| p-hydroxy-phenyl | propargyl |
| phenyl | cyclobutyl |
| p-hydroxy-phenyl | cyclobutyl |
| phenyl | benzyl |
| p-hydroxy-phenyl | benzyl |
| cyclohexa-1,4-dien-1-yl | benzyl |

-continued

| A | R |
|---|---|
| phenyl | phenyl |
| p-hydroxy-phenyl | phenyl |
| phenyl | p-chloro-benzyl |
| p-hydroxy-phenyl | p-chloro-benzyl |
| cyclohexa-1,4-dien-1-yl | p-chloro-benzyl |
| phenyl | p-fluoro-benzyl |
| p-hydroxy-phenyl | p-fluoro-hexyl |
| cyclohexa-1,4-dien-1-yl | p-fluoro-benzyl |
| phenyl | m-chloro-benzyl |
| p-hydroxy-phenyl | m-chloro-benzyl |
| cyclohexa-1,4-dien-1-yl | m-chloro-benzyl |
| phenyl | p-acetyl-benzyl |
| p-hydroxy-phenyl | p-acetyl-benzyl |
| phenyl | p-nitro-benzyl |
| p-hydroxy-phenyl | p-nitro-benzyl |
| phenyl | p-tolyl |
| p-hydroxy-phenyl | p-tolyl |
| phenyl | m-tolyl |
| p-hydroxy-phenyl | m-tolyl |
| phenyl | o,p-dichloro-benzyl |
| p-hydroxy-phenyl | o,p-dichloro-benzyl |
| cyclohexa-1,4-dien-1-yl | o,p-dichloro-benzyl |
| phenyl | p-dimethylamino-benzyl |
| p-hydroxy-phenyl | p-dimethylamino-benzyl |
| phenyl | p-chloro-phenyl |
| p-hydroxy-phenyl | p-chlorophenyl |
| phenyl | p-dimethylamino-phenyl |
| p-hydroxy-phenyl | p-dimethylamino-phenyl |
| phenyl | m,p-dichloro-benzyl |
| p-hydroxy-phenyl | m,p-dichloro-benzyl |
| phenyl | p-methyl-benzyl |
| p-hydroxy-phenyl | p-methyl-benzyl |
| phenyl | l-phenyl-ethyl |
| p-hydroxy-phenyl | l-phenyl-ethyl |
| cyclohexa-1,4-dien-1-yl | l-phenyl-ethyl |
| phenyl | hydroxy |
| p-hydroxy-phenyl | hydroxy |
| cyclohexa-1,4-dien-1-yl | hydroxy |
| 2-thienyl | hydroxy |
| p-hydroxy-m-chloro-phenyl | hydroxy |
| m,p-dihydroxy-phenyl | hydroxy |
| phenyl | methoxy |
| p-hydroxy-phenyl | methoxy |
| cyclohexa-1,4-dien-1-yl | methoxy |
| 2-thienyl | methoxy |
| phenyl | ethoxy |
| p-hydroxy-phenyl | ethoxy |
| cyclohexa-1,4-dien-1-yl | ethoxy |
| 2-thienyl | ethoxy |
| p-hydroxy-m-chloro-phenyl | ethoxy |
| phenyl | mercapto |
| p-hydroxy-phenyl | mercapto |
| phenyl | methylmercapto |
| p-hydroxy-phenyl | methylmercapto |
| phenyl | ethylmercapto |
| p-hydroxy-phenyl | ethylmercapto |
| phenyl | amino |
| p-hydroxy-phenyl | amino |
| cyclohexa-1,4-dien-1-yl | amino |
| phenyl | methylamino |
| p-hydroxy-phenyl | methylamino |
| cyclohexa-1,4-dien-1-yl | methylamino |
| 2-thienyl | methylamino |
| p-hydroxy-m-chloro-phenyl | methylamino |
| m,p-dihydroxy-phenyl | methylamino |
| phenyl | ethylamino |
| p-hydroxy-phenyl | ethylamino |
| cyclohexa-1,4-dien-1-yl | ethylamino |
| 2-thienyl | ethylamino |
| p-hydroxy-m-chloro-phenyl | ethylamino |
| m,p-dihydroxy-phenyl | ethylamino |
| phenyl | isopropylamino |
| p-hydroxy-phenyl | isopropylamino |
| cyclohexa-1,4-dien-1-yl | isopropylamino |
| phenyl | allylamino |
| p-hydroxy-phenyl | allylamino |
| cyclohexa-1,4-dien-1-yl | allylamino |
| phenyl | propargylamino |
| p-hydroxy-phenyl | propargylamino |
| phenyl | cyclopropylamino |
| p-hydroxy-phenyl | cyclopropylamino |

-continued

| A | R |
|---|---|
| cyclohexa-1,4-dien-1-yl | cyclopropylamino |
| p-hydroxy-phenyl | propylamino |
| phenyl | propylamino |
| p-hydroxy-phenyl | isobutylamino |
| phenyl | cyclopentylamino |
| p-hydroxy-phenyl | cyclopentylamino |
| cyclohexa-1,4-dien-1-yl | cyclopentylamino |
| 2-thienyl | cyclopentylamino |
| p-hydroxy-m-chloro-phenyl | cyclopentylamino |
| m,p-dihydroxy-phenyl | cyclopentylamino |
| phenyl | cyclohexylamino |
| p-hydroxy-phenyl | cyclohexylamino |
| cyclohexa-1,4-dien-1-yl | cyclohexylamino |
| 2-thienyl | cyclohexylamino |
| p-hydroxy-m-chloro-phenyl | cyclohexylamino |
| m,p-dihydroxy-phenyl | cyclohexylamino |
| phenyl | N—methyl-cyclohexylamino |
| p-hydroxy-phenyl | N—methyl-cyclohexylamino |
| phenyl | cycloheptylamino |
| p-hydroxy-phenyl | cycloheptylamino |
| phenyl | cyclopropylmethylamino |
| p-hydroxy-phenyl | cyclopropylmethylamino |
| phenyl | cyclohexylmethylamino |
| p-hydroxy-phenyl | cyclohexylmethylamino |
| phenyl | pyrrolidino |
| p-hydroxy-phenyl | pyrrolidino |
| p-hydroxy-phenyl | sec-butylamino |
| phenyl | piperidino |
| phenyl | morpholino |
| p-hydroxy-phenyl | morpholino |
| phenyl | N—formyl-piperazino |
| p-hydroxy-phenyl | N—formyl-piperazino |
| phenyl | N—acetyl-piperazino |
| p-hydroxy-phenyl | N—acetyl-piperazino |
| phenyl | piperazino |
| p-hydroxy-phenyl | piperazino |
| phenyl | N—phenyl-piperazino |
| p-hydroxy-phenyl | N—phenyl-piperazino |
| cyclohexa-1,4-dien-1-yl | N—phenyl-piperazino |
| phenyl | p-chloro-benzylamino |
| p-hydroxy-phenyl | p-chloro-benzylamino |
| cyclohexa-1,4-dien-1-yl | p-chloro-benzylamino |
| 2-thienyl | p-chloro-benzylamino |
| p-hydroxy-m-chloro-phenyl | p-chloro-benzylamino |
| m,p-dihydroxy-phenyl | p-chloro-benzylamino |
| phenyl | benzylamino |
| p-hydroxy-phenyl | benzylamino |
| p-hydroxy-m-chloro-phenyl | benzylamino |
| m,p-dihydroxy-phenyl | benzylamino |
| phenyl | N—methyl-anilino |
| p-hydroxy-phenyl | N—methyl-anilino |
| phenyl | N—methyl-p-chloro-anilino |
| p-hydroxy-phenyl | N—methyl-p-chloro-anilino |
| m,p-dihydroxy-phenyl | N—methyl-p-chloro-anilino |
| phenyl | anilino |
| p-hydroxy-phenyl | anilino |
| cyclohexa-1,4-dien-1-yl | anilino |
| phenyl | p-chloro-anilino |
| p-hydroxy-phenyl | p-chloro-anilino |
| cyclohexa-1,4-dien-1-yl | p-chloro-anilino |
| 2-thienyl | p-chloro-anilino |
| p-hydroxy-m-chloro-phenyl | p-chloro-anilino |
| m,p-dihydroxy-phenyl | p-chloro-anilino |
| phenyl | m,p-dichloro-anilino |
| p-hydroxy-phenyl | m,p-dichloro-anilino |
| cyclohexa-1,4-dien-1-yl | m,p-dichloro-anilino |
| 2-thienyl | m,p-dichloro-anilino |
| p-hydroxy-m-chloro-phenyl | m,p-dichloro-anilino |
| m,p-dihydroxy-phenyl | m,p-dichloro-anilino |
| phenyl | p-fluoro-anilino |
| p-hydroxy-phenyl | p-fluoro-anilino |
| phenyl | m-chloro-anilino |
| p-hydroxy-phenyl | m-chloro-anilino |
| cyclohexa-1,4-dien-1-yl | m-chloro-anilino |
| phenyl | p-hydroxy-anilino |
| p-hydroxy-phenyl | p-hydroxy-anilino |
| cyclohexa-1,4-dien-1-yl | p-hydroxy-anilino |
| 2-thienyl | p-hydroxy-anilino |
| phenyl | p-methyl-anilino |
| p-hydroxy-phenyl | p-methyl-anilino |
| cyclohexa-1,4-dien-1-yl | p-methyl-anilino |

-continued

| A | R |
|---|---|
| 2-thienyl | p-methyl-anilino |
| p-hydroxy-m-chloro-phenyl | p-methyl-anilino |
| m,p-dihydroxy-phenyl | p-methyl-anilino |
| phenyl | p-isopropyl-anilino |
| p-hydroxy-phenyl | p-isopropyl-anilino |
| cyclohexa-1,4-dien-1-yl | p-isopropyl-anilino |
| 2-thienyl | p-isopropyl-anilino |
| p-hydroxy-m-chloro-phenyl | p-isopropyl-anilino |
| m,p-dihydroxy-phenyl | p-isopropyl-anilino |
| phenyl | p-acetylamino-anilino |
| p-hydroxy-phenyl | p-acetylamino-anilino |
| cyclohexa-1,4-dien-1-yl | p-acetylamino-anilino |
| 2-thienyl | p-acetylamino-anilino |
| p-hydroxy-m-chloro-phenyl | p-acetylamino-anilino |
| m,p-dihydroxy-phenyl | p-acetylamino-anilino |
| phenyl | p-dimethyl-anilino |
| p-hydroxy-phenyl | p-dimethyl-anilino |
| cyclohexa-1,4-dien-1-yl | p-dimethyl-anilino |
| 2-thienyl | p-dimethyl-anilino |
| p-hydroxy-m-chloro-phenyl | p-dimethyl-anilino |
| m,p-dihydroxy-phenyl | p-dimethyl-anilino |
| phenyl | p-trifluoromethyl-anilino |
| p-hydroxy-phenyl | p-trifluoromethyl-anilino |
| cyclohexa-1,4-dien-1-yl | p-trifluoromethyl-anilino |
| 2-thienyl | p-trifluoromethyl-anilino |
| p-hydroxy-m-chloro-phenyl | p-trifluoromethyl-anilino |
| m,p-dihydroxy-phenyl | p-trifluoromethyl-anilino |
| phenyl | p-chloro-m-trifluoromethyl-anilino |
| p-hydroxy-phenyl | p-chloro-m-trifluoromethyl-anilino |
| cyclohexa-1,4-dien-1-yl | p-chloro-m-trifluormethyl-anilino |
| 2-thienyl | p-chloro-m-trifluoro-methyl-anilino |
| p-hydroxy-m-chloro-phenyl | p-chloro-m-trifluoromethyl-anilino |
| m,p-dihydroxy-phenyl | p-chloro-m-trifluoromethyl-anilino |
| phenyl | m,m-dichloro-anilino |
| p-hydroxy-phenyl | m,m-dichloro-anilino |
| phenyl | m,m-dichloro-p-amino-anilino |
| p-hydroxy-phenyl | m,m-dichloro-p-amino-anilino |
| cyclohexa-1,4-dien-1-yl | m,m-dichloro-p-amino-anilino |
| phenyl | formylamino |
| p-hydroxy-phenyl | formylamino |
| phenyl | acetylamino |
| p-hydroxy-phenyl | acetylamino |
| cyclohexa-1,4-dien-1-yl | acetylamino |
| 2-thienyl | acetylamino |
| p-hydroxy-m-chloro-phenyl | acetylamino |
| m,p-dihydroxy-phenyl | acetylamino |
| phenyl | propionylamino |
| p-hydroxy-phenyl | propionylamino |
| cyclohexa-1,4-dien-1-yl | propionylamino |
| 2-thienyl | propionylamino |
| p-hydroxy-m-chloro-phenyl | propionylamino |
| m,p-dihydroxy-phenyl | propionylamino |
| phenyl | isobutyrylamino |
| p-hydroxy-phenyl | isobutyrylamino |
| phenyl | valeroylamino |
| phenyl | cyclopropionylamino |
| p-hydroxy-phenyl | cyclopropionylamino |
| phenyl | cyclohexanoylamino |
| phenyl | trifluoroacetylamino |
| p-hydroxy-phenyl | trifluoroacetylamino |
| cyclohexa-1,4-dien-1-yl | trifluoroacetylamino |
| 2-thienyl | trifluoroacetylamino |
| p-hydroxy-m-chloro-phenyl | trifluoroacetylamino |
| m,p-dihydroxy-phenyl | trifluoroacetylamino |
| phenyl | pentafluoropropionylamino |
| p-hydroxy-phenyl | pentafluoropropionylamino |
| cyclohexa-1,4-dien-1-yl | pentafluoropropionylamino |
| 2-thienyl | pentafluoropropionylamino |
| p-hydroxy-m-chloro-phenyl | pentafluoropropionylamino |
| m,p-dihydroxy-phenyl | pentafluoropropionylamino |
| phenyl | heptafluorobutyrylamino |
| p-hydroxy-phenyl | heptafluorobutyrylamino |
| cyclohexa-1,4-dien-1-yl | heptafluorobutyrylamino |
| 2-thienyl | heptafluorobutyrylamino |
| p-hydroxy-m-chloro-phenyl | heptafluorobutyrylamino |
| m,p-dihydroxy-phenyl | heptafluorobutyrylamino |
| phenyl | ethoxycarbonylamino |
| phenyl | ureido |
| p-hydroxy-phenyl | ureido |
| cyclohexa-1,4-dien-1-yl | ureido |
| 2-thienyl | ureido |

-continued

| A | R |
|---|---|
| phenyl | 3-methyl-ureido |
| p-hydroxy-phenyl | 3-methyl-ureido |
| cyclohexa-1,4-dien-1-yl | 3-methyl-ureido |
| 2-thienyl | 3-methyl-ureido |
| p-hydroxy-m-chloro-phenyl | 3-methyl-ureido |
| m,p-dihydroxy-phenyl | 3-methyl-ureido |
| phenyl | 3-dimethyl-ureido |
| p-hydroxy-phenyl | 3-dimethyl-ureido |
| cyclohexa-1,4-dien-1-yl | 3-dimethyl-ureido |
| 2-thienyl | 3-dimethyl-ureido |
| phenyl | 3-cyclopropyl-ureido |
| phenyl | pyrrolidinocarbonyl-amino |
| p-hydroxy-phenyl | pyrrolidinocarbonyl-amino |
| p-hydroxy-m-chloro-phenyl | pyrrolidinocarbonyl-amino |
| m,p-dihydroxy-phenyl | pyrrolidinocarbonyl-amino |
| phenyl | 3-phenyl-ureido |
| p-hydroxy-phenyl | 3-phenyl-ureido |

With these penicillin derivatives, for example, local and/or systemic diseases can be treated and/or prevented, which are caused by the following pathogens or mixtures thereof:

Micrococcaceae, such as staphylococci;
Lactobacteriaceae, such as streptococci;
Neisseriaceae, such as neisseria;
Cornynebacteriaceae, such as cornynebacteria;
Enterobacteriaceae, such as escherichiae-bacteria of the coli group;
Klebsiella bacteria, e.g. K. pneumonia;
Proteae bacteria of the proteus group; e.g. proteus vulgaris;
Salmonella bacteria, e.g. s. thyphimurium;
Shigella bacteria, e.g. shigella dysenteriae;
Pseudomonas bacteria, e.g. pseudomonas aeruginosa;
Aeromonas bacteria, e.g. aeromonas lique faciens.
Spirillaceae, such as vibrio bacteria, e.g. vibrio cholerae;
Parvobacteriaceae or brucellaceae, such as pasteurella bacteria;
Brucella bacteria; e.g. brucella abortus;
Haemophilus bacteria, e.g. haemophilus influencae;
Bordetella pertussis;
Moraxella bacteria, e.g. moraxella lacunata;
Bacteriodaceae, such as bacteroides bacteria;
Fusiforme bacteria, e.g. fusobacterium fusiforme;
Sphaerophorus bacteria, e.g. sphaerophorus necrophorus;
Bacillaceae, such as aerobe spore formers, e.g. bacillus anthracis;
Anaerobe spore former chlostridia, e.g. chlostridium perfringens;
Spirochaetaceae, such as borrelia bacteria;
Treponema bacteria, e.g. treponema palidum;
Leptospira bacteria, such as leptospira interrogans.

The above list of pathogens is merely illustrative and should not in any way be considered restrictive.

The effectiveness of the penicillins of the present invention can be demonstrated by the following tests:

1. In vitro tests:

The tests were performed according to the method of the serial dilution test in the microtiter system. The effect of the substances on bacteriostasis was examined in a fluid medium. The activity on bacteriostatis was examined at the following concentrations:

80; 40; 20; 10; 5; 2.5; 1.25; 0.6; 0.3; 0.08 and 0.02 μg/ml. A nutrient medium of the following composition was used:

10 gm of peptone, 8 gm of meat extract-oxoid, 3 gm of sodium chloride, 2 gm of sec. sodium phosphate were diluted with distilled water to 1000 ml (pH 7.2-7.4). Only in the test against streptococci 1% of glucose was added. The age of the primary cultures was about 20 hours. The standardizations of the pathogen suspension was effected by using a photometer according to "Eppendorf" (test tube diameter 14 mm, filter 546 nm) with the aid of the turbidity of a comparison suspension consisting of barium sulfate, this suspension being prepared by addition of 3.0 ml of 1% barium chloride solution to 97 ml of 1% sulfuric acid. After the standardization, streptococcus aronson were further diluted to a concentration of 1:15 and the other germs to a concentration of 1:1500 by means of a sodium chloride solution.

16 mg of the test substance were put into a 10 ml measuring flask and filled up to the mark with the solvent. The further dilution series was standardized with distilled water or the respective solvent.

The cavities of the microtiter plates were filled with 0.2 ml of nutrient medium. Then, 0.01 ml of the corresponding test substance dilution was added and inoculated with 0.01 ml of the standardized suspension. The bacteria were incubated at 37° C. for 18-20 hours. Control tests merely using the solvent were carried out simultaneously.

The measurement was carried out macroscopically to determine the minimal inhibitory (threshold) concentration, i.e. the lowest still bacteriostatically effective concentration.

The following test organisms were used:

Staphylococcus aureus SG 511, streptococcus aronson, streptococcus faecalis ATCC 10541, escherichia coli ATCC 9637, 11 775 and escherichia coli 12593/74 (β-lactamase carrier), pseudomonas aeruginosa hamburgensis and ATCC 10145, serratia marcescens ATCC 13 880, klebsiella pneumoniae ATCC 10 031 and 272 and proteus mirabilis hamburgensis.

The following table I shows the minimal inhibitory concentrations (MIC) for typical representatives of the compounds according to the invention:

Sodium salt of compounds of the formula I with the meanings of A and R:

| A | R | |
|---|---|---|
| p-hydroxyphenyl | hydrogen | = A |
| p-hydroxyphenyl | methyl | = B |
| p-hydroxyphenyl | cyclopropyl | = C |
| p-hydroxyphenyl | p-chlorobenzyl | = D |
| p-hydroxyphenyl | acetylamino | = E |
| p-hydroxyphenyl | heptafluoro-propionylamino | = F |
| p-hydroxyphenyl | anilino | = G |
| p-hydroxy-phenyl | p-chloroanilino | = H |
| p-hydroxyphenyl | m,p-dichloroanilino | = J |
| p-hydroxyphenyl | morpholino | = K |
| p-hydroxyphenyl | cyclohexylamino | = L |
| p-hydroxyphenyl | 3-dimethylureido | = M |
| p-hydroxyphenyl | methylamino | = N |
| p-hydroxyphenyl | p-chlorobenzylamino | = O |
| p-hydroxyphenyl | propylamino | = P |

Penicillins of the formula XV

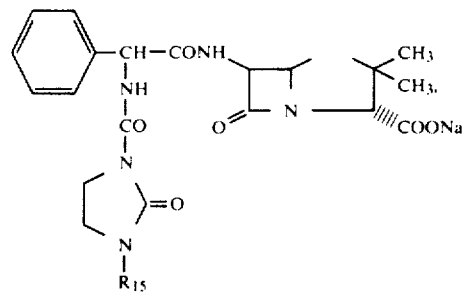

(XV)

where (XVa) $R_{15}$ = H(azlocillin) = Q
(XVb) $R_{15}$ = $SO_2CH_3$(mezlocillin) = R and D-α-[(4-hydroxy-3-pyridyl)-ureido]benzylpenicillin sodium (see German Offenlegungsschrift No. 2,450,668) = S were used as comparative compounds.

TABLE I

| | MIC-values of various penicillins (in μg/ml) | | | | | | | | | | | |
|---|---|---|---|---|---|---|---|---|---|---|---|---|
| | *Staph. Aureus* SG 511 | *strept aronson* | *strept. faecal.* | *E. coli* ATCC 9637 | *E. coli* ATCC 11775 | *E. coli* 12593/ 74 | *pseud. aerug.* hamb. | *pseud. aerug.* ATCC 10145 | *serrat marcesc.* | *klebs pneum* ATCC 10031 | *klebs pneum.* 272 | *prot. mirabilis* |
| Compound | | | | | | | | | | | | |
| A | 0.3 | 0.08 | 10 | 2.5 | 2.5 | >80 | 5 | 2.5 | 5 | 80 | 80 | 0.6 |
| B | 1.25 | 0.3 | 10 | 2.5 | 1.25 | 80 | 5 | 2.5 | 5 | 80 | 80 | 0.6 |
| C | 0.3 | 0.08 | 10 | 2.5 | 1.25 | 80 | 2.5 | 1.25 | 1.25 | 40 | 80 | 1.25 |
| D | 0.08 | 0.02 | 10 | 2.5 | 1.25 | 80 | 5 | 2.5 | 1.25 | 5 | 10 | 1.25 |
| E | 1.25 | 0.3 | 10 | 5 | 2.5 | >80 | 2.5 | 2.5 | 10 | 80 | 80 | 1.25 |
| F | 1.25 | 0.3 | 10 | 2.5 | 2.5 | >80 | 2.5 | 2.5 | 2.5 | 80 | 80 | 0.6 |
| G | 0.3 | 0.08 | 5 | 0.6 | 1.25 | >80 | 5 | 2.5 | 0.3 | 10 | 5 | 2.5 |
| H | 1.25 | 0.08 | 5 | 1.25 | 0.6 | 80 | 2.5 | 1.25 | 1.25 | 5 | 2.5 | 0.6 |
| J | 0.03 | 0.02 | 2.5 | 1.25 | 0.6 | 10 | 2.5 | 2.5 | 0.6 | 2.5 | 2.5 | 0.6 |
| K | 1.25 | 0.3 | 10 | 2.5 | 2.5 | >80 | 2.5 | 1.25 | 5 | >80 | 80 | 1.25 |
| L | 0.3 | 0.08 | 5 | 0.6 | 1.25 | >80 | 2.5 | 2.5 | 1.25 | 20 | 10 | 0.6 |
| M | 1.25 | 0.3 | 80 | 10 | 2.5 | >80 | 5 | 5 | 10 | >80 | >80 | 2.5 |
| N | 0.3 | 0.08 | 10 | 2.5 | 2.5 | >80 | 2.5 | 2.5 | 5 | 80 | 40 | 0.3 |
| O | 0.3 | 0.02 | 10 | 0.3 | 0.65 | 80 | 10 | 5 | 1.25 | 20 | 10 | 0.3 |
| P | 0.3 | 0.08 | 5 | 1.25 | 1.25 | 80 | 2.5 | 1.25 | 1.25 | 10 | 10 | 0.08 |
| Comparison Compounds | | | | | | | | | | | | |
| Q | | | | 20 | 10 | | 10 | 5 | | | | |
| R | | | | 10 | 5 | | 40 | 20 | | | | |
| S | | | | 10 | 2.5 | | 20 | 20 | | | | |

The above table shows that the compounds of the invention are significantly superior to the comparison compounds in their activity against typical germs in hospitals such as E. coli ATCC 11775 and E. coli 9637, pseudomonas aerug. hamburg. and ATCC 10145.

For the penicillins C and H, which are typical representatives for this invention, the influence of the size of the inoculum on the MIC-values against ps. aerug. hamburg. and E. coli ATCC 11775 in the microtiter system was determined. Thereby 3 different sizes of inoculum ($3.3\times10^6$, $3.3\times10^4$ and $3.3\times10^2$ in E. coli and $4.7\times10^6$, $4.7\times10^4$ and $4.7\times10^2$ in pseudomonas) were used. The reference system was again penicillin Q.

TABLE II

Influence of the size of the inoculum on the MIC-values against *pseud. cerug.* hamburg.

| | $4.7\times10^6$ germs/ml | $4.7\times10^4$ germs/ml | $4.7\times10^2$ germs/ml |
|---|---|---|---|
| C | >80 | 5 | 2.5 |
| H | >80 | 2.5 | 2.5 |
| Q | >80 | 10 | 5 |

TABLE III

Influence of the size of the inoculum on the MIC-values against *E. coli* ATCC 11775

| | $3.3\times10^6$ germs/ml | $3.3\times10^4$ germs/ml | $3.3\times10^2$ germs/ml |
|---|---|---|---|
| C | 2.5 | 2.5 | 2.5 |
| H | 1.0 | 0.6 | 0.3 |
| Q | 10 | 10 | 10 |

The acute toxicity was determined by peroral and subcutaneous administration of the compounds of table I to white mice.

The $LD_{50}$ is the dose which leads to the death of 50% of the animals within 8 days. All substances showed after oral adminstration an $LD_{50}$ of more than 4 g/kg, after subcutaneous administration an $LD_{50}$ of more than 3 g/kg, i.e., at 3 g/kg no animal died. This means that the substances are for practical purposes completely non-toxic.

For the determination of the serum level in rats, typical representatives of the penicillins according to the invention were administered at a dosage of 10 mg/kg subcutaneously or 100 mg/kg per os to groups of 3 female FW 49 rats (weight 100 to 130 gm) each. Blood tests taken from the heart were worked up, and the obtained sera were tested by the cylinder test-agar diffusion method on plates with sarcina lutea ATCC 15957. The samples were compared with standard curves.

The obtained results are shown in the following table:

TABLE IV

Blood level in rats (μg/ml) after administration of a single dose of each substance (average from 3 rats)

Dose: oral 100 mg/kg
subcutaneous 10 mg/kg.

| Time | Compound A | B | C | D | E | G | Q |
|---|---|---|---|---|---|---|---|
| Subcutaneous administration: | | | | | | | |
| 30 min. | 9.3 | — | 5.1 | — | 4.1 | — | 2.8 |
| 60 min. | 8.6 | 7.3 | 6.8 | 7.1 | 5.8 | 5.6 | 3.7 |
| 120 min. | 0.4 | 1.1 | 0.4 | 0.3 | 7.7 | 1.5 | 0.4 |
| Oral administration: | | | | | | | |
| 30 min. | 9.1 | — | 3.3 | — | 13.8 | — | 0.8 |

TABLE IV-continued

| Blood level in rats (μg/ml) after administration of a single dose of each substance (average from 3 rats) | | | | | | | |
|---|---|---|---|---|---|---|---|
| Dose: oral 100 mg/kg subcutaneous 10 mg/kg. | | | | | | | |
| | Compound | | | | | | |
| Time | A | B | C | D | E | G | Q |
| 60 min. | 9.6 | 18.8 | 4.8 | 4.1 | 13.9 | 0.6 | 0.6 |
| 120 min. | 2.9 | 1.9 | 1.0 | 1.0 | 13.7 | 0.1 | 0.3 |

A number of compounds of this invention were tested in vivo in mice against experimental infections. Bacteria E. coli ATCC 11775 and pseudomonas aeruginosa walter were used as pathogens. An intraperitoneal infection with 0.2 ml of a 5% mucin suspension of the bacteria was induced. This corresponds to about $2\times10^6$ germs E. coli and $8\times10^5$ germs pseudomonas/mouse. Female NMRI mice were divided into groups of 10 animals each, two control groups remained untreated, the remaining groups were treated with different doses of the respective penicillins for the determination of the $ED_{50}$ (dose at which 50% of the animals survived). The groups with the E. coli infection were treated with the substance 3 times on the first day (1, 4 and 7 hours post-infectionem) and for 2 days thereafter twice a day. The groups with the pseudomonas infection were treated with the substance applied 6 times on the first day (1, 3, 6, 9, 12, and 15 hours post-infectionem) and for 2 days thereafter twice a day. The observation time was in both cases 7 days. The results of these tests with representatives of the penicillins according to the invention are shown in the following table:

TABLE V

| In vivo activity in mice: | | |
|---|---|---|
| | Compound | $ED_{50}$(mg/kg) |
| (a)*e. coli* infection: | A | 6 (subcutaneous) |
| | | 50 (peroral) |
| | B | 5 (subcutaneous) |
| | C | 1.5 (subcutaneous) |
| | | 30 (Peroral) |
| | D | 9 (subcutaneous) |
| | E | 15 (subcutaneous) |
| | G | 8 (subcutaneous) |
| | Q | 35 (subcutaneous) |
| | | 320 (peroral) |
| (b) Pseudomonas: | A | 50 (subcutaneous) |
| | C | 7 (subcutaneous) |
| | Q | 110 (subcutaneous) |

The tabulated values show that the representative species of the penicillins according to the present invention are useful antibiotics, based on their broad antibiotic spectrum, their high antibacterial activity, their low toxicity and their high serum levels after subcutaneous and oral administration.

The further object of the present invention is to provide pharmaceutical compositions for the treatment of infectious diseases in humans as well as in animals.

Preferred pharmaceutical compositions are tablets, coated pills, capsules, granulates, suppositories, solutions, suspensions, emulsions, ointments, gels, cremes, powders and sprays. In human or veterinary medicine it is of advantage to apply the active ingredient or a mixture of different active ingredients of the general formula I at a dosage between 5 and 500, preferably between 10 and 200 mg/kg body weight every 24 hours, optionally in form of several single application. A single administration contains the active ingredient or ingredients according to the invention, preferably in amounts of about 1 to about 100, especially 5 to 60 mg/kg body weight. However, it may be necessary to deviate from the mentioned dosages. The deviation depends upon the kind and the body weight of the subject to be treated, on the kind and severity of the disease, on the kind of composition and method of administration of the drug, as well as on the period or interval within which the administration is effected. Thus, it may be sufficient in some cases to take less than the above-mentioned amount of active ingredient, while in other cases the above-mentioned amount of active ingredient must be exceeded. The optimum dosage and method of administration of the active ingredients which are required in any particular case can easily be determined by those skilled in the art based on their special knowledge.

If the active ingredient is parenterally applied, it is preferred to dissolve the penicillin compound according to the invention in a non-toxic liquid medium for injection purposes and to inject the solution intramusculary, intravenously, or subcutaneously.

It is further possible to dissolve the penicillin compound in a non-toxic liquid medium or in an ointment or to mix it therewith, and to apply the solution or the mixture directly to the affected area. The compounds can also be used as suppositories after mixing them with a suppository base or after dissolving them therein.

Examples of non-toxic liquid media which can be used for the preparation of injectable compositions containing the penicillin compound as an active ingredient are sterilized de-ionized water, physiological sodium chloride solution, glucose solution for injection, Ringer's solution and amino acid solution for injection.

The penicillin compound can also be dissolved in other injectable compositions and can be administered parenterally.

For oral administration the penicillin compounds according to the invention are used in the form of a pharmaceutical preparation containing the compound(s), optionally admixed with the pharmaceutically compatible carriers such as an organic or inorganic solid or liquid excipient, which is suitable for oral administration. If desired, these compositions can also contain other excipients, stabilizing agents and other conventional additives.

If the penicillin compounds are used as animal feed additives, they can be administered at the usual concentrations and together with the feed or with feed compositions or with drinking water. In this manner, an infection by gramnegative or grampositive bacteria can be prevented, ameliorated and/or cured, and also a growth promotion and an improvement of the utilization of the feed can be achieved.

The penicillins according to the invention can, for the purpose of broadening the activity spectrum and in order to increase the activity especially in β-lactamase-forming bacteria, be combined with other antimicrobial active ingredients such as with penicillinase-solid penicillins. For this purpose, especially oxacillin or dicloxacillan are suitable. Moreover, the penicillins can be combined with β-lactamase inhibitors such as clavulanic acid.

The penicillins can also be combined with aminoglycoside antibiotics such as gentamicin, sisomicin, canamicin, amicacin or tobramicin, in order to broaden the spectrum of effectiveness and to achieve an increase in activity.

This invention relates, therefore, also to pharmaceutical compositions containing at least one penicillin derivative of the formula I or a pharmaceutically acceptable salt thereof and an amino-glycoside antibiotic or a pharmaceutically compatible acid addition salt thereof, optoinally admixed with a pharmaceutically compatible carrier or diluting agent.

The following examples illustrate a few pharmaceutical dosage unit compositions comprising a compound of the present invention as an active ingredient and represent the best modes contemplated of putting the invention into practical use. The parts are parts by weight unless otherwise specified.

EXAMPLE 216

Tablets

The tablet composition is compounded from the following ingredients:

| | |
|---|---|
| D-α-[3-(2-Cyclopropyl-4-hydroxy-5-pyrimidyl)-ureido]-p-hydroxy-benzyl-penicillin sodium salt | 2.0 parts |
| Lactose | 5.0 parts |
| Potato starch | 1.8 parts |
| Magnesium stearate | 0.1 parts |
| Talcum | 0.1 parts |
| Total | 9.0 parts |

Preparation

The ingredients are intimately admixed with each other, and the mixture is compressed into 900 mgm-tablets. Each tablet is an oral dosage unit composition containing 200 mgm of the active ingredient.

EXAMPLE 217

Coated Pills

The composition of Example 216 is compressed into 900 mgm-pill cores which are subsequently coated with a thin shell consisting essentially of a mixture of sugar, potato starch, talcum and tragacanth. Each coated pill is an oral dosage unit composition containing 200 mgm of the active ingredient.

EXAMPLE 218

Gelatine Capsules 500 mgm-portions of finely milled D-α-[3-(2-cyclopropyl-4-hydroxy-5-pyrimidyl)-ureido]-p-hydroxy-benzyl-penicillin sodium salt are filled into hard gelatin capsules of suitable size. Each filled capsule is an oral dosage unit composition.

EXAMPLE 219

Dry ampules 251 gm of D-α-[3-(2-cyclopropyl-4-hydroxy-5-pyrimidyl)-ureido]-p-hydroxy-benzyl-penicillin sodium salt are dissolved under aseptic conditions in 2,008 ml of distilled water suitable for injection, and the solution if filtered through a millipore-filter (pore size 0.22 mm). 2.0 ml-portions of the filtrate are filled into 10-ml-glass ampules, the contents are freeze-dried, and the ampules are then closed with a rubber stopper and an aluminum cap. Each ampules (A) contains 250 mgm of active ingredient.

2.0 ml-portions of a physiological sodium chloride solution suitable for injection are filled into 2 cc-ampules which are then sealed (ampules B).

The contents of an ampule B are poured into and thoroughly admixed with an ampule A, whereby an injectable dosage unit composition for intravenous administration is obtained.

20 ml of distilled water suitable for injection are added to the contents of an ampule A, and the resulting solution is dissolved in 250 ml of an aqueous 5% solution of glucose suitable for injection. A solution suitable for continuous intravenous infusion is obtained.

Any one of the other compounds embraced by formula I or a non-toxic, pharmacologically acceptable salt thereof may be substituted for the particular active ingredient in Examples 216 through 219. Likewise, the amount of active ingredient in these illustrative examples may be varied to achieve the dosage unit ranges set forth above, and the amounts and nature of the inert pharmaceutical carrier ingredients may be varied to meet particular requirements.

While the present invention has been illustrated with the aid of certain specific embodiments thereof, it will be readily apparent to others skilled in the art that the invention is not limited to these particular embodiments, and that various changes and modifications may be made without departing from the spirit of the invention or the scope of the appended claims.

We claim:

1. A compound of the tautomeric formulas

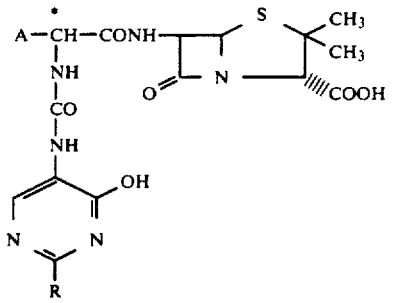

and

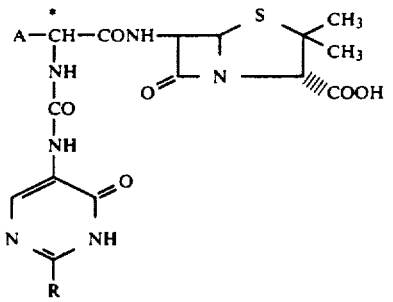

wherein A is phenyl; 4-hydroxyphenyl; 2-thienyl; 3-thienyl; cyclohexyl; cyclohexen-1-yl; cyclohexa-1,4-dien-1-yl; phenyl disubstituted in 3,4-position, where the substituents are each chlorine, hydroxyl or methoxy;

R is hydrogen; aliphatic hydrocarbyl of 1 to 8 carbon atoms optionally containing one to two double bonds or a triple bond; cyclopropyl, which may optionally be substituted with one to two methyl groups, an ethyl group or a phenyl group; cycloalkyl of 4 to 8 carbon atoms optionally containing one or more double bonds;

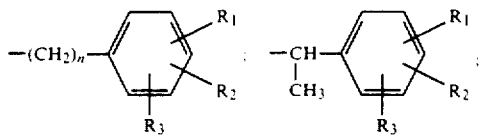

β-phenylethyl; γ-phenyl-propyl; β-phenylethylidine; cyclopropyl-methyl; 1-cyclopropylethyl; hydroxyl; alkoxy of 1 to 8 carbon atoms; alkenyloxy of 1 to 8 carbon atoms; cycloalkoxy of 3 to 6 carbon atoms; phenoxy; benzyloxy; mercapto; alkylmercapto of 1 to 8 carbon atoms; cycloalkylmercapto of 3 to 6 carbon atoms; phenylmercapto; benzylmercapto; p-chloro-benzylmercapto; alkylsulfinyl of 1 to 4 carbon atoms;

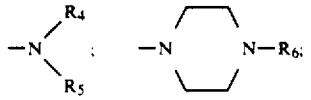

morpholino; thiomorpholino; thiomorpholino-S-oxide; thiomorpholino-S,S-dioxide;

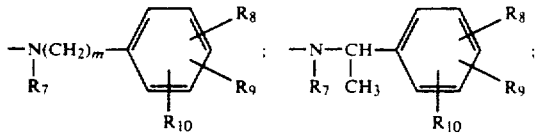

$NH-\underset{\underset{O}{\|}}{C}-R_{11}$ [or]; *or* $NHSO_2R_{14}$;

n is 0 or 1;

$R_1$, $R_2$ and $R_3$ are each hydrogen; halogen; amino; alkylamino; dialkylamino of 1 to 4 carbon atoms; hydroxy; alkoxy of 1 to 4 carbon atoms; nitro; formylamino; aliphatic acylamino of 1 to 4 carbon atoms in the alkyl moiety; alkylsulfonylamino of 1 to 4 carbon atoms; alkylcarbonyl of 1 to 4 carbon atoms in the alkyl moiety; alkylcarbonyloxy of 1 to 4 carbon atoms in the alkyl moiety; alkoxycarbonyl of 1 to 4 carbon atoms in the alkyl moiety; aminocarbonyl, optionally substituted by one to two alkyl groups of 1 to 3 carbon atoms; cyano; alkylmercapto of 1 to 4 carbon atoms; alkylsulfoxy of 1 to 4 carbon atoms; alkylsulfonyl of 1 to 4 carbon atoms; aminosulfonyl; alkylaminosulfonyl of 1 to 4 carbon atoms; dialkylaminosulfonyl of 1 to 4 carbon atoms in the alkyl moiety; trifluoromethylsulfonyl; alkyl of 1 to 4 carbon atoms; trifluoromethyl; or phenyl;

$R_4$ and $R_5$ are each hydrogen; aliphatic hydrocarbyl of 1 to 8 carbon atoms optionally containing one to two double bonds or a triple bond; cycloalkyl of 3 to 8 carbon atoms which may be substituted with one to two methyl or ethyl groups and may contain one or more double bonds; or cycloalkyl-substituted alkyl of 3 to 8 carbon atoms in the cycloalkyl moiety and 1 to 3 carbon atoms in the alkyl moiety;

$R_4$ and $R_5$ together can also form an alkylene chain of 2 to 7 carbon atoms, so that a 3- to 8-membered heterocyclic ring is formed, which may optionally be substituted with one to two alkyl groups of 1 to 3 carbon atoms or a benzyl group, or may contain one to two double bonds or may be fused with a phenyl ring;

$R_6$ is hydrogen; formyl; acetyl; ethoxycarbonyl; benzyloxycarbonyl; methyl; ethyl; phenyl; or benzyl;

$R_7$ is hydrogen[,]; methyl; or ethyl;

m is 0, 1 or 2;

$R_8$, $R_9$ and $R_{10}$ are each hydrogen; halogen; amino; alkylamino of 1 to 6 carbon atoms; dialkylamino, where each alkyl moiety contains 1 to 6 carbon atoms; pyrrolidyl; piperidyl; hydroxyl; alkoxy of 1 to 6 carbon atoms; formylamino; formylalkylamino of 1 to 3 carbon atoms in the alkyl moiety; aliphatic acylamino of 1 to 3 carbon atoms; acylalkylamino of 1 to 4 carbon atoms in the alkyl moiety and 1 to 3 carbon atoms in the acyl moiety; trifluoroacetylamino; aminocarbonylamino; alkylaminocarbonylamino of 1 to 6 carbon atoms in the alkyl moiety; dialkylaminocarbonylamino of 1 to 6 carbon atoms in each alkyl moiety; nitro; alkylsulfonylamino of 1 to 4 carbon atoms in the alkyl moiety; alkylsulfonylalkylamino of 1 to 4 carbon atoms in each alkyl moiety; hydroxysulfonylamino; hydroxysulfonylalkylamino of 1 to 3 carbon atoms in the alkyl moiety; amidino; guanidino[,]; formyl[,]; alkylcarbonyl of 1 to 6 carbon atoms; benzoyl; alkylcarbonyloxy; alkoxycarbonyl or alkoxycarbonyloxy [groups] of 1 to 6 carbon atoms; formyloxy; carboxyl; aminocarbonyl; alkylaminocarbonyl of 1 to 4 carbon atoms in the alkyl moiety; dialkylaminocarbonyl of 1 to 4 carbon atoms in each alkyl moiety; aminocarboxyl; alkylaminocarboxyl of 1 to 4 carbon atoms in the alkyl moiety; dialkylaminocarboxyl of 1 to 4 carbon atoms in each alkyl moiety; alkoxycarbonylamino of 1 to 4 carbon atoms in the alkoxy moiety; alkoxycarbonylalkylamino of 1 to 4 carbon atoms in each alkyl moiety; cyano; mercapto, alkylmercapto of 1 to 6 carbon atoms; trifluoromethylmercapto; alkylsulfoxy of 1 to 6 carbon atoms; alkylsulfonyl of 1 to 6 carbon atoms; trifluoromethylsulfonyl; aminosulfonyl; alkylaminosulfonyl of 1 to 4 carbon atoms; dialkylaminosulfonyl of 1 to 4 carbon atoms; hydroxysulfonyl [of 1 to 4 carbon atoms]; alkoxysulfonyl of 1 to 4 carbon atoms; aminosulfonyloxy[,]; alkylaminosulfonyloxy of 1 to 4 carbon atoms[,]; dialkylaminosulfonyloxy [groups] of 1 to 4 carbon atoms in each alkyl moiety; straight or branched alkyl of 1 to 6 carbon atoms, which may contain double bonds or may *further* be halo-substituted; azido; dialkylmethyleneimino of 2 to 6 carbon atoms in the alkyl moieties; dialkylaminomethylideneimino groups of 2 to 6 carbon atoms in the alkyl moieties; or phenyl;

$R_{11}$ is hydrogen[,]; alkyl of 1 to 8 carbon atoms; alkenyl of 1 to 8 carbon atoms; cycloalkyl of 3 to 6 carbon atoms; phenyl; benzyl;

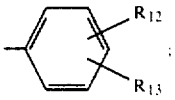

$C_xF_{2x+1}$, where x is 1, 2, 3, or 4; alkoxy of 1 to 4 carbon atoms; benzyloxy[,]; cycloalkyloxy of 3 to 6 carbon atoms; amino[,]; alkylamino of 1 to 8 carbon atoms; dialkylamino of 1 to 8 carbon atoms in each alkyl moiety; cycloalkylamino of 3 to 6 carbon atoms; cycloalkyleneamino of 3 to 6 carbon atoms; [or]

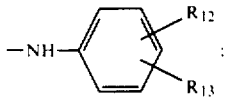

*or benzylamino;*

$R_{12}$ and $R_{13}$ are each hydrogen; chlorine [,]; methoxy; *or* methyl; [or benzylamino;] and $R_{14}$ is alkyl of 1 to 6 carbon atoms; cycloalkyl of 3 to 6 carbon atoms; benzyl; phenyl, optionally substituted with one to three methyl groups; amino; alkylamino of 1 to 6 carbon atoms; or dialkylamino of 1 to 6 carbon [atons] *atoms* in each alkyl moiety; or a non-toxic, pharmacologically acceptable salt thereof.

2. A compound of claim 1, where

A is phenyl [,]; p-hydroxyphenyl; 2- or 3-thienyl; 3-chloro-4-hydroxyphenyl; 3,4-dihydroxy-phenyl; or 1,4-cyclohexadien-1-yl;

R is hydrogen; aliphatic hydrocarbyl of 1 to 4 carbon atoms, which may contain a double or a triple bond; cyclopropyl, which may be substituted by methyl or ethyl; cycloalkyl of 4 to 6 carbon atoms, which may contain a double bond;

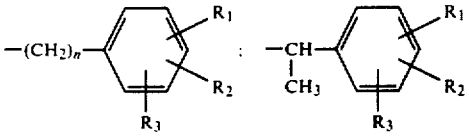

cyclopropylmethyl; 1-cyclopropylethyl; hydroxyl; alkoxy of 1 to 4 carbon atoms;

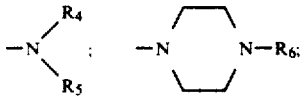

morpholino; thiomorpholino; thiomorpholino-S-oxide; thiomorpholino-S,S-dioxide;

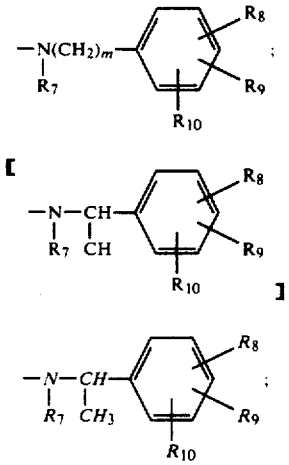

$NHCOR_{11}$; alkylsulfonylamino of 1 to 3 carbon atoms in the alkyl moiety [,]; toluenesulfonylamino; aminosulfonylamino; alkylaminosulfonylamino of 1 to 4 carbon atoms; or dialkylaminosulfonylamino of 1 to 4 carbon atoms in each alkyl moiety;

n, $R_1$, $R_2$, $R_3$, $R_4$, $R_5$, $R_6$, $R_7$, $R_8$, $R_9$, $R_{10}$ and m have the same meanings as in claim [6] *1*;

$R_{11}$ is hydrogen; alkyl of 1 to 4 carbon atoms; cycloalkyl [pf] *of* 3 to 6 carbon atoms; phenyl; chloro-substituted phenyl; $C_xF_{2x+1}$, where [X] *x* is 1, 2, 3 or 4; alkoxy of 1 to 4 carbon atoms; amino; alkylamino of 1 to 4 carbon atoms; dialkylamino of 1 to 4 carbon atoms in each alkyl moiety; cyclopropylamino; cycloalkyleneamino of 4 to 5 carbon atoms; or

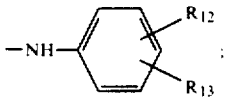

and $R_{12}$ and $R_{13}$ have the meanings defined in claim 1, *or a non-toxic, pharmacologically acceptable salt thereof.*

3. A compound of claim 1 where

A is phenyl, p-hydroxyphenyl or 1,4-cyclohexadien-1-yl;

R is hydrogen; methyl; ethyl; isopropyl; vinyl; allyl; propargyl; crotyl; cyclopropyl; 1-methyl-cyclopropyl-(1); 2-methylcyclopropyl-(1); cyclobutyl;

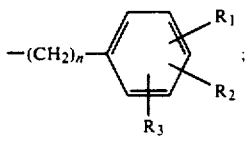

1-phenyl-ethyl; cyclopropylmethyl; hydroxyl; methoxy; ethoxy;

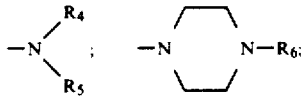

morpholino;

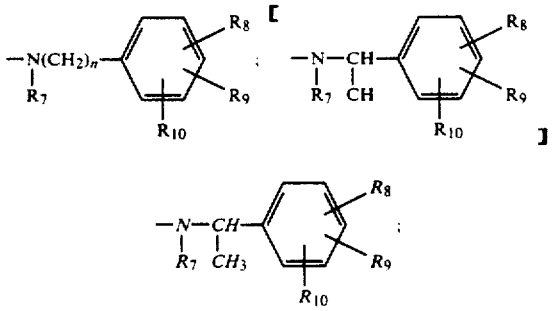

$-NHCOR_{11}$; methylsulfonyl-amino; ethylsulfonylamino; or toluenesulfonylamino;

n is 0 or 1;

one to two of $R_1$, $R_2$, and $R_3$ are chlorine, fluorine, methyl, ethyl, methoxy, ethoxy, methylamino, dimethylamino, acetylamino, methylsulfonylamino, acetyl, methoxycarbonyl, methylaminocarbonyl, dimethylaminocarbonyl, methylmercapto, methylsulfoxy, methylsulfonyl; methylcarbonyloxy; nitro, cyano, trifluoromethyl or hydroxyl, and the [remainer] *remainder* of $R_1$, $R_2$ and $R_3$ are hydrogen;

$R_4$ and $R_5$ have the meanings defined in claim [6] *1*;

$R_6$ is phenyl, formyl or acetyl;

$R_7$ is hydrogen or methyl;

m is 0, 1 or 2;

one to two of $R_8$, $R_9$, *and* $R_{10}$ are bromine, chlorine, fluorine, methyl, ethyl, isopropyl, amino, methylamino, dimethylamino, hydroxy, methoxy, ethoxy, nitro, acetylamino, methylsulfonyl, amidino, guanidino, acetyl, methylcarbonyloxy, methoxycarbonyl, carboxyl, aminocarbonyl, methyl and dimethylaminocarbonyl, cyano, methylmercapto, methylsulfoxy, methylsulfonyl, aminosulfonyl or [trilfluoromethyl] *trifluoromethyl* groups, and the remainder of $R_8$, $R_9$ and $R_{10}$ are hydrogen; and $R_{11}$ is hydrogen; alkyl of 1 to 4 carbon atoms; cycloalkyl of 3 to 6 carbon atoms; trifluoroacetyl, pentafluoroethyl; heptafluoropropyl; ethoxy; amino; alkylamino of 1 to 4 carbon atoms; dialkylamino of 1 to 4 carbon atoms in each alkyl moiety; cyclopropylamino; pyrrolidino; piperidino; phenylamino; or p-chlorophenylamino, *or a non-toxic, pharmacologically acceptable salt thereof.*

4. An antibiotic pharmaceutical dosage unit composition consisting essentially of an inert pharmaceutical carrier and an effective antibiotic amount of a compound of claim 1.

5. The method of inhibiting the growth of or destroying bacteria in a warmblooded animal which comprises [enterally] *perorally* or parenterally administering to said animal an effective antibiotic amount of a compound of claim 1.

*6. The compound of claim 1 which is D-α[3-(2-p-aminosulfonylanilino-4-hydroxy-5-pyrimidyl)-ureido]-p-hydroxybenzylpenicillin sodium.*

*7. An antibiotic pharmaceutical dosage unit composition consisting essentially of an inert pharmaceutical carrier and an effective antibiotic amount of the compound of claim 6.*

*8. The method of inhibiting the growth of or destroying bacteria in a warmblooded animal which comprises perorally or parenterally administering to said animal an effective antibiotic amount of the compound of claim 6.*

* * * * *

UNITED STATES PATENT AND TRADEMARK OFFICE

CERTIFICATE OF CORRECTION

PATENT NO. : RE 31,926

DATED : June 25, 1985

INVENTOR(S) : BERND WETZEL ET AL.

It is certified that error appears in the above-identified patent and that said Letters Patent is hereby corrected as shown below:

Column 19, line 49: "$CH_3S$" should read -- $CH_2S$ --.

Column 21, line 12: should have NH

Column 23, line 66: "to above" should read -- to the above --.

Column 28, line 28: "phosgen-" should read -- phosgene --.

Column 28, line 29: "eand" should read -- and --.

Column 30, line 61: "(2H," should read -- (2H) --.

Column 30, line 67: "amoxycillin of trihydrate" should read -- amoxycillin trihydrate --.

Column 32, line 22: "of a" should read -- of --.

Column 40, line 57: "os" should read -- of --.

Column 41, line 23: "$cm^{31\ 1}$" should read -- $cm^{1}$ --.

Column 42, line 41: "phenylethylγ" should read -- phenylethyl) --.

Column 44, line 5: "'3" should read -- [3 --.

Column 44, line 9: "primidine" should read -- pyrimidine --.

Column 45, line 38: "7.5(5)" should read -- 7.5(5H) --.

Column 46, line 30: "CD + OD" should read -- $CD_3OD$ --.

UNITED STATES PATENT AND TRADEMARK OFFICE

CERTIFICATE OF CORRECTION

PATENT NO. : RE 31,926

DATED : June 25, 1985

INVENTOR(S) : BERND WETZEL ET AL.

It is certified that error appears in the above-identified patent and that said Letters Patent is hereby corrected as shown below:

Column 48, line 52: "and" should read -- of --.

Column 49, line 56: "isopropylamine" should read -- isopropylamino --.

Column 60, line 26: "ureidol]" should read -- ureido] --.

Column 69, line 40: "(2-bromoanilino" should read -- (2-p-bromoanilino --.

Column 69, line 56: "hydroxy-pyrimidyl)" should read -- hydroxy-5-pyrimidyl --.

Column 70, line 10: "(83.5)" should read -- (83.5%) --.

Column 70, line 22: "amino2" should read -- amino-2 --.

Column 70, line 55: "(43.5)" should read -- (43.5%) --.

Column 72, line 36: "(0.0005)" should read -- (0.005) --.

Column 74, line 36: "8:5" should read -- 8.5 --.

Column 76, line 14: "[-(2" should read -- [3-(2 --.

Column 76, line 62: "ad" should read -- and --.

Column 76, line 65: "NRM" should read -- NMR --.

UNITED STATES PATENT AND TRADEMARK OFFICE

CERTIFICATE OF CORRECTION

PATENT NO. : RE 31,926

DATED : June 25, 1985

INVENTOR(S) : BERND WETZEL ET AL.

It is certified that error appears in the above-identified patent and that said Letters Patent is hereby corrected as shown below:

Column 78, line 4: "(2-amino" should read -- (2-p-amino --.

Signed and Sealed this

*Twenty-fourth* Day of *December 1985*

[SEAL]

*Attest:*

DONALD J. QUIGG

*Attesting Officer* *Commissioner of Patents and Trademarks*